US008491918B2

(12) United States Patent
Rappuoli et al.

(10) Patent No.: US 8,491,918 B2
(45) Date of Patent: Jul. 23, 2013

(54) **POLYPEPTIDES FROM *NEISSERIA MENINGITIDIS***

(75) Inventors: Rino Rappuoli, Siena (IT); Claire Fraser, Potomac, MD (US); Mariagrazia Pizza, Siena (IT); Maria Scarselli, Siena (IT); Davide Serruto, Siena (IT); Hervé Tettelin, Gaithersburg, MD (US)

(73) Assignees: J. Craig Venter Institute, Inc., Rockville, MD (US); Novartis AG, Basel (CH)

( * ) Notice: Subject to any disclaimer, the term of this patent is extended or adjusted under 35 U.S.C. 154(b) by 0 days.

(21) Appl. No.: 13/272,982

(22) Filed: Oct. 13, 2011

(65) Prior Publication Data

US 2012/0027801 A1 Feb. 2, 2012

Related U.S. Application Data

(63) Continuation of application No. 12/306,920, filed as application No. PCT/IB2007/002838 on Jun. 29, 2007, now Pat. No. 8,039,007.

(60) Provisional application No. 60/817,950, filed on Jun. 29, 2006.

(51) Int. Cl.

| | |
|---|---|
| ***A61K 39/095*** | (2006.01) |
| ***C07H 21/04*** | (2006.01) |
| ***C07K 14/22*** | (2006.01) |

(52) U.S. Cl.
USPC ..................... 424/250.1; 424/234.1; 530/350; 435/69.7

(58) Field of Classification Search
None
See application file for complete search history.

(56) References Cited

U.S. PATENT DOCUMENTS

| | | | | |
|---|---|---|---|---|
| 7,504,111 | B2 | 3/2009 | Fontana et al. | |
| 7,862,827 | B2 * | 1/2011 | Giuliani et al. | 424/250.1 |
| 2002/0082206 | A1 | 6/2002 | Leach et al. | |

FOREIGN PATENT DOCUMENTS

| | | |
|---|---|---|
| WO | WO-02/079243 | 10/2002 |
| WO | WO2004058805 A2 * | 7/2004 |

OTHER PUBLICATIONS

Houghten et al. (Vaccines, 1986, Edited by Fred Brown: Cold Spring Harbor Laboratory).*
Holmes, Exp. Opin.Invest. Drugs, 2001, 10(3):511-519).*
Greenspan et al (Nature Biotechnology, 1999, 7:936-937).*
Database Geneseq [Online]. "Protein encoded by Prokaryotic essential gene #23450." XP002467933, retrieved from EBI accession No. GSP:ABU37923, from patent application WO200277183, 2002.
Database Geneseq [Online]. "Prokaryotic essential gene #23450." XP002467934, retrieved from EBI accession No. GSN:ACA41793, from patent application W0200277183, 2002.
Parkhill, J. et al. (Mar. 2000). "Complete DNA Sequence of a Serogroup A Strain of *Neisseria meningitides* Z2491," Nature 404(6777):502-506.
Pizza et al. (2000). "Identification of Vaccine Candidates Against Serogroup B Meningococcus by Whole-Genome Sequencing," Science 287(5459):1816-1820.
Tettelin et al. (Mar. 10, 2000). "Complete Genome Sequence of *Neisseria meningitidis* Serogroup B Strain MC58," Science 287(5459):1809-1815.

* cited by examiner

*Primary Examiner* — Padma V Baskar
(74) *Attorney, Agent, or Firm* — Morrison & Foerster LLP

(57) ABSTRACT

Various specific meningococcal proteins are disclosed. The invention provides related polypeptides, nucleic acids, antibodies and methods. These can all be used in medicine for treating or preventing disease and/or infection caused by meningococcus, such as bacterial meningitis.

8 Claims, No Drawings

POLYPEPTIDES FROM *NEISSERIA MENINGITIDIS*

CROSS REFERENCE TO RELATED APPLICATIONS

This application is a Continuation of U.S. patent application Ser. No. 12/306,920 (Now U.S. Pat. No. 8,039,007), filed Sep. 21, 2009, which is the National Stage of International Patent Application of PCT/IB2007/002838, filed Jun. 29, 2007, which claims the benefit of U.S. Provisional Patent Application Ser. No. 60/817,950, filed Jun. 29, 2006, each of which is hereby incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 529552001801SeqList.txt, date recorded: Oct. 6, 2011, size: 231 KB).

Technical Field

This invention is in the field of *Neisseria meningitidis.*

Background Art

*Neisseria meningitidis* (meningococcus) is a non-motile Gram negative diplococcus that is pathogenic in humans. It colonises the pharynx and causes meningitis (and, occasionally, septicaemia in the absence of meningitis).

All pathogenic meningococci have a polysaccharide capsule. These polysaccharides form the basis of available vaccines against meningococcus serogroups A, C, W135 and Y, but they are inappropriate for use against serogroup B. There has thus been a great deal of research into identifying alternative antigens for immunising against serogroup B. Such alternatives have included proteins, the lipopolysaccharide, and outer membrane vesicles.

References 1 to 7 disclose various polypeptides derived from the genome sequence of a serogroup B meningococcus, and they select specific sequences for use in vaccines. Genome sequence for a serogroup A strain is disclosed in reference 8.

It is an object of the invention to provide further polypeptides for use in the development of vaccines for preventing and/or treating meningococcal infections. In particular, it is an object to provide polypeptides for use in improved vaccines for preventing and/or treating meningococcal meningitis. The polypeptides may also be useful for diagnostic purposes, and as targets for antibiotics.

Disclosure of the Invention

Polypeptides

The invention provides polypeptides comprising the meningococcal amino acid sequences disclosed in the examples. These amino acid sequences are the even SEQ ID NOs between 2 and 78. There are thus 39 amino acid sequences, and these are referred to as B269_nn, where nn is a number between 01 and 50 (there are eleven B269_nn numbers that have no sequence: 02, 03, 04, 05, 06, 07, 08, 09, 10, 12 & 40). Two preferred sequences are B269_32 and B269_37.

The invention also provides polypeptides comprising amino acid sequences that have sequence identity to the meningococcal amino acid sequences disclosed in the examples. Depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more). These polypeptides include homologs, orthologs, allelic variants and functional mutants. Typically, 50% identity or more between two polypeptide sequences is considered to be an indication of functional equivalence. For any particular SEQ ID, the degree of sequence identity is preferably greater than both of the values in columns (B) and (A) of Table II herein, and is more preferably greater than all of the values in columns (C), (B) and (A) for that SEQ ID.

These polypeptide may, compared to the meningococcal sequences of the examples, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cystine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may also include one or more (e.g. 1, 2, 3, 4, 5, 6, 7, 8, 9, 10, etc.) single amino acid deletions relative to the meningococcal sequences of the examples. The polypeptides may also include one or more (e.g. 1, 2, 3, 4, 5, 6, 7, 8, 9, 10, etc.) insertions (e.g. each of 1, 2, 3, 4 or 5 amino acids) relative to the meningococcal sequences of the examples.

The invention further provides polypeptides comprising fragments of the meningococcal amino acid sequences disclosed in the examples. The fragments should comprise at least n consecutive amino acids from the sequences and, depending on the particular sequence, n is 7 or more (e.g. 8, 10, 12, 14, 16, 18, 20, 22, 24, 26, 28, 30, 35, 40, 45, 50, 60, 70, 80, 90, 100 or more).

The fragment may comprise at least one T-cell or, preferably, a B-cell epitope of the sequence. T- and B-cell epitopes can be identified empirically (e.g. using PEPSCAN [9,10] or similar methods), or they can be predicted (e.g. using the Jameson-Wolf antigenic index [11], matrix-based approaches [12], TEPITOPE [13], neural networks [14], OptiMer & EpiMer [15, 16], ADEPT [17], Tsites [18], hydrophilicity [19], antigenic index [20] or the methods disclosed in reference 21 etc.). Other preferred fragments are (a) the N-terminal signal peptides of the meningococcal polypeptides of the invention, (b) the meningococcal polypeptides, but without their N-terminal signal peptides, (c) the meningococcal polypeptides, but without their N-terminal amino acid residue.

Polypeptides of the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides <40 amino acids long involves in vitro chemical synthesis [22,23]. Solid-phase peptide synthesis is particularly preferred, such as methods based on tBoc or Fmoc [24] chemistry. Enzymatic synthesis [25] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [26]. Where D-amino acids are included, however, it is preferred to use chemical synthesis. Polypeptides of the invention may have covalent modifications at the C-terminus and/or N-terminus.

Polypeptides of the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides of the invention are preferably provided in purified or substantially purified form i.e. substantially free from other polypeptides (e.g. free from naturally-occurring polypeptides), particularly from other meningococcal or host cell polypeptides, and are generally at least about 50% pure (by weight), and usually at least about 90% pure i.e. less than about 50%, and more preferably less than about 10% (e.g. 5%) of a composition is made up of other expressed polypeptides. Polypeptides of the invention are preferably meningococcal polypeptides. Polypeptides of the invention preferably have the function indicated in Table I for the relevant sequence.

Polypeptides of the invention may be attached to a solid support. Polypeptides of the invention may comprise a detectable label (e.g. a radioactive or fluorescent label, or a biotin label).

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains. Polypeptides of the invention can be naturally or non-naturally glycosylated (i.e. the polypeptide has a glycosylation pattern that differs from the glycosylation pattern found in the corresponding naturally occurring polypeptide).

The invention provides polypeptides comprising a sequence -X-Y- or -Y-X-, wherein: -X- is an amino acid sequence as defined above and -Y- is not a sequence as defined above i.e. the invention provides fusion proteins. Where the N-terminus codon of a polypeptide-coding sequence is not ATG then that codon will be translated as the standard amino acid for that codon rather than as a Met, which occurs when the codon is a start codon.

The invention provides a process for producing polypeptides of the invention, comprising the step of culturing a host cell of to the invention under conditions which induce polypeptide expression.

The invention provides a process for producing a polypeptide of the invention, wherein the polypeptide is synthesised in part or in whole using chemical means.

The invention provides a composition comprising two or more polypeptides of the invention.

The invention also provides a hybrid polypeptide represented by the formula $NH_2$-A-[-X-L-]$_n$-B—COOH, wherein X is a polypeptide of the invention as defined above, L is an optional linker amino acid sequence, A is an optional N-terminal amino acid sequence, B is an optional C-terminal amino acid sequence, and n is an integer greater than 1. The value of n is between 2 and x, and the value of x is typically 3, 4, 5, 6, 7, 8, 9 or 10. Preferably n is 2, 3 or 4; it is more preferably 2 or 3; most preferably, n=2. For each n instances, -X- may be the same or different. For each n instances of [-X-L-], linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples include short peptide sequences which facilitate cloning, poly-glycine linkers (i.e. $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. -A- and -B- are optional sequences which will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct polypeptide trafficking, or short peptide sequences which facilitate cloning or purification (e.g. histidine tags i.e. $His_n$ where n=3, 4, 5, 6, 7, 8, 9, 10 or more). Other suitable N-terminal and C-terminal amino acid sequences will be apparent to those skilled in the art.

Various tests can be used to assess the in vivo immunogenicity of polypeptides of the invention. For example, polypeptides can be expressed recombinantly and used to screen patient sera by immunoblot. A positive reaction between the polypeptide and patient serum indicates that the patient has previously mounted an immune response to the protein in question i.e. the protein is an immunogen. This method can also be used to identify immunodominant proteins.

Antibodies

The invention provides antibodies that bind to polypeptides of the invention. These may be polyclonal or monoclonal and may be produced by any suitable means (e.g. by recombinant expression). To increase compatibility with the human immune system, the antibodies may be chimeric or humanised (e.g. refs. 27 & 28), or fully human antibodies may be used. The antibodies may include a detectable label (e.g. for diagnostic assays). Antibodies of the invention may be attached to a solid support. Antibodies of the invention are preferably neutralising antibodies.

Monoclonal antibodies are particularly useful in identification and purification of the individual polypeptides against which they are directed. Monoclonal antibodies of the invention may also be employed as reagents in immunoassays, radioimmunoassays (RIA) or enzyme-linked immunosorbent assays (ELISA), etc. In these applications, the antibodies can be labelled with an analytically-detectable reagent such as a radioisotope, a fluorescent molecule or an enzyme. The monoclonal antibodies produced by the above method may also be used for the molecular identification and characterization (epitope mapping) of polypeptides of the invention.

Antibodies of the invention are preferably provided in purified or substantially purified form. Typically, the antibody will be present in a composition that is substantially free of other polypeptides e.g. where less than 90% (by weight), usually less than 60% and more usually less than 50% of the composition is made up of other polypeptides.

Antibodies of the invention can be of any isotype (e.g. IgA, IgG, IgM i.e. but will generally be IgG. Within the IgG isotype, antibodies may be IgG1, IgG2, IgG3 or IgG4 subclass. Antibodies of the invention Antibodies of the invention can take various forms, including whole antibodies, antibody fragments such as F(ab')2 and F(ab) fragments, Fv fragments (non-covalent heterodimers), single-chain antibodies such as single chain Fv molecules (scFv), minibodies, oligobodies, etc. The term "antibody" does not imply any particular origin, and includes antibodies obtained through non-conventional processes, such as phage display.

The invention provides a process for detecting polypeptides of the invention, comprising the steps of: (a) contacting an antibody of the invention with a biological sample under conditions suitable for the formation of an antibody-antigen complexes; and (b) detecting said complexes.

The invention provides a process for detecting antibodies of the invention, comprising the steps of: (a) contacting a polypeptide of the invention with a biological sample (e.g. a blood or serum sample) under conditions suitable for the formation of an antibody-antigen complexes; and (b) detecting said complexes.

Nucleic Acids

The invention provides nucleic acid comprising the meningococcal nucleotide sequences disclosed in the examples. These nucleic acid sequences are the odd SEQ ID NOs between 1 and 77.

The invention also provides nucleic acid comprising nucleotide sequences having sequence identity to the meningococcal nucleotide sequences disclosed in the examples.

The invention also provides nucleic acid which can hybridize to the meningococcal nucleic acid disclosed in the examples. Hybridization reactions can be performed under conditions of different "stringency". Conditions that increase stringency of a hybridization reaction of widely known and published in the art [e.g. page 7.52 of reference 29]. Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art [e.g. see references 29-32, etc.].

In some embodiments, nucleic acid of the invention hybridizes to a target of the invention under low stringency conditions; in other embodiments it hybridizes under intermediate stringency conditions; in preferred embodiments, it hybridizes under high stringency conditions. An exemplary set of low stringency hybridization conditions is 50° C. and 10×SSC. An exemplary set of intermediate stringency hybridization conditions is 55° C. and 1×SSC. An exemplary set of high stringency hybridization conditions is 68° C. and 0.1×SSC.

Nucleic acid comprising fragments of these sequences are also provided. These should comprise at least n consecutive nucleotides from the meningococcal sequences and, depending on the particular sequence, n is 10 or more (e.g. 12, 14, 15, 18, 20, 25, 30, 35, 40, 50, 60, 70, 80, 90, 100, 150, 200 or more).

The invention provides nucleic acid of formula 5'-X-Y-Z-3', wherein: -X- is a nucleotide sequence consisting of x nucleotides; -Z- is a nucleotide sequence consisting of z nucleotides; -Y- is a nucleotide sequence consisting of either (a) a fragment of one of the odd-numbered SEQ ID NOS: 1 to 77, or (b) the complement of (a); and said nucleic acid 5'-X-Y-Z-3' is neither (i) a fragment of one of the odd-numbered SEQ ID NOS: 1 to 77 nor (ii) the complement of (i). The -X- and/or -Z- moieties may comprise a promoter sequence (or its complement).

The invention also provides nucleic acid encoding the polypeptides and polypeptide fragments of the invention.

The invention includes nucleic acid comprising sequences complementary to the sequences disclosed in the sequence listing (e.g. for antisense or probing, or for use as primers), as well as the sequences in the orientation actually shown.

Nucleic acids of the invention can be used in hybridisation reactions (e.g. Northern or Southern blots, or in nucleic acid microarrays or 'gene chips') and amplification reactions (e.g. PCR, SDA, SSSR, LCR, TMA, NASBA, etc.) and other nucleic acid techniques.

Nucleic acid according to the invention can take various forms (e.g. single-stranded, double-stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids of the invention are preferably provided in purified or substantially purified form i.e. substantially free from other nucleic acids (e.g. free from naturally-occurring nucleic acids), particularly from other *Haemophilus* or host cell nucleic acids, generally being at least about 50% pure (by weight), and usually at least about 90% pure. Nucleic acids of the invention are preferably *H. influenzae* nucleic acids.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acid of the invention may be attached to a solid support (e.g. a bead, plate, filter, film, slide, microarray support, resin, etc.). Nucleic acid of the invention may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention comprise meningococcal sequences as defined above, but they may also comprise non-meningococcal sequences (e.g. in nucleic acids of formula 5'-X-Y-Z-3', as defined above). This is particularly useful for primers, which may thus comprise a first sequence complementary to a PCAV nucleic acid target and a second sequence which is not complementary to the nucleic acid target. Any such non-complementary sequences in the primer are preferably 5' to the complementary sequences. Typical non-complementary sequences comprise restriction sites or promoter sequences.

Nucleic acids of the invention can be prepared in many ways e.g. by chemical synthesis (at least in part), by digesting longer nucleic acids using nucleases (e.g. restriction enzymes), by joining shorter nucleic acids (e.g. using ligases or polymerases), from genomic or cDNA libraries, etc.

Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector. Preferred vectors are plasmids. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

Where a nucleic acid is DNA, it will be appreciated that "U" in a RNA sequence will be replaced by "T" in the DNA. Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T). The terms also imply a direction—the complement of 5'-ACAGT-3' is 5'-ACTGT-3' rather than 5'-TGTCA-3'.

Nucleic acids of the invention can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid of the invention, wherein the nucleic acid is synthesised in part or in whole using chemical means.

The invention provides vectors comprising nucleotide sequences of the invention (e.g. cloning or expression vectors) and host cells transformed with such vectors.

The invention also provides a kit comprising primers (e.g. PCR primers) for amplifying a template sequence contained within a meningococcus nucleic acid sequence, the kit comprising a first primer and a second primer, wherein the first primer is substantially complementary to said template sequence and the second primer is substantially complementary to a complement of said template sequence, wherein the parts of said primers which have substantial complementarity define the termini of the template sequence to be amplified. The first primer and/or the second primer may include a detectable label (e.g. a fluorescent label).

The invention also provides a kit comprising first and second single-stranded oligonucleotides which allow amplification of a meningococcal template nucleic acid sequence contained in a single- or double-stranded nucleic acid (or mixture thereof), wherein: (a) the first oligonucleotide comprises a primer sequence which is substantially complementary to said template nucleic acid sequence; (b) the second oligonucleotide comprises a primer sequence which is substantially complementary to the complement of said template nucleic acid sequence; (c) the first oligonucleotide and/or the second oligonucleotide comprise(s) sequence which is not complementary to said template nucleic acid; and (d) said primer sequences define the termini of the template sequence to be amplified. The non-complementary sequence(s) of feature (c) are preferably upstream of (i.e. 5' to) the primer sequences. One or both of these (c) sequences may comprise a restriction site [e.g. ref. 33] or a promoter sequence [e.g. 34]. The first oligonucleotide and/or the second oligonucleotide may include a detectable label (e.g. a fluorescent label).

The template sequence may be any part of a genome sequence.

The invention provides a process for detecting nucleic acid of the invention, comprising the steps of: (a) contacting a nucleic probe according to the invention with a biological sample under hybridising conditions to form duplexes; and (b) detecting said duplexes.

The invention provides a process for detecting meningococcus in a biological sample (e.g. blood), comprising the step of contacting nucleic acid according to the invention with the biological sample under hybridising conditions. The process may involve nucleic acid amplification (e.g. PCR, SDA, SSSR, LCR, TMA, NASBA, etc.) or hybridisation (e.g. microarrays, blots, hybridisation with a probe in solution etc.).

The invention provides a process for preparing a fragment of a target sequence, wherein the fragment is prepared by extension of a nucleic acid primer. The target sequence and/or the primer are nucleic acids of the invention. The primer extension reaction may involve nucleic acid amplification (e.g. PCR, SDA, SSSR, LCR, TMA, NASBA, etc.).

Nucleic acid amplification according to the invention may be quantitative and/or real-time.

For certain embodiments of the invention, nucleic acids are preferably at least 7 nucleotides in length (e.g. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 90, 100, 110, 120, 130, 140, 150, 160, 170, 180, 190, 200, 225, 250, 275, 300 nucleotides or longer).

For certain embodiments of the invention, nucleic acids are preferably at most 500 nucleotides in length (e.g. 450, 400, 350, 300, 250, 200, 150, 140, 130, 120, 110, 100, 90, 80, 75, 70, 65, 60, 55, 50, 45, 40, 39, 38, 37, 36, 35, 34, 33, 32, 31, 30, 29, 28, 27, 26, 25, 24, 23, 22, 21, 20, 19, 18, 17, 16, 15 nucleotides or shorter).

Primers and probes of the invention, and other nucleic acids used for hybridization, are preferably between 10 and 30 nucleotides in length (e.g. 10, 11, 12, 13, 14, 15, 16, 17, 18, 19, 20, 21, 22, 23, 24, 25, 26, 27, 28, 29, or 30 nucleotides).

Pharmaceutical Compositions

The invention provides compositions comprising: (a) polypeptide, antibody, and/or nucleic acid of the invention; and (b) a pharmaceutically acceptable carrier. These compositions may be suitable as immunogenic compositions, for instance, or as diagnostic reagents, or as vaccines. Vaccines according to the invention may either be prophylactic (i.e. to prevent infection) or therapeutic (i.e. to treat infection), but will typically be prophylactic.

A 'pharmaceutically acceptable carriers' includes any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc.

Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in ref. 141.

Compositions of the invention may include an antimicrobial, particularly if packaged in a multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

Polypeptides of the invention may be administered in conjunction with other immunoregulatory agents. In particular, compositions will usually include a vaccine adjuvant. Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 35], or mixtures of different mineral compounds, with the compounds taking any suitable form (e.g. gel, crystalline, amorphous, etc.), and with adsorption being preferred. The mineral containing compositions may also be formulated as a particle of metal salt [36].

Aluminium phosphates are particularly preferred, particularly in compositions which include a *H. influenzae* saccharide antigen, and a typical adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where there is more than one conjugate in a composition, not all conjugates need to be adsorbed.

B. Oil Emulsions

Oil emulsion compositions suitable for use as adjuvants in the invention include squalene-water emulsions, such as MF59 [Chapter 10 of ref. 35; see also ref. 37] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref. 35]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 38. Saponin formulations may also comprise a sterol, such as cholesterol [39].

Combinations of saponins and cholesterols can be used to form unique particles called immunostimulating complexs (ISCOMs) [chapter 23 of ref. 35]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 39-41. Optionally, the ISCOMS may be devoid of additional detergent [42].

A review of the development of saponin based adjuvants can be found in refs. 43 & 44.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 45-50. Virosomes are discussed further in, for example, ref. 51

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 52. Such "small particles" of 3dMPL are small enough to be sterile filtered through a 0.22 μm membrane [52]. Other non-toxic LPS derivatives include monophosphoryl lipid A mimics, such as aminoalkyl glucosaminide phosphate derivatives e.g. RC-529 [53,54].

Lipid A derivatives include derivatives of lipid A from *Escherichia coli* such as OM-174. OM-174 is described for example in refs. 55 & 56.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 57, 58 and 59 disclose possible analog substitutions e.g. replacement of guanosine with 2'-deoxy-7-deazaguanosine. The adjuvant effect of CpG oligonucleotides is further discussed in refs. 60-65.

The CpG sequence may be directed to TLR9, such as the motif GTCGTT or TTCGTT [66]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 67-69. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 66 & 70-72.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 73 and as parenteral adjuvants in ref. 74. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivaties thereof, particularly LT-K63 and LT-R72, as adjuvants can be found in refs. 75-82. Numerical reference for amino acid substitutions is preferably based on the alignments of the A and B subunits of ADP-ribosylating toxins set forth in ref. 83, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [84], etc.) [85], interferons (e.g. interferon- G. Bioadhesives and Mucoadhesives Bioadhesives and mucoadhesives may also be used as adjuvants in the invention. Suitable bioadhesives include esterified hyaluronic acid microspheres [86] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [87].

H. Microparticles

Microparticles may also be used as adjuvants in the invention. Microparticles (i.e. a particle of -toxic (e.g. α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 35)

Examples of liposome formulations suitable for use as adjuvants are described in refs. 88-90.

J. Polyoxyethylene Ether and Polyoxyethylene Ester Formulations

Adjuvants suitable for use in the invention include polyoxyethylene ethers and polyoxyethylene esters [91]. Such formulations further include polyoxyethylene sorbitan ester surfactants in combination with an octoxynol [92] as well as polyoxyethylene alkyl ethers or ester surfactants in combination with at least one additional non-ionic surfactant such as an octoxynol [93]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K Polyphosphazene (PCPP)

PCPP formulations are described, for example, in refs. 94 and 95.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M Imidazoquinolone Compounds.

Examples of imidazoquinolone compounds suitable for use adjuvants in the invention include Imiquamod and its homologues (e.g. "Resiquimod 3M"), described further in refs. 96 and 97.

The invention may also comprise combinations of aspects of one or more of the adjuvants identified above. For example, the following adjuvant compositions may be used in the invention: (1) a saponin and an oil-in-water emulsion [98]; (2) a saponin (e.g. QS21)+a non-toxic LPS derivative (e.g. 3dMPL) [99]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [100]; (5) combinations of 3dMPL with, for example, QS21 and/or oil-in-water emulsions [101]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 35.

The use of an aluminium hydroxide or aluminium phosphate adjuvant is particularly preferred, and antigens are generally adsorbed to these salts. Calcium phosphate is another preferred adjuvant.

The pH of compositions of the invention is preferably between 6 and 8, preferably about 7. Stable pH may be maintained by the use of a buffer. Where a composition comprises an aluminium hydroxide salt, it is preferred to use a histidine buffer [102]. The composition may be sterile and/or pyrogen-free. Compositions of the invention may be isotonic with respect to humans.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions of the invention may be packaged in unit dose form or in multiple dose form. For multiple dose forms, vials are preferred to pre-filled syringes. Effective dosage volumes can be routinely established, but a typical human dose of the composition for injection has a volume of Where a composition of the invention is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each meningococcal saccharide antigen per dose is between 1 μg and 10 mg per antigen.

Pharmaceutical Uses

The invention also provides a method of treating a patient, comprising administering to the patient a therapeutically effective amount of a composition of the invention. The patient may either be at risk from the disease themselves or may be a pregnant woman ('maternal immunisation').

The invention provides nucleic acid, polypeptide, or antibody of the invention for use as medicaments (e.g. as immunogenic compositions or as vaccines, including for use in treating or preventing disease and/or infection caused by meningococcus) or as diagnostic reagents. It also provides the use of nucleic acid, polypeptide, or antibody of the invention in the manufacture of: (i) a medicament for treating or preventing disease and/or infection caused by meningococcus; (ii) a diagnostic reagent for detecting the presence of meningococcus or of antibodies raised against meningococcus; and/or (iii) a reagent which can raise antibodies against meningococcus. Said meningococcus can be of any serogroup or strain, but is preferably in serogroup B. Said disease may be, for instance, bacterial meningitis (and particularly meningococcal meningitis) or septicaemia.

The patient is preferably a human. Where the vaccine is for prophylactic use, the human is preferably a child (e.g. a toddler or infant) or teenager e.g. ages 0-18 years; where the vaccine is for therapeutic use, the human is preferably an adult e.g. aged 18-55 years. A vaccine intended for children may also be administered to adults e.g. to assess safety, dosage, immunogenicity, etc.

One way of checking efficacy of therapeutic treatment involves monitoring meningococcal infection after administration of the composition of the invention. One way of checking efficacy of prophylactic treatment involves monitoring immune responses against an administered polypeptide after administration. Immunogenicity of compositions of the invention can be determined by administering them to test subjects (e.g. children 12-16 months age, or animal models) and then determining standard parameters including ELISA titres (GMT) of IgG. These immune responses will generally be determined around 4 weeks after administration of the composition, and compared to values determined before administration of the composition. Where more than one dose of the composition is administered, more than one post-administration determination may be made. A standard method for assessing prophylactic efficacy for meningococci is the serum bactericidal assay (SBA). Administration preferably results in an increase in SBA titre for the relevant serogroup of at least 4-fold, and preferably at least 8-fold, measured with human complement [103]. If rabbit complement is used to measure SBA titres then the titre increase is preferably at least 128-fold.

Administration of polypeptide antigens is a preferred method of treatment for inducing immunity. Administration of antibodies of the invention is another preferred method of treatment. This method of passive immunisation is particularly useful for newborn children or for pregnant women. This method will typically use monoclonal antibodies, which will be humanised or fully human.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Bacterial infections affect various areas of the body and so compositions may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 104 & 105].

Further Antigenic Components of Compositions of the Invention

The invention also provides a composition comprising a polypeptide or the invention and one or more of the following further antigens:

- a saccharide antigen from *N. meningitidis* serogroup A, C, W135 and/or Y (preferably all four), such as the oligosaccharide disclosed in ref. 106 from serogroup C [see also ref. 107] or the oligosaccharides of ref. 108.
- a saccharide antigen from *Streptococcus pneumoniae* [e.g. 109, 110, 111].
- an antigen from hepatitis A virus, such as inactivated virus [e.g. 112, 113].
- an antigen from hepatitis B virus, such as the surface and/or core antigens [e.g. 113, 114].
- a diphtheria antigen, such as a diphtheria toxoid [e.g. chapter 3 of ref. 115] e.g. the $CRM_{197}$ mutant [e.g. 116].
- a tetanus antigen, such as a tetanus toxoid [e.g. chapter 4 of ref. 115].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 117 & 118].

a saccharide antigen from *Haemophilus influenzae* B [e.g. 107].

polio antigen(s) [e.g. 119, 120] such as IPV.

measles, mumps and/or rubella antigens [e.g. chapters 9, 10 & 11 of ref. 115].

influenza antigen(s) [e.g. chapter 19 of ref. 115], such as the haemagglutinin and/or neuraminidase surface proteins.

an antigen from *Moraxella catarrhalis* [e.g. 121].

an protein antigen from *Streptococcus agalactiae* (group B streptococcus) [e.g. 122, 123].

a saccharide antigen from *Streptococcus agalactiae* (group B streptococcus).

an antigen from *Streptococcus pyogenes* (group A streptococcus) [e.g. 123, 124, 125].

an antigen from *Staphylococcus aureus* [e.g. 126].

The composition may comprise one or more of these further antigens.

Toxic protein antigens may be detoxified where necessary (e.g. detoxification of pertussis toxin by chemical and/or genetic means [118]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates include diphtheria toxin, tetanus toxin, the *N. meningitidis* outer membrane protein [127], synthetic peptides [128,129], heat shock proteins [130,131], pertussis proteins [132,133], protein D from *H. influenzae [*134], cytokines [135], lymphokines [135], streptococcal proteins, hormones [135], growth factors [135], toxin A or B from *C. difficile [*136], iron-uptake proteins [137], etc. A preferred carrier protein is the CRM197 diphtheria toxoid [138].

Antigens in the composition will typically be present at a concentration of at least 1 μg/ml each. In general, the concentration of any given antigen will be sufficient to elicit an immune response against that antigen.

As an alternative to using proteins antigens in the immunogenic compositions of the invention, nucleic acid (preferably DNA e.g. in the form of a plasmid) encoding the antigen may be used.

Antigens are preferably adsorbed to an aluminium salt.

Screening Methods

The invention provides a process for determining whether a test compound binds to a polypeptide of the invention. If a test compound binds to a polypeptide of the invention and this binding inhibits the life cycle of meningococcus, then the test compound can be used as an antibiotic or as a lead compound for the design of antibiotics. The process will typically comprise the steps of contacting a test compound with a polypeptide of the invention, and determining whether the test compound binds to said polypeptide. Preferred polypeptides of the invention for use in these processes are enzymes (e.g. tRNA synthetases), membrane transporters and ribosomal polypeptides. Suitable test compounds include polypeptides, polypeptides, carbohydrates, lipids, nucleic acids (e.g. DNA, RNA, and modified forms thereof), as well as small organic compounds (e.g. MW between 200 and 2000 Da). The test compounds may be provided individually, but will typically be part of a library (e.g. a combinatorial library). Methods for detecting a binding interaction include NMR, filter-binding assays, gel-retardation assays, displacement assays, surface plasmon resonance, reverse two-hybrid etc. A compound which binds to a polypeptide of the invention can be tested for antibiotic activity by contacting the compound with meningococcus bacteria and then monitoring for inhibition of growth. The invention also provides a compound identified using these methods.

Preferably, the process comprises the steps of: (a) contacting a polypeptide of the invention with one or more candidate compounds to give a mixture; (b) incubating the mixture to allow polypeptide and the candidate compound(s) to interact; and (c) assessing whether the candidate compound binds to the polypeptide or modulates its activity.

Once a candidate compound has been identified in vitro as a compound that binds to a polypeptide of the invention then it may be desirable to perform further experiments to confirm the in vivo function of the compound in inhibiting bacterial growth and/or survival. Thus the method comprise the further step of contacting the compound with a meningococcus and assessing its effect.

The polypeptide used in the screening process may be free in solution, affixed to a solid support, located on a cell surface or located intracellularly. Preferably, the binding of a candidate compound to the polypeptide is detected by means of a label directly or indirectly associated with the candidate compound. The label may be a fluorophore, radioisotope, or other detectable label.

General

The invention provides a computer-readable medium (e.g. a floppy disk, a hard disk, a CD-ROM, a DVD etc.) and/or a computer memory and/or a computer database containing one or more of the sequences in the sequence listing.

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Identity between polypeptides is preferably determined by the Smith-Waterman homology search algorithm as implemented in the MPSRCH program (Oxford Molecular), using an affine gap search with parameters gap open penalty=12 and gap extension penalty=1. Identity between sequences is preferably also determined by the Smith-Waterman homology search algorithm.

The N-terminus residues in the amino acid sequences in the sequence listing are given as the amino acid encoded by the first codon in the corresponding nucleotide sequence. Where the first codon is not ATG, it will be understood that it will be translated as methionine when the codon is a start codon, but will be translated as the indicated non-Met amino acid when the sequence is at the C-terminus of a fusion partner. The invention specifically discloses and encompasses each of the amino acid sequences of the sequence listing having a N-terminus methionine residue (e.g. a formyl-methionine residue) in place of any indicated non-Met residue.

Alternative start codons can be used in biology. The amino acid sequences in the sequence listing are based on particular start codons, but downstream start codons may alternatively be used. Thus the invention specifically discloses and encompasses each of the amino acid sequences of the sequence listing, starting at any methionine residue from the sequence that is downstream of the N-terminal residue shown in the sequence listing (e.g. SEQ ID NOs: 5 & 10).

As indicated in the above text, nucleic acids and polypeptides of the invention may include sequences that:

(a) are identical (i.e. 100% identical) to the sequences disclosed in the sequence listing;

(b) share sequence identity with the sequences disclosed in the sequence listing;

(c) have 1, 2, 3, 4, 5, 6, 7, 8, 9 or 10 single nucleotide or amino acid alterations (deletions, insertions, substitutions), which may be at separate locations or may be contiguous, as compared to the sequences of (a) or (b); and (d) when aligned with a particular sequence from the sequence listing using a pairwise alignment algorithm, a moving window of x monomers (amino acids or nucleotides) moving from start (N-terminus or 5') to end (C-terminus of 3'), such that for an alignment that extends to p monomers (where p>x) there are p−x+1 such windows, each window has at least xy identical aligned monomers, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if xy is not an integer then it is rounded up to the nearest integer. The preferred pairwise alignment algorithm is the Needleman-Wunsch global alignment algorithm [139], using default parameters (e.g. with Gap opening penalty=10.0, and with Gap extension penalty=0.5, using the EBLOSUM62 scoring matrix). This algorithm is conveniently implemented in the needle tool in the EMBOSS package [140].

The nucleic acids and polypeptides of the invention may additionally have further sequences to the N-terminus/5' and/or C-terminus/3' of these sequences (a) to (d).

The practice of the present invention will employ, unless otherwise indicated, conventional methods of chemistry, biochemistry, molecular biology, immunology and pharmacology, within the skill of the art. Such techniques are explained fully in the literature. See, e.g., references 141-148, etc.

MODES FOR CARRYING OUT THE INVENTION

Various encoded amino acid sequences have been identified in the genome of the M04-240196 strain of serogroup B *N. meningitidis*. 39 of them have been selected as useful antigens, based on various criteria, and their gene and amino acid sequences are given in the sequence listing.

Predicted biological functions are given in Table I, but the antigens' precise roles in meningococcus biology are not as important as their ability to function as immunogens. Table I also notes the closest match in the published serogroup A and B genomes in references 6 and 8, as well as in the unpublished genome of serogroup C strain FAM18. Where a sequence has more than 95% identity to a known sequence (and particularly where it has 100% identity) then the invention is more concerned with identifying the protein's useful antigenic properties than identifying the protein per se.

In addition to the annotations and comparisons, further features of interest include: B269_17 contains an intein domain; B269_34 has a junction sequence at its C-terminus; a transmembrane domain is present in B269_05, B269_10, B269_18, B269_24; and five transmembrane domains are present in B26915 and B269_29.

Using the sequence information herein, the proteins can readily be expressed in recombinant hosts and used to generate immune responses using techniques known in the art.

For instance, sequences encoding B269_proteins 11, 13, 14, 15, 17, 24, 25, 26, 29, 31, 32, 34, 36, 37, 51, 52, 53, 54, 55, 56, 57, 58 and 59 were inserted into expression vectors with a C-terminal poly-histidine tag. B269_proteins 14, 29, 31, 34, 37 were also expressed in a domain-truncated form. GST fusions of 37, 54, 55 and 57 were also prepared. Expressed proteins were purified from *E. coli*. Without any optimisation of expression, various degrees of purity were seen e.g. from 20% purity with domain B269_14 and B269_32, up to 95% purity with B269_51. Soluble expression was seen with B269_proteins 13, 24, 25, $31_{domain}$, 32, 51, 53 and 56.

Antibodies were raised against expressed proteins by injecting them into mice with Freund's complete adjuvant or aluminium hydroxide. Antisera were then used in western blots or FACS binding assays against meningococci. The following B269_proteins could be detected by western blot: 13; 25; $29_{domain}$; 31; $34_{domain}$; 51; 52; and 53. In addition, the following proteins could be detected in the blots at particular MWs: 11 (40 kDa); 24 (20 kDa); and 26 (28 kDa). FACS revealed the following proteins: 17; 24; 25; 26; $29_{domain}$; $34_{domain}$; and 53.

It will be understood that the invention has been described by way of example only and modifications may be made whilst remaining within the scope and spirit of the invention.

TABLE I

Annotations
aa = length of polypeptide

| B269 | SEQ ID | aa | Localisation* | Annotation |
|---|---|---|---|---|
| 01 | 2 | 588 | O | PilC protein |
| 11 | 4 | 320 | O | putative MafA-like adhesin |
| 13 | 6 | 387 | C | Cupin superfamily protein |
| 14 | 8 | 420 | I | membrane-fusion protein |
| 15 | 10 | 670 | I | peptidase, C39 family |
| 16 | 12 | 331 | P | putative peptidyl-prolyl cis-trans isomerase |
| 17 | 14 | 209 | S | conserved hypothetical protein |
| 18 | 16 | 265 | O | opacity protein |
| 19 | 18 | 680 | I | transferrin-binding protein 2 |
| 20 | 20 | 1370 | S | hemagglutinin-hemolysin-related protein |
| 21 | 22 | 734 | S | hemagglutinin-hemolysin-related protein |
| 22 | 24 | 887 | S | hemagglutinin-hemolysin-related protein |
| 23 | 26 | 794 | S | hemagglutinin-hemolysin-related protein |
| 24 | 28 | 206 | C | conserved hypothetical protein |
| 25 | 30 | 1502 | S | HlyJ haemolysin-like protein |
| 26 | 32 | 257 | C | conserved hypothetical protein TIGR00294 |
| 27 | 34 | 237 | I | putative thiosulphate sulphur transferase |
| 28 | 36 | 402 | C | probable: Putative GlcNAc transferase19 |
| 29 | 38 | 297 | O | conserved hypothetical protein |
| 30 | 40 | 226 | C | opacity protein Opa115 |
| 31 | 42 | 588 | O | YadA-like C-terminal region family |
| 32 | 44 | 201 | C | conserved hypothetical protein |
| 33 | 46 | 337 | I | putative glycosyltransferase |
| 34 | 48 | 529 | C | Iron-regulated protein frpA |
| 35 | 50 | 676 | C | transferrin/lactoferrin binding protein B |
| 36 | 52 | 203 | C | mucin |
| 37 | 54 | 340 | C | conserved hypothetical protein |
| 38 | 56 | 376 | I | putative two component sensor kinase196 |

TABLE I-continued

| Annotations aa = length of polypeptide | | | | |
|---|---|---|---|---|
| B269 | SEQ ID | aa | Localisation* | Annotation |
| 39 | 58 | 346 | P | ATP-binding region, ATPase-like:Histidine kinase A, N-terminal |
| 41 | 60 | 1026 | P | PilC protein |
| 42 | 62 | 333 | O | conserved hypothetical protein |
| 43 | 64 | 229 | C | glycosyl transferase, group 2 family protein |
| 44 | 66 | 208 | C | conserved hypothetical protein |
| 45 | 68 | 476 | C | mafB protein |
| 46 | 70 | 229 | C | adhesin MafB |
| 47 | 72 | 432 | O | transferrin binding protein B subunit19 |
| 48 | 74 | 809 | S | hemolysin-hemagglutinin-like protein HecA precursor, putative |
| 49 | 76 | 783 | S | Possible hemagglutinin (DUF637) family1 |
| 50 | 78 | 300 | S | hemagglutinin-hemolysin-related protein |

*Localisation key: O = outer membrane; C = cytoplasm; I = inner membrane; P = periplasmic space; S = secreted

TABLE II

Relationship to other meningococcal sequences [6, 8]
'MC58' = closest match from reference 6. Columns (a) to (c) are % matches to other sequences: (B) = ref 6; (A) = ref 8; (c) = strain FAM18.

| B269 | SEQ ID | MC58 | (B) | (A) | (C) |
|---|---|---|---|---|---|
| 01 | 2 | NMB0049 | 77.6 | 78.2 | 73.1 |
| 11 | 4 | NMB0652 | 62.7 | 100 | 98.4 |
| 13 | 6 | NMB1786 | 51 | 48.4 | 80.3 |
| 14 | 8 | NMB0097 | 51.1 | 59.9 | 100 |
| 15 | 10 | NMB0098 | 64 | 28.9 | 94.9 |
| 16 | 12 | NMB0281 | 85.4 | 92.1 | 93.5 |
| 17 | 14 | NMB0369 | 83.2 | 61.7 | 91.9 |
| 18 | 16 | NMB0442 | 86.4 | 81.5 | 87.1 |
| 19 | 18 | NMB0460 | 71.5 | 70.9 | 41.8 |
| 20 | 20 | NMB1779 | 67.4 | 70 | 97.4 |
| 21 | 22 | NMB1775 | 82.6 | 87.9 | 96 |
| 22 | 24 | NMB1779 | 81.9 | 80.5 | 95.2 |
| 23 | 26 | NMB1775 | 79.2 | 89.2 | 88.9 |
| 24 | 28 | NMB0515 | 66.1 | 99.5 | 93.7 |
| 25 | 30 | NMB0585 | 85.5 | 91 | 90.9 |
| 26 | 32 | NMB0803 | 86.8 | 86.8 | 86.8 |
| 27 | 34 | NMB0841 | 84 | 95.4 | 88.1 |
| 28 | 36 | NMB0846 | 89 | 56.1 | 85.1 |
| 29 | 38 | NMB0888 | 87.9 | 79.8 | 85.2 |
| 30 | 40 | NMB1636 | 80.4 | 81.6 | 92 |
| 31 | 42 | NMB0992 | 87.4 | 90.1 | 94.6 |
| 32 | 44 | none | 41.2 | 41.2 | 70.9 |
| 33 | 46 | NMB1255 | 73 | 95.4 | 97.5 |
| 34 | 48 | NMB1415 | 89.5 | 80.5 | 98.7 |
| 35 | 50 | NMB1541 | 68.3 | 78.2 | 56.4 |
| 36 | 52 | NMB0891 | 49 | 53.4 | 78.6 |
| 37 | 54 | none | 30.7 | 33.3 | 100 |
| 38 | 56 | NMB1606 | 82.2 | 80.1 | 87 |
| 39 | 58 | NMB1606 | 83 | 85.9 | 90.9 |
| 41 | 60 | NMB1847 | 80.4 | 81.6 | 78.2 |
| 42 | 62 | NMB1870 | 87.4 | 87.4 | 74.2 |
| 43 | 64 | NMB1929 | 48.2 | 48.2 | 48.2 |
| 44 | 66 | NMB1992 | 89.9 | 81.5 | 92.8 |
| 45 | 68 | NMB2105 | 89.7 | 88.5 | 95.9 |
| 46 | 70 | NMB2105 | 88 | 96.7 | 89.9 |
| 47 | 72 | NMB2132 | 76.5 | 68.6 | 68.7 |
| 48 | 74 | NMB0493 | 85.4 | 55 | 68.2 |
| 49 | 76 | NMB1775 | 67.2 | 82.9 | 99.4 |
| 50 | 78 | NMB1779 | 51.2 | 84 | 83.3 |

References (the Contents of which are Hereby Incorporated by Reference)

[1] WO99/24578.
[2] WO99/36544.
[3] WO99/57280.
[4] WO00/22430.
[5] WO00/66791.
[6] Tettelin et al. (2000) *Science* 287:1809-16.
[7] Pizza et al. (2000) *Science* 287:1-1816-20.
[8] Parkhill et al. (2000) *Nature* 404:502-8.
[9] Geysen et al. (1984) *PNAS USA* 81:3998-4002.
[10] Carter (1994) *Methods Mol Biol* 36:207-23.
[11] Jameson, B A et al. 1988, *CABIOS* 4(1):181-186.
[12] Raddrizzani & Hammer (2000) *Brief Bioinform* 1(2): 179-89.
[13] De Lalla et al. (1999) *J. Immunol.* 163:1725-29.
[14] Brusic et al. (1998) *Bioinformatics* 14(2):121-30
[15] Meister et al. (1995) *Vaccine* 13(6):581-91.
[16] Roberts et al. (1996) *AIDS Res Hum Retroviruses* 12(7): 593-610.
[17] Maksyutov & Zagrebelnaya (1993) *Comput Appl Biosci* 9(3):291-7.
[18] Feller & de la Cruz (1991) *Nature* 349(6311):720-1.
[19] Hopp (1993) *Peptide Research* 6:183-190.
[20] Welling et al. (1985) *FEBS Lett.* 188:215-218.
[21] Davenport et al. (1995) *Immunogenetics* 42:392-297.
[22] Bodanszky (1993) *Principles of Peptide Synthesis* (ISBN: 0387564314).
[23] Fields et al. (1997) *Meth Enzymol* 289*: Solid-Phase Peptide Synthesis*. ISBN: 0121821900.
[24] Chan & White (2000) *Fmoc Solid Phase Peptide Synthesis*. ISBN: 0199637245.
[25] Kullmann (1987) *Enzymatic Peptide Synthesis*. ISBN: 0849368413.
[26] Ibba (1996) *Biotechnol Genet Eng Rev* 13:197-216.
[27] Breedveld (2000) *Lancet* 355(9205):735-740.
[28] Gorman & Clark (1990) *Seinin. Iminunol.* 2:457-466.
[29] Sambrook et al. (1989) *Molecular Cloning: A Laboratory Manual.*
[30] *Short protocols in molecular biology* (4th ed, 1999) Ausubel et al. eds. ISBN 0-471-32938-X.
[31] U.S. Pat. No. 5,707,829
[32] *Current Protocols in Molecular Biology* (F. M. Ausubel et al eds., 1987) Supplement 30.
[33] EP-B-0509612.
[34] EP-B-0505012.
[35] *Vaccine Design* . . . (1995) eds. Powell & Newman. ISBN: 030644867X. Plenum.
[36] WO00/23105.
[37] WO90/14837.
[38] U.S. Pat. No. 5,057,540.
[39] WO96/33739.
[40] EP-A-0109942.
[41] WO96/11711.
[42] WO00/07621.
[43] Barr et al. (1998) *Advanced Drug Delivery Reviews* 32:247-271.
[44] Sjolanderet et al. (1998) *Advanced Drug Delivery Reviews* 32:321-338.
[45] Niikura et al. (2002) *Virology* 293:273-280.
[46] Lenz et al. (2001) *J Immunol* 166:5346-5355.
[47] Pinto et al. (2003) *J Infect Dis* 188:327-338.
[48] Gerber et al. (2001) *Virol* 75:4752-4760.
[49] WO03/024480
[50] WO03/024481
[51] Gluck et al. (2002) *Vaccine* 20:B10-B16.
[52] EP-A-0689454.
[53] Johnson et al. (1999) *Bioorg Med Chen*2 Lett 9:2273-2278.
[54] Evans et al. (2003) *Expert Rev Vaccines* 2:219-229.
[55] Meraldi et al. (2003) *Vaccine* 21:2485-2491.
[56] Pajak et al. (2003) *Vaccine* 21:836-842.

[57] Kandimalla et al. (2003) *Nucleic Acids Research* 31:2393-2400.
[58] WO02/26757.
[59] WO99/62923.
[60] Krieg (2003) *Nature Medicine* 9:831-835.
[61] McCluskie et al. (2002) *FEMS Immunology and Medical Microbiology* 32:179-185.
[62] WO98/40100.
[63] U.S. Pat. No. 6,207,646.
[64] U.S. Pat. No. 6,239,116.
[65] U.S. Pat. No. 6,429,199.
[66] Kandimalla et al. (2003) *Biochemical Society Transactions* 31 (part 3):654-658.
[67] Blackwell et al. (2003) *J Immunol* 170:4061-4068.
[68] Krieg (2002) *Trends Immunol* 23:64-65.
[69] WO01/95935.
[70] Kandimalla et al. (2003) *BBRC* 306:948-953.
[71] Bhagat et al. (2003) *BBRC* 300:853-861.
[72] WO03/035836.
[73] WO95/17211.
[74] WO98/42375.
[75] Beignon et al. (2002) *Infect Immun* 70:3012-3019.
[76] Pizza et al. (2001) *Vaccine* 19:2534-2541.
[77] Pizza et al. (2000) *Int J Med Microbio/*290:455-461.
[78] Scharton-Kersten et al. (2000) *Infect Immun* 68:5306-5313.
[79] Ryan et al. (1999) *Infect Immun* 67:6270-6280.
[80] Partidos et al. (1999) *Immunol Lett* 67:209-216.
[81] Peppoloni et al. (2003) *Expert Rev Vaccines* 2:285-293.
[82] Pine et al. (2002) *J Control Release* 85:263-270.
[83] Domenighini et al. (1995) *Mol Microbiol* 15:1165-1167.
[84] WO99/40936.
[85] WO99/44636.
[86] Singh et al] (2001) *J Cont Release* 70:267-276.
[87] WO99/27960.
[88] U.S. Pat. No. 6,090,406
[89] U.S. Pat. No. 5,916,588
[90] EP-A-0626169.
[91] WO99/52549.
[92] WO01/21207.
[93] WO01/21152.
[94] Andrianov et al. (1998) *Biomaterials* 19:109-115.
[95] Payne et al. (1998) *Adv Drug Delivery Review* 31:185-196.
[96] Stanley (2002) *Clin Exp Dermatol* 27:571-577.
[97] Jones (2003) *Curr Opin Investig Drugs* 4:214-218.
[98] WO99/11241.
[99] WO94/00153.
[100] WO98/57659.
[101] European patent applications 0835318, 0735898 and 0761231.
[102] WO03/009869.
[103] *W.H.O. Tech. Rep. Ser.* 594:51, 1976.
[104] Almeida & Alpar (1996) *J. Drug Targeting* 3:455-467.
[105] Agarwal & Mishra (1999) *Indian J Exp Biol* 37:6-16.
[106] Costantino et al. (1992) *Vaccine* 10:691-698.
[107] Costantino et al. (1999) *Vaccine* 17:1251-1263.
[108] WO03/007985.
[109] Watson (2000) *Pediatr Infect Dis* 119:331-332.
[110] Rubin (2000) *Pediatr Clin North Am* 47:269-285, v.
[111] Jedrzejas (2001) *Microbiol Mol Biol Rev* 65:187-207.
[112] Bell (2000) *Pediatr Infect Dis J* 19:1187-1188.
[113] Iwarson (1995) *APMIS* 103:321-326.
[114] Gerlich et al. (1990) *Vaccine* 8 Suppl:S63-68 & 79-80.
[115] Vaccines (1988) eds. Plotkin & Mortimer. ISBN 0-7216-1946-0.
[116] Del Guidice et al. (1998) *Molecular Aspects of Medicine* 19:1-70.
[117] Gustafsson et al. (1996) *N. Engl. J. Med.* 334:349-355.
[118] Rappuoli et al. (1991) *TIBTECH* 9:232-238.
[119] Sutter et al. (2000) *Pediatr Clin North Am* 47:287-308.
[120] Zimmerman & Spann (1999) *Am Fain Physician* 59:113-118, 125-126.
[121] McMichael (2000) *Vaccine* 19 Suppl 1:S101-107.
[122] Schuchat (1999) *Lancet* 353(9146):51-6.
[123] WO02/34771.
[124] Dale (1999) *Infect Dis Clin North Am* 13:227-43, viii.
[125] Ferretti et al. (2001) *PNAS USA* 98: 4658-4663.
[126] Kuroda et al. (2001) *Lancet* 357(9264):1225-1240; see also pages 1218-1219.
[127] EP-A-0372501
[128] EP-A-0378881
[129] EP-A-0427347
[130] WO93/17712
[131] WO94/03208
[132] WO98/58668
[133] EP-A-0471177
[134] WO00/56360
[135] WO91/01146
[136] WO00/61761
[137] WO01/72337
[138*] Research Disclosure,* 453077 (January 2002)
[139] Needleman& Wunsch (1970) *J. Mol. Biol.* 48, 443-453.
[140] Rice et al. (2000) *Trends Genet* 16:276-277.
[141] Gennaro (2000) *Remington: The Science and Practice of Pharmacy.* 20th edition, ISBN: 0683306472.
[142*] Methods In Enzymology* (S. Colowick and N. Kaplan, eds., Academic Press, Inc.)
[143*] Handbook of Experimental Immunology*, Vols. I-IV (D. M. Weir and C. C. Blackwell, eds., 1986, Blackwell Scientific Publications)
[144] Sambrook, et al., *Molecular Cloning: A Laboratory Manual* (2nd Edition, 1989).
[145*] Handbook of Surface and Colloidal Chemistry* (Birdi, K. S. ed., CRC Press, 1997)
[146*] Short Protocols in Molecular Biology,* 4th ed. (Ausubel et al. eds., 1999, John Wiley & Sons)
[147*] Molecular Biology Techniques: An Intensive Laboratory Course*, (Ream et al., eds., 1998, Academic Press)
[148*] PCR* (*Introduction to Biotechniques Series*), 2nd ed. (Newton & Graham eds., 1997, Springer Verlag)

What is claimed is:

1. A polypeptide comprising an amino acid sequence that has at least 90% sequence identity to SEQ ID NO: 38.

2. The polypeptide of claim 1, wherein the amino acid sequence has at least 95% sequence identity to SEQ ID NO: 38.

3. A polypeptide comprising a fragment of SEQ ID NO: 38, wherein the fragment of SEQ ID NO: 38 comprises at least 60 consecutive amino acids of the amino acid sequence of SEQ ID NO: 38.

4. The polypeptide of claim 3, wherein the fragment comprises a T-cell or a B-cell epitope from the SEQ ID NO: amino acid sequence.

5. A composition comprising: (a) the polypeptide of claim 3; and (b) a pharmaceutically acceptable carrier.

6. The composition of claim 5, further comprising an adjuvant.

7. A method of inducing an immune response in a subject, comprising administering to the subject a therapeutically effective amount of the composition of claim 5.

8. A method of inducing an immune response in a subject, comprising administering to the subject the composition of claim 5.

* * * * *

SEQUENCE LISTING

<160> NUMBER OF SEQ ID NOS: 78

<210> SEQ ID NO 1
<211> LENGTH: 1767
<212> TYPE: DNA
<213> ORGANISM: Neisseria meningitidis
<220> FEATURE:

-continued

```
<221> NAME/KEY: misc_feature
<222> LOCATION: 1744, 1745, 1746, 1747, 1748
<223> OTHER INFORMATION: n = A,T,C or G

<400> SEQUENCE: 1

atgaacgcgc aaaatctgcc tgaggtaaag tgggggcagg actatagaaa attggcgcaa     60

aaaagcaatg aacgccaatt tacccatacg actaattttt acaccaaaaa aaacgtaagt    120

ttatcattca ataataccga tgaagttgtt gctaaaaaaa acggtactgt cgttttcggc    180

gcggcgacct acctgccgcc ctacggcaag gtttccggtt ttgatgacaa aaggctgaaa    240

gagcgcggca atgccgttaa ttggattcat acgaccgacc cagggttggt aggctacagc    300

tacgaagatg ttacatgcaa cagcggcaac tgtcctgaag ttagctataa aacccaattt    360

atcttcgata atcaccagtt ggcaaaaaag aaaacagaca gcaagctgga tatatacgaa    420

gacaaaagcc gcgacaattc gcccatttac aaattgcagg attatccttg gttgggcgtg    480

tctttcaatt tgggcggaga gagctccttc aaaccaaaga gacaaggttc tttggtatct    540

tcttttagcg aggatgtgac gcagcaaaat ggtacacaag accaatacaa aggcaaaaac    600

ctcgtttata cgacagaaga ttacaataat cagggtaatc gtaaccatca ggacaaacac    660

cacgccatcg ccttttatct gaacgccaaa ctgcacctgc tggacaaaaa agggattaaa    720

gatatcaccg acaaaacagt gcagttgggt gtcttgaaac cgcgcatcga tttgacggaa    780

gcgtggaaaa acaggcatgg gagctttttt ggtaatggta attggacgtt tgaagataaa    840

ggagcagtca gcgtcaaact tatcttgccg gaagtcaaag caggccgctg catcaataaa    900

ccgaacccca atcccaaagc ccaagccctt tcccccgcac tgactgcccc cgcgctgtgg    960

ttcggacctg tgcaaaatgg taagatggag atgtattccg cttcggtttc tacctacccc   1020

gacagttcga gcagccgcat cttccttcaa aatctgaaaa gaaaaaacga ccccaacaaa   1080

cccggccgct attccctcgc agacttgagc gcgtcggaga ttaaaagtaa agagccgact   1140

ttcacagggc ggcaaaccgt catccgattg gataaaggcg tacatcagat caaacttaaa   1200

ggcaatgagg tcgaaggttt taagggaaac aacggcaacg acactttcgg cattgttagt   1260

gaagggagct tcatgcctga tgacagcgag tggaaaaaag tgctgctgcc ttggacggtt   1320

cgtgctttca atgatgacgg tcaatttaac acagtcaaca aagaagaaaa caacggcaag   1380

ccaaaataca gtcaaaaata ccgcagccgc aacaacggca agcacgagcg caatttgggc   1440

gacatcgtca acagccccat cgtggcggtc ggcgagtatt tggctacttc cgccaacgac   1500

gggatggtgc atatcttcaa aaaaagcggc ggggatgacc gcaactatag tctgaagctc   1560

agttatatcc cgggcacgat gccgcgcaag gatattcaaa gccaagactc caccccttgcc   1620

aaagagctgc gcgcctttgc cgaaaaaagc tatgtgggcg accgctacgg cgtggacggc   1680

ggctttgtct tgcgccaagt cgaatggaaa gggcaaaacc gcgtgtttat gttcggcgcg   1740

atgnnnnnca cacacttaat taattaa                                       1767


<210> SEQ ID NO 2
<211> LENGTH: 588
<212> TYPE: PRT
<213> ORGANISM: Neisseria meningitidis
<220> FEATURE:
<221> NAME/KEY: VARIANT
<222> LOCATION: 582, 583
<223> OTHER INFORMATION: Xaa = Any Amino Acid

<400> SEQUENCE: 2

Met Asn Ala Gln Asn Leu Pro Glu Val Lys Trp Gly Gln Asp Tyr Arg
 1               5                  10                  15
```

-continued

```
Lys Leu Ala Gln Lys Ser Asn Glu Arg Gln Phe Thr His Thr Thr Asn
            20                  25                  30

Phe Tyr Thr Lys Lys Asn Val Ser Leu Ser Phe Asn Asn Thr Asp Glu
        35                  40                  45

Val Val Ala Lys Lys Asn Gly Thr Val Val Phe Gly Ala Ala Thr Tyr
    50                  55                  60

Leu Pro Pro Tyr Gly Lys Val Ser Gly Phe Asp Asp Lys Arg Leu Lys
65                  70                  75                  80

Glu Arg Gly Asn Ala Val Asn Trp Ile His Thr Thr Asp Pro Gly Leu
                85                  90                  95

Val Gly Tyr Ser Tyr Glu Asp Val Thr Cys Asn Ser Gly Asn Cys Pro
            100                 105                 110

Glu Val Ser Tyr Lys Thr Gln Phe Ile Phe Asp Asn His Gln Leu Ala
        115                 120                 125

Lys Lys Lys Thr Asp Ser Lys Leu Asp Ile Tyr Glu Asp Lys Ser Arg
    130                 135                 140

Asp Asn Ser Pro Ile Tyr Lys Leu Gln Asp Tyr Pro Trp Leu Gly Val
145                 150                 155                 160

Ser Phe Asn Leu Gly Gly Glu Ser Ser Phe Lys Pro Lys Arg Gln Gly
                165                 170                 175

Ser Leu Val Ser Ser Phe Ser Glu Asp Val Thr Gln Gln Asn Gly Thr
            180                 185                 190

Gln Asp Gln Tyr Lys Gly Lys Asn Leu Val Tyr Thr Thr Glu Asp Tyr
        195                 200                 205

Asn Asn Gln Gly Asn Arg Asn His Gln Asp Lys His His Ala Ile Ala
    210                 215                 220

Phe Tyr Leu Asn Ala Lys Leu His Leu Leu Asp Lys Lys Gly Ile Lys
225                 230                 235                 240

Asp Ile Thr Asp Lys Thr Val Gln Leu Gly Val Leu Lys Pro Arg Ile
                245                 250                 255

Asp Leu Thr Glu Ala Trp Lys Asn Arg His Gly Ser Phe Phe Gly Asn
            260                 265                 270

Gly Asn Trp Thr Phe Glu Asp Lys Gly Ala Val Ser Val Lys Leu Ile
        275                 280                 285

Leu Pro Glu Val Lys Ala Gly Arg Cys Ile Asn Lys Pro Asn Pro Asn
    290                 295                 300

Pro Lys Ala Gln Ala Leu Ser Pro Ala Leu Thr Ala Pro Ala Leu Trp
305                 310                 315                 320

Phe Gly Pro Val Gln Asn Gly Lys Met Glu Met Tyr Ser Ala Ser Val
                325                 330                 335

Ser Thr Tyr Pro Asp Ser Ser Ser Ser Arg Ile Phe Leu Gln Asn Leu
            340                 345                 350

Lys Arg Lys Asn Asp Pro Asn Lys Pro Gly Arg Tyr Ser Leu Ala Asp
        355                 360                 365

Leu Ser Ala Ser Glu Ile Lys Ser Lys Glu Pro Thr Phe Thr Gly Arg
    370                 375                 380

Gln Thr Val Ile Arg Leu Asp Lys Gly Val His Gln Ile Lys Leu Lys
385                 390                 395                 400

Gly Asn Glu Val Glu Gly Phe Lys Gly Asn Asn Gly Asn Asp Thr Phe
                405                 410                 415

Gly Ile Val Ser Glu Gly Ser Phe Met Pro Asp Asp Ser Glu Trp Lys
            420                 425                 430

Lys Val Leu Leu Pro Trp Thr Val Arg Ala Phe Asn Asp Asp Gly Gln
```

-continued

```
        435                 440                 445

Phe Asn Thr Val Asn Lys Glu Glu Asn Asn Gly Lys Pro Lys Tyr Ser
    450                 455                 460

Gln Lys Tyr Arg Ser Arg Asn Asn Gly Lys His Glu Arg Asn Leu Gly
465                 470                 475                 480

Asp Ile Val Asn Ser Pro Ile Val Ala Val Gly Glu Tyr Leu Ala Thr
                485                 490                 495

Ser Ala Asn Asp Gly Met Val His Ile Phe Lys Lys Ser Gly Gly Asp
            500                 505                 510

Asp Arg Asn Tyr Ser Leu Lys Leu Ser Tyr Ile Pro Gly Thr Met Pro
        515                 520                 525

Arg Lys Asp Ile Gln Ser Gln Asp Ser Thr Leu Ala Lys Glu Leu Arg
    530                 535                 540

Ala Phe Ala Glu Lys Ser Tyr Val Gly Asp Arg Tyr Gly Val Asp Gly
545                 550                 555                 560

Gly Phe Val Leu Arg Gln Val Glu Trp Lys Gly Gln Asn Arg Val Phe
                565                 570                 575

Met Phe Gly Ala Met Xaa Xaa Thr His Leu Ile Asn
            580                 585


<210> SEQ ID NO 3
<211> LENGTH: 963
<212> TYPE: DNA
<213> ORGANISM: Neisseria meningitidis

<400> SEQUENCE: 3

atgcaagcac ggctgctgat acctattctt ttttcagttt ttattttatc cgcctgcggg      60

acactgacag gtattccatc gcatggcgga ggtaaacgct ttgcggtcga acaagaactt     120

gtggccgctt ctgccagagc tgccgttaaa gacatggatt tacaggcatt acacggacga     180

aaagttgcat tgtacattgc aactatgggc gaccaaggtt caggcagttt gacagggggt     240

cgctactcca ttgatgcact gattcgtggc gaatacataa acagccctgc cgtccgtacc     300

gattacacct atccacgtta cgaaaccacc gctgaaacaa catcaggcgg tttgacaggt     360

ttaaccactt ctttatctac acttaatgcc cctgcactct cgcgcaccca atcagacggt     420

agcggaagta aaagcagtct gggcttaaat attggcggga tgggggatta tcgaaatgaa     480

accttgacga ctaacccgcg cgacactgcc tttctttccc acttggtaca gaccgtattt     540

ttcctgcgcg gcatagacgt tgtttctcct gccaatgccg atacggatgt gtttattaac     600

atcgacgtat tcggaacgat acgcaacaga accgaaatgc acctatacaa tgccgaaaca     660

ctgaaagccc aaacaaaact ggaatatttc gcagtagaca gaaccaataa aaaattgctc     720

atcaaaccaa aaaccaatgc gtttgaagct gcctataaag aaaattacgc attgtggatg     780

ggaccgtata aagtaagcaa aggaattaaa ccgacagaag gattaatggt cgatttctcc     840

gatatccaac catacggcaa tcatatgggt aactctgccc catccgtaga ggctgataac     900

agtcatgagg ggtatggata cagcgatgaa gcagtgcgac gacatagaca agggcaacct     960

tga                                                                   963


<210> SEQ ID NO 4
<211> LENGTH: 320
<212> TYPE: PRT
<213> ORGANISM: Neisseria meningitidis

<400> SEQUENCE: 4

Met Gln Ala Arg Leu Leu Ile Pro Ile Leu Phe Ser Val Phe Ile Leu
```

-continued

```
1               5                   10                  15

Ser Ala Cys Gly Thr Leu Thr Gly Ile Pro Ser His Gly Gly Gly Lys
            20                  25                  30

Arg Phe Ala Val Glu Gln Glu Leu Val Ala Ala Ser Ala Arg Ala Ala
        35                  40                  45

Val Lys Asp Met Asp Leu Gln Ala Leu His Gly Arg Lys Val Ala Leu
    50                  55                  60

Tyr Ile Ala Thr Met Gly Asp Gln Gly Ser Gly Ser Leu Thr Gly Gly
65                  70                  75                  80

Arg Tyr Ser Ile Asp Ala Leu Ile Arg Gly Glu Tyr Ile Asn Ser Pro
                85                  90                  95

Ala Val Arg Thr Asp Tyr Thr Tyr Pro Arg Tyr Glu Thr Thr Ala Glu
            100                 105                 110

Thr Thr Ser Gly Gly Leu Thr Gly Leu Thr Thr Ser Leu Ser Thr Leu
        115                 120                 125

Asn Ala Pro Ala Leu Ser Arg Thr Gln Ser Asp Gly Ser Gly Ser Lys
    130                 135                 140

Ser Ser Leu Gly Leu Asn Ile Gly Gly Met Gly Asp Tyr Arg Asn Glu
145                 150                 155                 160

Thr Leu Thr Thr Asn Pro Arg Asp Thr Ala Phe Leu Ser His Leu Val
                165                 170                 175

Gln Thr Val Phe Phe Leu Arg Gly Ile Asp Val Val Ser Pro Ala Asn
            180                 185                 190

Ala Asp Thr Asp Val Phe Ile Asn Ile Asp Val Phe Gly Thr Ile Arg
        195                 200                 205

Asn Arg Thr Glu Met His Leu Tyr Asn Ala Glu Thr Leu Lys Ala Gln
    210                 215                 220

Thr Lys Leu Glu Tyr Phe Ala Val Asp Arg Thr Asn Lys Lys Leu Leu
225                 230                 235                 240

Ile Lys Pro Lys Thr Asn Ala Phe Glu Ala Ala Tyr Lys Glu Asn Tyr
                245                 250                 255

Ala Leu Trp Met Gly Pro Tyr Lys Val Ser Lys Gly Ile Lys Pro Thr
            260                 265                 270

Glu Gly Leu Met Val Asp Phe Ser Asp Ile Gln Pro Tyr Gly Asn His
        275                 280                 285

Met Gly Asn Ser Ala Pro Ser Val Glu Ala Asp Asn Ser His Glu Gly
    290                 295                 300

Tyr Gly Tyr Ser Asp Glu Ala Val Arg Arg His Arg Gln Gly Gln Pro
305                 310                 315                 320
```

<210> SEQ ID NO 5
<211> LENGTH: 1164
<212> TYPE: DNA
<213> ORGANISM: Neisseria meningitidis

<400> SEQUENCE: 5

```
gtgcatatta acttttcaat ggaatataaa gaatttaatg aaaattattt atataaaaag     60

ccgtttattt ttaaaaaagc tttagacgta agttctatct catggaaaga aattaatgag    120

ttgtatcaac gtgcagaccc tactgattgg caatttaaat ttcgcaaagg ggaaataatc    180

cccaaagaag cctatgttga atcattcaat gatgtgggta gaatacgtca tcggtttaat    240

aaaacagccg tatatcagta tctgcaagat ggtgcaacaa tggtttataa ccgtattgat    300

aatgagccat ttgttgacag tattgctaaa caaattgccc agtttgctca agcacaaact    360

gttgttagtg gttatttggc gtttggtagt tctccatcat atcgtaatca ttgggatact    420
```

```
cgtgatgtgt ttgcggttca attgattggc aaaaaacact ggacagtttc tgctccaaat    480

tttgatatgc cattgtatat gcagcaagca aaagatatgc cgcacattac tccgcctaca    540

acagtagata tggaagtcat tttagaagca ggagatattt tatatatccc gcgtggttgg    600

tggcataatc ctatgcctat gaattgtgaa acattccatt tagctattgg aacttttccg    660

ccaaatggtt ataattatat ggaatggttg atgaaaaaaa tacctgatat ccagagtatt    720

cgtcaaaatt tcatagactg ggaacacgac caaaaaaata tagataatgc ggctcaggca    780

gttactgaaa tgatgaagaa ccaagaaaat tatcaagcat tcatacaaga tttttggga    840

aatcaacgcg taaatactgc atttaatatg caaatttttg gaaatctgga taatgacaga    900

ttacctgaaa atagtacaat taaactcaat tcgttggata accgtacaat taaacaagga    960

tatatcatag cgaatggcat caaaaccaac ttggacaatg atagccaaac gatttgcaa   1020

tggattgctg acaaacatag tgttaagtta actcaactgt atgaattttg ccaaaatcaa   1080

aacattaatt tggaaaaagt ggaaaaatta gtgtttgatt tgacaatgat cgatgtattg   1140

gaatgtttaa ctgatgaaag ataa                                          1164
```

<210> SEQ ID NO 6
<211> LENGTH: 387
<212> TYPE: PRT
<213> ORGANISM: Neisseria meningitidis

<400> SEQUENCE: 6

```
Met His Ile Asn Phe Ser Met Glu Tyr Lys Glu Phe Asn Glu Asn Tyr
1               5                   10                  15

Leu Tyr Lys Lys Pro Phe Ile Phe Lys Lys Ala Leu Asp Val Ser Ser
            20                  25                  30

Ile Ser Trp Lys Glu Ile Asn Glu Leu Tyr Gln Arg Ala Asp Pro Thr
        35                  40                  45

Asp Trp Gln Phe Lys Phe Arg Lys Gly Glu Ile Ile Pro Lys Glu Ala
    50                  55                  60

Tyr Val Glu Ser Phe Asn Asp Val Gly Arg Ile Arg His Arg Phe Asn
65                  70                  75                  80

Lys Thr Ala Val Tyr Gln Tyr Leu Gln Asp Gly Ala Thr Met Val Tyr
                85                  90                  95

Asn Arg Ile Asp Asn Glu Pro Phe Val Asp Ser Ile Ala Lys Gln Ile
            100                 105                 110

Ala Gln Phe Ala Gln Ala Gln Thr Val Val Ser Gly Tyr Leu Ala Phe
        115                 120                 125

Gly Ser Ser Pro Ser Tyr Arg Asn His Trp Asp Thr Arg Asp Val Phe
    130                 135                 140

Ala Val Gln Leu Ile Gly Lys Lys His Trp Thr Val Ser Ala Pro Asn
145                 150                 155                 160

Phe Asp Met Pro Leu Tyr Met Gln Gln Ala Lys Asp Met Pro His Ile
                165                 170                 175

Thr Pro Pro Thr Thr Val Asp Met Glu Val Ile Leu Glu Ala Gly Asp
            180                 185                 190

Ile Leu Tyr Ile Pro Arg Gly Trp Trp His Asn Pro Met Pro Met Asn
        195                 200                 205

Cys Glu Thr Phe His Leu Ala Ile Gly Thr Phe Pro Pro Asn Gly Tyr
    210                 215                 220

Asn Tyr Met Glu Trp Leu Met Lys Lys Ile Pro Asp Ile Gln Ser Ile
225                 230                 235                 240
```

-continued

```
Arg Gln Asn Phe Ile Asp Trp Glu His Asp Gln Lys Asn Ile Asp Asn
                245                 250                 255

Ala Ala Gln Ala Val Thr Glu Met Met Lys Asn Gln Glu Asn Tyr Gln
            260                 265                 270

Ala Phe Ile Gln Asp Phe Leu Gly Asn Gln Arg Val Asn Thr Ala Phe
        275                 280                 285

Asn Met Gln Ile Phe Gly Asn Leu Asp Asn Asp Arg Leu Pro Glu Asn
    290                 295                 300

Ser Thr Ile Lys Leu Asn Ser Leu Asp Asn Arg Thr Ile Lys Gln Gly
305                 310                 315                 320

Tyr Ile Ile Ala Asn Gly Ile Lys Thr Asn Leu Asp Asn Asp Ser Gln
                325                 330                 335

Thr Ile Leu Gln Trp Ile Ala Asp Lys His Ser Val Lys Leu Thr Gln
            340                 345                 350

Leu Tyr Glu Phe Cys Gln Asn Gln Asn Ile Asn Leu Glu Lys Val Glu
        355                 360                 365

Lys Leu Val Phe Asp Leu Thr Met Ile Asp Val Leu Glu Cys Leu Thr
    370                 375                 380

Asp Glu Arg
385
```

<210> SEQ ID NO 7
<211> LENGTH: 1263
<212> TYPE: DNA
<213> ORGANISM: Neisseria meningitidis

<400> SEQUENCE: 7

```
atgacattat ttcgccccga agtattccaa gctaaaaaaa atcgctggac agggcaaatt     60

gttttagtgc gtccttttc cttgcagttt ttaacatttt tcgcggtctc attagcggct    120

attttagttg ctttttaat ttttgggagc tataccaata aaaccaccgt aacaggacaa    180

cttttgccga caacaggggt agtacgcgta tattcgcagg atatgggggt tattgctcat    240

caacacgtta tgaatggcga ttttgtgaaa aaaggcgatg tgttatttac attatctact    300

tcacgaaatg acaataatgg cagcatacaa gcacgattac tcgccgaagc tgaattaaaa    360

aaatcactat cagaacaaga aattattatg aaaaaacgtg ttcatgcagc agaaaaaacc    420

gcacaagaaa acacggtaca ccgttttcag aaccaaatgc aacacgttag aaatcaaatt    480

atcatgcaag aaaaacgtat tgcgatttct gaaaaaatgt tagaaaaaca gcgttattta    540

gccaaaatgg acgcaatttc tgaattagaa aaaaatagtt atgaaattgc tttattggag    600

ctgaaagcag gtttagccgc ttaccaacga gaagcagata atcttgctcg ggaaataact    660

gtacagcaaa gcaatctaaa aatctgcct gaacagcaag ctactgaaat cagtcaatta    720

gaacgcgcag tatctgtcta tcaacaagaa atattggatt atcaacaacg taacgaacaa    780

actattcgcg caaccatatc aggctatgtc agttctatta acacggaaat tggtcagcag    840

gtagatacta acaaactatt gatgagtatc gtgccgaaag aaagtgaatt actggctaat    900

ttatatgtcc ctagtcgcgc aatcggtttt gtaaaaccaa atgacaaggt aattttgcgt    960

tatcaagcat atccttatca aaaattcgga cacgcagaag gacacgtcat ttctattgct   1020

caaacggcac taggggcgca agaatggaca aatttaggca atatttttac tcaaacagca   1080

caagtgaatg agcctgttta tttaatcaaa gtaaaactgg ataatcagca tattcgtata   1140

tatggcacgg agaagaaatt gcaaattggt atgatactag aagccgatat tttgcatgag   1200

aataaacggt tatatgaatg gatacttgac cctttgtatc aagtaatggg aaaaatatca   1260
```

```
tag                                                                    1263


<210> SEQ ID NO 8
<211> LENGTH: 420
<212> TYPE: PRT
<213> ORGANISM: Neisseria meningitidis

<400> SEQUENCE: 8

Met Thr Leu Phe Arg Pro Glu Val Phe Gln Ala Lys Lys Asn Arg Trp
 1               5                  10                  15

Thr Gly Gln Ile Val Leu Val Arg Pro Phe Ser Leu Gln Phe Leu Thr
            20                  25                  30

Phe Phe Ala Val Ser Leu Ala Ala Ile Leu Val Ala Phe Leu Ile Phe
        35                  40                  45

Gly Ser Tyr Thr Asn Lys Thr Thr Val Thr Gly Gln Leu Leu Pro Thr
    50                  55                  60

Thr Gly Val Val Arg Val Tyr Ser Gln Asp Met Gly Val Ile Ala His
65                  70                  75                  80

Gln His Val Met Asn Gly Asp Phe Val Lys Lys Gly Asp Val Leu Phe
                85                  90                  95

Thr Leu Ser Thr Ser Arg Asn Asp Asn Asn Gly Ser Ile Gln Ala Arg
            100                 105                 110

Leu Leu Ala Glu Ala Glu Leu Lys Lys Ser Leu Ser Glu Gln Glu Ile
        115                 120                 125

Ile Met Lys Lys Arg Val His Ala Ala Glu Lys Thr Ala Gln Glu Asn
    130                 135                 140

Thr Val His Arg Phe Gln Asn Gln Met Gln His Val Arg Asn Gln Ile
145                 150                 155                 160

Ile Met Gln Glu Lys Arg Ile Ala Ile Ser Glu Lys Met Leu Glu Lys
                165                 170                 175

Gln Arg Tyr Leu Ala Lys Met Asp Ala Ile Ser Glu Leu Glu Lys Asn
            180                 185                 190

Ser Tyr Glu Ile Ala Leu Leu Glu Leu Lys Ala Gly Leu Ala Ala Tyr
        195                 200                 205

Gln Arg Glu Ala Asp Asn Leu Ala Arg Glu Ile Thr Val Gln Gln Ser
    210                 215                 220

Asn Leu Lys Asn Leu Pro Glu Gln Gln Ala Thr Glu Ile Ser Gln Leu
225                 230                 235                 240

Glu Arg Ala Val Ser Val Tyr Gln Gln Glu Ile Leu Asp Tyr Gln Gln
                245                 250                 255

Arg Asn Glu Gln Thr Ile Arg Ala Thr Ile Ser Gly Tyr Val Ser Ser
            260                 265                 270

Ile Asn Thr Glu Ile Gly Gln Gln Val Asp Thr Asn Lys Leu Leu Met
        275                 280                 285

Ser Ile Val Pro Lys Glu Ser Glu Leu Leu Ala Asn Leu Tyr Val Pro
    290                 295                 300

Ser Arg Ala Ile Gly Phe Val Lys Pro Asn Asp Lys Val Ile Leu Arg
305                 310                 315                 320

Tyr Gln Ala Tyr Pro Tyr Gln Lys Phe Gly His Ala Glu Gly His Val
                325                 330                 335

Ile Ser Ile Ala Gln Thr Ala Leu Gly Ala Gln Glu Trp Thr Asn Leu
            340                 345                 350

Gly Asn Ile Phe Thr Gln Thr Ala Gln Val Asn Glu Pro Val Tyr Leu
        355                 360                 365

Ile Lys Val Lys Leu Asp Asn Gln His Ile Arg Ile Tyr Gly Thr Glu
```

-continued

```
    370                 375                 380

Lys Lys Leu Gln Ile Gly Met Ile Leu Glu Ala Asp Ile Leu His Glu
385                 390                 395                 400

Asn Lys Arg Leu Tyr Glu Trp Ile Leu Asp Pro Leu Tyr Gln Val Met
                405                 410                 415

Gly Lys Ile Ser
            420


<210> SEQ ID NO 9
<211> LENGTH: 2013
<212> TYPE: DNA
<213> ORGANISM: Neisseria meningitidis

<400> SEQUENCE: 9

ttggcgtgtt tggtatcggt attggggttt catggttttt atacggattt gcgccattta     60

agggcgcgtt tttctttgtc tcttaaaggc gcaacattgg cagatttggt acggtttgct    120

aatagcatga atttaactgc tcgagctgtt cggttggatt tagatgaatt ggtaaatttg    180

cgcttaccct gtattttaca ttgggattta aatcattttg tggtgttgca tgaagttcat    240

cgtaatcaca ttgtgattat gaaccctgct tcgggttggc aaaaagtgcg tatggaagaa    300

gtctcgcgct gttttacagg catagcgttg gagctattcc ctaacacgca atttgaagag    360

aaacacgaaa cgcgtaaaat tcgcatacta ccgatgttgc gcggtgtggt tggattaaaa    420

aggtctttat ttcagcttct gctgctggcg gcagtattac aggtgtttgc tttggcaagc    480

ccttttttta tgcaatgggt aatagatcat gccattgtat cggcagaccg tgatttattg    540

ctaacattgg cattgggttt tggtttgttg atgattgtgc agcagttggt gtcattgttg    600

caaacttggg caggtatgta tttgtctact tcattgaata tccaatggaa agccaacgta    660

ttccgccgct taatggattt acctgtttct tatttcacta aacgacactt gggcgatgtg    720

gtttcacgtt ttggctcggt ggatagtatt caaagtacgc tcacttctac tttctttgtg    780

ctggtactca acagcattat ggcagtattt acattagggt taatgtattt atacagccct    840

agtttaacgg ctgttgtatt ggttgtttta ctgatttata tcggtattcg ttgggtggca    900

tattatccgt tacgccatgc aaccgaagaa aatattgttc atgctgccaa gcaaagcagt    960

tatttcatgg aaaccatacg cggtattcaa accgttaaat tatttgataa aaatgcacaa   1020

cgtcatgcgg cttggctgaa cttatttgtt gatacaatca acacaggttt aacgacacaa   1080

aaactttccg caatgttcgg ttttgcgaac agcctttttgt ttggtatcgc taatatttta   1140

attgtgtatt ttggtgcggt ttctgtgttg gacggtgttt ttaccgttgg ggcgttaatg   1200

gcgtttatgt cctacaaaag tcagtttgag agtaaagcag gttcattgat tgaccagttt   1260

gtacaaatca aaatgctagg attgcacgcg gaacgcttgg cggatattgt gctagaaaaa   1320

acggaaaacg agcagaacaa cgatttcagg ctgcctaaaa atttagaaca ctttgatatt   1380

aaaatagaaa atatatcatt tcgctatgct gaaaatgaac catacatttt gcaagatttc   1440

agtttaatta tcaaacaagg aacagccatt gcttttgctg gacattcagg ctgtgggaaa   1500

tctacgctca ttcaaattct gacaggcagt ctgaaacctg aaagcggtca cgtgttacta   1560

ggcgagaatg atattcatgc gtttccacct gcatttatcc gcaaatggag cgcaagtgta   1620

atgcaagatg atgtgttatt tgctggctca atcgcagaaa acatcagttt ttttgatgat   1680

acgcccaata tggaaaaaat cgcattttgc gctcaaatgg cgaatattca tcatgaaatt   1740

gtcgctatgc ctatggcgta tgaaacctta attggtgaca tgggaagcgc attgagcggt   1800

gggcaaaagc agcgtattgt tctagctcgt gctttatatc gtgaacccaa aattttgttt   1860
```

```
ttagacgaag ccagtagcca tttggacatc aacaatgaac gtgtgattaa cgataatcta   1920

cgccaactca acattaccaa aatcatggtc gcgcatcgtc aggaaacttt aaatactgct   1980

gatagcgtag tttatttaga caaggtagcc tga                                2013


<210> SEQ ID NO 10
<211> LENGTH: 670
<212> TYPE: PRT
<213> ORGANISM: Neisseria meningitidis

<400> SEQUENCE: 10

Met Ala Cys Leu Val Ser Val Leu Gly Phe His Gly Phe Tyr Thr Asp
1               5                   10                  15

Leu Arg His Leu Arg Ala Arg Phe Ser Leu Ser Leu Lys Gly Ala Thr
            20                  25                  30

Leu Ala Asp Leu Val Arg Phe Ala Asn Ser Met Asn Leu Thr Ala Arg
        35                  40                  45

Ala Val Arg Leu Asp Leu Asp Glu Leu Val Asn Leu Arg Leu Pro Cys
    50                  55                  60

Ile Leu His Trp Asp Leu Asn His Phe Val Val Leu His Glu Val His
65                  70                  75                  80

Arg Asn His Ile Val Ile Met Asn Pro Ala Ser Gly Trp Gln Lys Val
                85                  90                  95

Arg Met Glu Glu Val Ser Arg Cys Phe Thr Gly Ile Ala Leu Glu Leu
            100                 105                 110

Phe Pro Asn Thr Gln Phe Glu Glu Lys His Glu Thr Arg Lys Ile Arg
        115                 120                 125

Ile Leu Pro Met Leu Arg Gly Val Val Gly Leu Lys Arg Ser Leu Phe
    130                 135                 140

Gln Leu Leu Leu Leu Ala Ala Val Leu Gln Val Phe Ala Leu Ala Ser
145                 150                 155                 160

Pro Phe Phe Met Gln Trp Val Ile Asp His Ala Ile Val Ser Ala Asp
                165                 170                 175

Arg Asp Leu Leu Leu Thr Leu Ala Leu Gly Phe Gly Leu Leu Met Ile
            180                 185                 190

Val Gln Gln Leu Val Ser Leu Leu Gln Thr Trp Ala Gly Met Tyr Leu
        195                 200                 205

Ser Thr Ser Leu Asn Ile Gln Trp Lys Ala Asn Val Phe Arg Arg Leu
    210                 215                 220

Met Asp Leu Pro Val Ser Tyr Phe Thr Lys Arg His Leu Gly Asp Val
225                 230                 235                 240

Val Ser Arg Phe Gly Ser Val Asp Ser Ile Gln Ser Thr Leu Thr Ser
                245                 250                 255

Thr Phe Phe Val Leu Val Leu Asn Ser Ile Met Ala Val Phe Thr Leu
            260                 265                 270

Gly Leu Met Tyr Leu Tyr Ser Pro Ser Leu Thr Ala Val Val Leu Val
        275                 280                 285

Val Leu Leu Ile Tyr Ile Gly Ile Arg Trp Val Ala Tyr Tyr Pro Leu
    290                 295                 300

Arg His Ala Thr Glu Glu Asn Ile Val His Ala Ala Lys Gln Ser Ser
305                 310                 315                 320

Tyr Phe Met Glu Thr Ile Arg Gly Ile Gln Thr Val Lys Leu Phe Asp
                325                 330                 335

Lys Asn Ala Gln Arg His Ala Ala Trp Leu Asn Leu Phe Val Asp Thr
            340                 345                 350
```

-continued

```
Ile Asn Thr Gly Leu Thr Thr Gln Lys Leu Ser Ala Met Phe Gly Phe
        355                 360                 365

Ala Asn Ser Leu Leu Phe Gly Ile Ala Asn Ile Leu Ile Val Tyr Phe
    370                 375                 380

Gly Ala Val Ser Val Leu Asp Gly Val Phe Thr Val Gly Ala Leu Met
385                 390                 395                 400

Ala Phe Met Ser Tyr Lys Ser Gln Phe Glu Ser Lys Ala Gly Ser Leu
                405                 410                 415

Ile Asp Gln Phe Val Gln Ile Lys Met Leu Gly Leu His Ala Glu Arg
            420                 425                 430

Leu Ala Asp Ile Val Leu Glu Lys Thr Glu Asn Glu Gln Asn Asn Asp
        435                 440                 445

Phe Arg Leu Pro Lys Asn Leu Glu His Phe Asp Ile Lys Ile Glu Asn
    450                 455                 460

Ile Ser Phe Arg Tyr Ala Glu Asn Glu Pro Tyr Ile Leu Gln Asp Phe
465                 470                 475                 480

Ser Leu Ile Ile Lys Gln Gly Thr Ala Ile Ala Phe Ala Gly His Ser
                485                 490                 495

Gly Cys Gly Lys Ser Thr Leu Ile Gln Ile Leu Thr Gly Ser Leu Lys
            500                 505                 510

Pro Glu Ser Gly His Val Leu Leu Gly Glu Asn Asp Ile His Ala Phe
        515                 520                 525

Pro Pro Ala Phe Ile Arg Lys Trp Ser Ala Ser Val Met Gln Asp Asp
    530                 535                 540

Val Leu Phe Ala Gly Ser Ile Ala Glu Asn Ile Ser Phe Phe Asp Asp
545                 550                 555                 560

Thr Pro Asn Met Glu Lys Ile Ala Phe Cys Ala Gln Met Ala Asn Ile
                565                 570                 575

His His Glu Ile Val Ala Met Pro Met Ala Tyr Glu Thr Leu Ile Gly
            580                 585                 590

Asp Met Gly Ser Ala Leu Ser Gly Gly Gln Lys Gln Arg Ile Val Leu
        595                 600                 605

Ala Arg Ala Leu Tyr Arg Glu Pro Lys Ile Leu Phe Leu Asp Glu Ala
    610                 615                 620

Ser Ser His Leu Asp Ile Asn Asn Glu Arg Val Ile Asn Asp Asn Leu
625                 630                 635                 640

Arg Gln Leu Asn Ile Thr Lys Ile Met Val Ala His Arg Gln Glu Thr
                645                 650                 655

Leu Asn Thr Ala Asp Ser Val Val Tyr Leu Asp Lys Val Ala
            660                 665                 670
```

```
<210> SEQ ID NO 11
<211> LENGTH: 996
<212> TYPE: DNA
<213> ORGANISM: Neisseria meningitidis
<220> FEATURE:
<221> NAME/KEY: misc_feature
<222> LOCATION: 981, 982, 983, 984, 985
<223> OTHER INFORMATION: n = A,T,C or G

<400> SEQUENCE: 11

atgaaaatca aagccctgat gattgccgcc gcattgctgg cagcagccga tgtccacgcc      60

gcaccgcaaa aggcaaaaac cgcatccgcc aaagctgcca aagctgccaa agctgccaaa     120

gctgccaaag ctgccaaagt tgccaaagtt gccaaagttg ccaaagttgc caaagttgcc     180

aaagttgcca aagttgccaa agttgccaaa gttgccaaag ttgccaaagt tgccaaagtt     240
```

```
gccaaagttg ccaaagttgc caaagttgcc gccacggcgc aaaaagaagc cgcacccgca    300

caacagcagg gcggtatccg cttttcagac ggcattgccg ccgttgccga caacgaagtc    360

atcacgcgcc gccggcttgc cgaagccgtt gccgaagcca aagccaacct gcccaaagac    420

gcgcagataa gcgaatccga gctgtcccga caggtgctga tgcagcttgt caaccaatcc    480

ctgattgtac aggcgggcaa acgccgcaac attcaagcaa gcgaagcgga aatcgatgcc    540

gtcgtcgcaa aaaatcccgc cctcaaaaac ctcagccccg cccaacgccg cgattttgcc    600

gacaacatca ttgccgaaaa agtccgccag caggcagtga tgcagaacag ccgagtgagc    660

gaagctgaaa tcgatgcctt cctcgagcag gcgcaaaaac aaggcatcac cctgcccgaa    720

ggcgcaccgt tgcgccaata ccgcgcccaa cacatcctga ttaaagccga cagcgaaaac    780

gccgccgtcg gcgcggaaag caccatccgc aaaatctacg gagaggcccg cagcggcaca    840

gacttttcca gcctagcgcg ccaatattcg caagacgcga gcgcgggcaa cggcggagat    900

ttgggctggt ttgccgacgg cgtgatggtt cccgcctttg aagaagccgt ccacgcgctc    960

aaacccggac aggtcggcgc nnnnncacac acttaa                             996
```

```
<210> SEQ ID NO 12
<211> LENGTH: 331
<212> TYPE: PRT
<213> ORGANISM: Neisseria meningitidis
<220> FEATURE:
<221> NAME/KEY: VARIANT
<222> LOCATION: 328, 329
<223> OTHER INFORMATION: Xaa = Any Amino Acid

<400> SEQUENCE: 12

Met Lys Ile Lys Ala Leu Met Ile Ala Ala Ala Leu Leu Ala Ala Ala
 1               5                  10                  15

Asp Val His Ala Ala Pro Gln Lys Ala Lys Thr Ala Ser Ala Lys Ala
            20                  25                  30

Ala Lys Ala Ala Lys Ala Ala Lys Ala Ala Lys Ala Ala Lys Val Ala
        35                  40                  45

Lys Val Ala Lys Val Ala Lys Val Ala Lys Val Ala Lys Val Ala Lys
    50                  55                  60

Val Ala Lys Val Ala Lys Val Ala Lys Val Ala Lys Val Ala Lys Val
65                  70                  75                  80

Ala Lys Val Ala Lys Val Ala Lys Val Ala Ala Thr Ala Gln Lys Glu
                85                  90                  95

Ala Ala Pro Ala Gln Gln Gln Gly Gly Ile Arg Phe Ser Asp Gly Ile
            100                 105                 110

Ala Ala Val Ala Asp Asn Glu Val Ile Thr Arg Arg Arg Leu Ala Glu
        115                 120                 125

Ala Val Ala Glu Ala Lys Ala Asn Leu Pro Lys Asp Ala Gln Ile Ser
    130                 135                 140

Glu Ser Glu Leu Ser Arg Gln Val Leu Met Gln Leu Val Asn Gln Ser
145                 150                 155                 160

Leu Ile Val Gln Ala Gly Lys Arg Arg Asn Ile Gln Ala Ser Glu Ala
                165                 170                 175

Glu Ile Asp Ala Val Val Ala Lys Asn Pro Ala Leu Lys Asn Leu Ser
            180                 185                 190

Pro Ala Gln Arg Arg Asp Phe Ala Asp Asn Ile Ile Ala Glu Lys Val
        195                 200                 205

Arg Gln Gln Ala Val Met Gln Asn Ser Arg Val Ser Glu Ala Glu Ile
    210                 215                 220
```

Asp Ala Phe Leu Glu Gln Ala Gln Lys Gln Gly Ile Thr Leu Pro Glu
225 230 235 240

Gly Ala Pro Leu Arg Gln Tyr Arg Ala Gln His Ile Leu Ile Lys Ala
245 250 255

Asp Ser Glu Asn Ala Ala Val Gly Ala Glu Ser Thr Ile Arg Lys Ile
260 265 270

Tyr Gly Glu Ala Arg Ser Gly Thr Asp Phe Ser Ser Leu Ala Arg Gln
275 280 285

Tyr Ser Gln Asp Ala Ser Ala Gly Asn Gly Gly Asp Leu Gly Trp Phe
290 295 300

Ala Asp Gly Val Met Val Pro Ala Phe Glu Glu Ala Val His Ala Leu
305 310 315 320

Lys Pro Gly Gln Val Gly Ala Xaa Xaa His Thr
325 330

<210> SEQ ID NO 13
<211> LENGTH: 630
<212> TYPE: DNA
<213> ORGANISM: Neisseria meningitidis

<400> SEQUENCE: 13
ttggtcaaaa cggcagacgg ctacaaagct attgcccgta tccgagccgg cgagagcgtc 60
ctctccaagg acgaggcaag cggaaaaatg ggatacaaac ccgttaccgc ccgatacggc 120
aatccgtatg aagaaaccgt ttacattaaa gtttcagacg gcatcggcaa cagccaaacc 180
ctgatttcca accgcatcca ctcgttttat tcgggcggca aatggattaa gacggaagat 240
ttgaaagcgg gaatcaggct gttatccgaa agcggcaaaa cccaaaccgt ccgcaacatc 300
gttgtcaaac caaaaccgct caaagcctac aatctgaccg ttgctgactg gcatacctac 360
ttcgtcaagg gcagtcaggc ggaaacggaa ggggtttggg ttcataatgc gtgtccgcct 420
aaaagaacag gaagctccaa gaatgaaaaa catggagatg gcggtcgaag tcaaatatca 480
gcagaatcac gaattgctga attaaaaaat aaaattattc ccggaatgca caaaaatgaa 540
cgattaaaga ttgagaaaac aatcagaaat attgcaaaaa atgccaatcg aaaagcaaaa 600
ggagaagagc atggtcgaca cggtcgttaa 630

<210> SEQ ID NO 14
<211> LENGTH: 209
<212> TYPE: PRT
<213> ORGANISM: Neisseria meningitidis

<400> SEQUENCE: 14

Met Val Lys Thr Ala Asp Gly Tyr Lys Ala Ile Ala Arg Ile Arg Ala
1 5 10 15

Gly Glu Ser Val Leu Ser Lys Asp Glu Ala Ser Gly Lys Met Gly Tyr
20 25 30

Lys Pro Val Thr Ala Arg Tyr Gly Asn Pro Tyr Glu Glu Thr Val Tyr
35 40 45

Ile Lys Val Ser Asp Gly Ile Gly Asn Ser Gln Thr Leu Ile Ser Asn
50 55 60

Arg Ile His Ser Phe Tyr Ser Gly Gly Lys Trp Ile Lys Thr Glu Asp
65 70 75 80

Leu Lys Ala Gly Ile Arg Leu Leu Ser Glu Ser Gly Lys Thr Gln Thr
85 90 95

Val Arg Asn Ile Val Val Lys Pro Lys Pro Leu Lys Ala Tyr Asn Leu
100 105 110

Thr Val Ala Asp Trp His Thr Tyr Phe Val Lys Gly Ser Gln Ala Glu
115 120 125

Thr Glu Gly Val Trp Val His Asn Ala Cys Pro Pro Lys Arg Thr Gly
130 135 140

Ser Ser Lys Asn Glu Lys His Gly Asp Gly Gly Arg Ser Gln Ile Ser
145 150 155 160

Ala Glu Ser Arg Ile Ala Glu Leu Lys Asn Lys Ile Ile Pro Gly Met
165 170 175

His Lys Asn Glu Arg Leu Lys Ile Glu Lys Thr Ile Arg Asn Ile Ala
180 185 190

Lys Asn Ala Asn Arg Lys Ala Lys Gly Glu Glu His Gly Arg His Gly
195 200 205

Arg

<210> SEQ ID NO 15
<211> LENGTH: 798
<212> TYPE: DNA
<213> ORGANISM: Neisseria meningitidis

<400> SEQUENCE: 15
atgaatccag cccccaaaaa accttctctt ctcttctctt ctcttctctt ctcttctctt 60
ctcttctctt ccgcagcgca ggcggcaagt gaagacagca gccgcagccc gtattatgtg 120
caggcggatt tagcctatgc cgccgaacgc attacccaca attatccgga accaaccggt 180
gcagacaaag acaaaataag cacagtaagc gattatttca gaaacatccg tgcgcattcc 240
atccaccctc gggtgtcggt cggctacgac ttcggcgact ggagaatagc ggcagattat 300
gccagttaca gaaaatggaa agaaagtaat tcttctacta atgcagaaaa tagagataat 360
gcaaaaaact acgtaaagat tgaaacaaaa catcaaggaa acggcagctt ccacgccgct 420
tcttctctcg gcttatccgc catttacgat ttcaaactca acgataaatt caaaccctat 480
atcggcgcgc gcgtcgccta cggacacgtt aaacatcagg ttcattcagt ggaaacaaaa 540
accacgactg ttacctctaa accgacggca acctctccac agggaggccc tattatacaa 600
actgatccca gcaaacctcc ctatcacgaa agccacagca tcagcagctt gggtcttggt 660
gtcatcgccg gtgtcggttt cgacatcacg cccaagctga ccttggacac cggataccgc 720
taccacaact ggggacgctt ggaaaacacc cgcttcaaaa cccacgaagt ctcattgggc 780
atgcgctacc acttctga 798

<210> SEQ ID NO 16
<211> LENGTH: 265
<212> TYPE: PRT
<213> ORGANISM: Neisseria meningitidis

<400> SEQUENCE: 16

Met Asn Pro Ala Pro Lys Lys Pro Ser Leu Leu Phe Ser Ser Leu Leu
1 5 10 15

Phe Ser Ser Leu Leu Phe Ser Ser Ala Ala Gln Ala Ala Ser Glu Asp
20 25 30

Ser Ser Arg Ser Pro Tyr Tyr Val Gln Ala Asp Leu Ala Tyr Ala Ala
35 40 45

Glu Arg Ile Thr His Asn Tyr Pro Glu Pro Thr Gly Ala Asp Lys Asp
50 55 60

Lys Ile Ser Thr Val Ser Asp Tyr Phe Arg Asn Ile Arg Ala His Ser
65 70 75 80

-continued

```
Ile His Pro Arg Val Ser Val Gly Tyr Asp Phe Gly Asp Trp Arg Ile
                85                  90                  95

Ala Ala Asp Tyr Ala Ser Tyr Arg Lys Trp Lys Glu Ser Asn Ser Ser
            100                 105                 110

Thr Asn Ala Glu Asn Arg Asp Asn Ala Lys Asn Tyr Val Lys Ile Glu
        115                 120                 125

Thr Lys His Gln Gly Asn Gly Ser Phe His Ala Ala Ser Ser Leu Gly
    130                 135                 140

Leu Ser Ala Ile Tyr Asp Phe Lys Leu Asn Asp Lys Phe Lys Pro Tyr
145                 150                 155                 160

Ile Gly Ala Arg Val Ala Tyr Gly His Val Lys His Gln Val His Ser
                165                 170                 175

Val Glu Thr Lys Thr Thr Thr Val Thr Ser Lys Pro Thr Ala Thr Ser
            180                 185                 190

Pro Gln Gly Gly Pro Ile Ile Gln Thr Asp Pro Ser Lys Pro Pro Tyr
        195                 200                 205

His Glu Ser His Ser Ile Ser Ser Leu Gly Leu Gly Val Ile Ala Gly
    210                 215                 220

Val Gly Phe Asp Ile Thr Pro Lys Leu Thr Leu Asp Thr Gly Tyr Arg
225                 230                 235                 240

Tyr His Asn Trp Gly Arg Leu Glu Asn Thr Arg Phe Lys Thr His Glu
                245                 250                 255

Val Ser Leu Gly Met Arg Tyr His Phe
            260                 265
```

<210> SEQ ID NO 17
<211> LENGTH: 2043
<212> TYPE: DNA
<213> ORGANISM: Neisseria meningitidis

<400> SEQUENCE: 17

```
atggtgctgc ctgtgttttt gttgagtgct tgtttgggcg gcggcggcag tttcgatctt     60

gattctgtcg ataccgaagc cccgcgtccc gcgccaaagt atcaagatgt ttcttccgaa    120

acaccgcaag cccaaaaaga ccaaggcgga tacggttttg caatgcgctt caagcggcgg    180

aattggcacc caaaaaataa agaagatcat aaggcattat cagaagcgga ttgggagaag    240

ttaggtgcgg gtaagccaga tgagtttccc caaaagaatg agatttcagc gatggataag    300

ggtacgctga acgaatccat cacgccgggc gacggcaaaa gccgtgctga aggctatacg    360

gatttccaat atgtccgctc gggctatatc taccgcaacg gtgtcaataa aatcgattac    420

caaaacaata ttgccctttc cggtccggac ggctaccttt tctacaaagg cagcaatcct    480

tctcaagctc tgccgacggg caaggcgatt tacaaaggta cttgggatta tgtaaccgat    540

gccaaggaaa aacagaagtt tccccagttg ggtagttttc aagcggggga taggtacggg    600

gctctgtctg ccgaggaaga ggatgtgttg cgcaacaaaa gcgaggcgaa ggaaggtcag    660

accgatttcg ggctgaccag cgagtttgag gtggacttcg ccgccaagac catgaccggc    720

aaactctacc gcaataaccg gattaccaat aacgaaaccg aaaatagaga caaacaaatt    780

aaacgttacg acattcaggc taacctgcac ggcaaccgct tcaacggcaa ggcaacggca    840

accgacaaac caaaagagaa tgaaaccaaa caacatccct ttgtttccga ctcgtcttct    900

ttgagcggcg gctttttcgg cccgcagggt gaggaattgg gtttccgctt tttgagcaac    960

gatcaaaaag ttgccgttgt cggcagcgcg aaaacccaag acaaagccgc aaatggcaat   1020

actgcggcgg cttcaggcga tgcaagcgtt tccgcatcaa acggtgcggc aggcacgtcg   1080
```

-continued

```
tctgaaaacg gtaagctgac cacggttttg gatgcggttg aattgacact aaacgacaag   1140

aaaatcaaaa atctcgacaa cttcagcaat gccgcccaac tggttgtcga cggcattatg   1200

attccgctcc tgcccgagac ttccgaaagt gggaacaatc aggcagataa aggtaaaaac   1260

ggcggaacag cctttacccg caaatttgac cacacgccga aaagcgatga aaaagacacc   1320

caagcaggca cggcggcgaa tggcgcgcaa accgcttcgg gtacggcagg cgacacaagt   1380

ggcaaaacaa aaacctatca agtcgaagtc tgctgttcca acctcaatta tctgaaatac   1440

ggaatgttga cacgcaaaaa cagcgaatcc gcgatgcagg caggcgaaag cagtagtcaa   1500

actcctgccg cccaaacggc acagggcgca caaagtatgt tcctccaagg cgagcgcacc   1560

gatgaaaaca agattccaac cgaccaaaac gtcgtttatc gggggtcttg gtacgggcat   1620

attgccagca gcacaagctg gagcggcaat gcttccaatg caacgagtgg caacagggcg   1680

gaatttactg tgaatttcga tacgaaaaaa attaccggca agttaaccgc tgaaaacagg   1740

caggaggcaa cctttaccat tgatggtaag attgagggca acggctttga aggtacggca   1800

aaaactgctg aattaggttt tgatctcgat caaagcaata ccaccggcac gcctaaggca   1860

tatatcacaa acgccaaggt gcagggcggt ttttacggac ctaaagccga agagttgggc   1920

ggatggtttg cctatccggg cgataaacaa acggaaaata caacagttgc atccggcaat   1980

ggaaattcag caagcagtgc aactgtcgta ttcggtgcga aacgccaaaa gcctgtgcaa   2040

taa                                                                 2043
```

<210> SEQ ID NO 18
<211> LENGTH: 680
<212> TYPE: PRT
<213> ORGANISM: Neisseria meningitidis

<400> SEQUENCE: 18

```
Met Val Leu Pro Val Phe Leu Leu Ser Ala Cys Leu Gly Gly Gly Gly
 1               5                  10                  15

Ser Phe Asp Leu Asp Ser Val Asp Thr Glu Ala Pro Arg Pro Ala Pro
            20                  25                  30

Lys Tyr Gln Asp Val Ser Ser Glu Thr Pro Gln Ala Gln Lys Asp Gln
        35                  40                  45

Gly Gly Tyr Gly Phe Ala Met Arg Phe Lys Arg Arg Asn Trp His Pro
    50                  55                  60

Lys Asn Lys Glu Asp His Lys Ala Leu Ser Glu Ala Asp Trp Glu Lys
65                  70                  75                  80

Leu Gly Ala Gly Lys Pro Asp Glu Phe Pro Gln Lys Asn Glu Ile Ser
                85                  90                  95

Ala Met Asp Lys Gly Thr Leu Asn Glu Ser Ile Thr Pro Gly Asp Gly
            100                 105                 110

Lys Ser Arg Ala Glu Gly Tyr Thr Asp Phe Gln Tyr Val Arg Ser Gly
        115                 120                 125

Tyr Ile Tyr Arg Asn Gly Val Asn Lys Ile Asp Tyr Gln Asn Asn Ile
    130                 135                 140

Ala Leu Ser Gly Pro Asp Gly Tyr Leu Phe Tyr Lys Gly Ser Asn Pro
145                 150                 155                 160

Ser Gln Ala Leu Pro Thr Gly Lys Ala Ile Tyr Lys Gly Thr Trp Asp
                165                 170                 175

Tyr Val Thr Asp Ala Lys Glu Lys Gln Lys Phe Pro Gln Leu Gly Ser
            180                 185                 190

Phe Gln Ala Gly Asp Arg Tyr Gly Ala Leu Ser Ala Glu Glu Glu Asp
        195                 200                 205
```

-continued

```
Val Leu Arg Asn Lys Ser Glu Ala Lys Glu Gly Gln Thr Asp Phe Gly
    210                 215                 220

Leu Thr Ser Glu Phe Glu Val Asp Phe Ala Ala Lys Thr Met Thr Gly
225                 230                 235                 240

Lys Leu Tyr Arg Asn Asn Arg Ile Thr Asn Asn Glu Thr Glu Asn Arg
                245                 250                 255

Asp Lys Gln Ile Lys Arg Tyr Asp Ile Gln Ala Asn Leu His Gly Asn
            260                 265                 270

Arg Phe Asn Gly Lys Ala Thr Ala Thr Asp Lys Pro Lys Glu Asn Glu
        275                 280                 285

Thr Lys Gln His Pro Phe Val Ser Asp Ser Ser Ser Leu Ser Gly Gly
    290                 295                 300

Phe Phe Gly Pro Gln Gly Glu Glu Leu Gly Phe Arg Phe Leu Ser Asn
305                 310                 315                 320

Asp Gln Lys Val Ala Val Val Gly Ser Ala Lys Thr Gln Asp Lys Ala
                325                 330                 335

Ala Asn Gly Asn Thr Ala Ala Ala Ser Gly Asp Ala Ser Val Ser Ala
            340                 345                 350

Ser Asn Gly Ala Ala Gly Thr Ser Ser Glu Asn Gly Lys Leu Thr Thr
        355                 360                 365

Val Leu Asp Ala Val Glu Leu Thr Leu Asn Asp Lys Lys Ile Lys Asn
    370                 375                 380

Leu Asp Asn Phe Ser Asn Ala Ala Gln Leu Val Val Asp Gly Ile Met
385                 390                 395                 400

Ile Pro Leu Leu Pro Glu Thr Ser Glu Ser Gly Asn Asn Gln Ala Asp
                405                 410                 415

Lys Gly Lys Asn Gly Gly Thr Ala Phe Thr Arg Lys Phe Asp His Thr
            420                 425                 430

Pro Lys Ser Asp Glu Lys Asp Thr Gln Ala Gly Thr Ala Ala Asn Gly
        435                 440                 445

Ala Gln Thr Ala Ser Gly Thr Ala Gly Asp Thr Ser Gly Lys Thr Lys
    450                 455                 460

Thr Tyr Gln Val Glu Val Cys Cys Ser Asn Leu Asn Tyr Leu Lys Tyr
465                 470                 475                 480

Gly Met Leu Thr Arg Lys Asn Ser Glu Ser Ala Met Gln Ala Gly Glu
                485                 490                 495

Ser Ser Ser Gln Thr Pro Ala Ala Gln Thr Ala Gln Gly Ala Gln Ser
            500                 505                 510

Met Phe Leu Gln Gly Glu Arg Thr Asp Glu Asn Lys Ile Pro Thr Asp
        515                 520                 525

Gln Asn Val Val Tyr Arg Gly Ser Trp Tyr Gly His Ile Ala Ser Ser
    530                 535                 540

Thr Ser Trp Ser Gly Asn Ala Ser Asn Ala Thr Ser Gly Asn Arg Ala
545                 550                 555                 560

Glu Phe Thr Val Asn Phe Asp Thr Lys Lys Ile Thr Gly Lys Leu Thr
                565                 570                 575

Ala Glu Asn Arg Gln Glu Ala Thr Phe Thr Ile Asp Gly Lys Ile Glu
            580                 585                 590

Gly Asn Gly Phe Glu Gly Thr Ala Lys Thr Ala Glu Leu Gly Phe Asp
        595                 600                 605

Leu Asp Gln Ser Asn Thr Thr Gly Thr Pro Lys Ala Tyr Ile Thr Asn
    610                 615                 620

Ala Lys Val Gln Gly Gly Phe Tyr Gly Pro Lys Ala Glu Glu Leu Gly
```

-continued

```
625                 630                 635                 640

Gly Trp Phe Ala Tyr Pro Gly Asp Lys Gln Thr Glu Asn Thr Thr Val
                645                 650                 655

Ala Ser Gly Asn Gly Asn Ser Ala Ser Ser Ala Thr Val Val Phe Gly
            660                 665                 670

Ala Lys Arg Gln Lys Pro Val Gln
        675                 680


<210> SEQ ID NO 19
<211> LENGTH: 4113
<212> TYPE: DNA
<213> ORGANISM: Neisseria meningitidis
<220> FEATURE:
<221> NAME/KEY: misc_feature
<222> LOCATION: 6, 7, 8, 9, 10, 4098, 4099, 4100, 4101, 4102
<223> OTHER INFORMATION: n = A,T,C or G

<400> SEQUENCE: 19

gtgtgnnnnn ctccgaatgg acgcggattg agccacaacc gctatacgca gtttgatgtt     60

gacaacaaag ggcagtgtt aaacaacgac cgtaacaata atccgtttct ggtcaaaggc    120

agtgcgcaat tgattttgaa cgaggtacgc ggtacggcta gcaaactcaa cggcatcgtt    180

accgtaggcg gtcaaaaggc cgacgtgatt attgccaacc ccaacggcat taccgttaat    240

ggcggcggct ttaaaaacgt cggccgcggt atcttaacca ccggtacgcc tcaaatcggc    300

aaagacggtg ccttgacggg atttgacgtg cgccaaggca cattgaccgt cggtacgtca    360

ggttggaacg acaaaggcgg agccgattac accgaagtgc ttgcccgtgc ggttgctttg    420

caggggaaat tgcagggtaa aaacctggcg gtttcgaccg gcgcacagaa agtagattac    480

gccagcggtg aaatcagcgc aggaacggca gcaggtacga aaccgaccgt tgccctcgat    540

actgccgcat tgggtggtat gtacgcagac agcattaccc tgattgccaa tgaaaaaggc    600

gtaggcgtca aaaatgccgg cacactcgaa gcggccaagc aattgattgt gacttcgtca    660

ggccgcattg aaaacagcgg ccgcatcgcc accactgccg acggcaccga agcttcaccg    720

acttatctct ccatcgaaac caccgaaaaa ggagcggcag gcacatttat ctccaatggt    780

ggtcggatcg agagcaaagg cttattggtt attgagacgg gagaagatat cagcttgcgt    840

aacggagccg tggtgcagaa taacggcagt cgcccagcta ccacggtatt aaatgctggt    900

cataatttgg tgattgagag taaaactaat gtgaacaatg ccaaaggctc ggctaatctg    960

tcggccggcg gtcgtactac gatcaatgat gctactattc aagcgggcag ttccgtgtac   1020

agctccacca aaggcgatac tgaattgggt gaaaataccc gtattattgc tgaaaacgta   1080

accgtattgt ccaacggcag tattggcagt gctgctgtaa ttgaggctaa agacactgca   1140

cacattgaag cgggtaaacc gctttcttta gagacttcaa acgttgcttc taacatccgt   1200

ttgaacaacg gtagcattaa aggcggaaag caggtggtat tgatggctga tgacgacatt   1260

caggcaaaag cctcccacct gaatgcgtcc ggcaatctgt atattcatgc aggtaaggat   1320

ctggatttga atgccgataa agacttatca acacaaagta tcagcctgag ggcagacaac   1380

accgccctca tcagcagcaa cggtaacacc ttgactgcag aaaagaatct ggatattcag   1440

gcaggtagct tgagtgtgcg tcaaagtaat ctgcaatcca gtggcggtaa tgtgcagatg   1500

agcgcgacta aaggcaacat cagcttgaat cagagttgga taaatgccag tcagaatatt   1560

gatacggcag cacttcaagg caatattatt tcagacggtc tgactgctgt tgccgaagtt   1620

ggacgcgtat ctcttcttgc caacggcaat gttgatttca acggtctaaa taccttgatt   1680

gcggaaggag acattaatgc tggttcagtc ggtaaaggcc gtctgaaaat ggacaatacc   1740
```

-continued

```
gatatttatg cttctgcagg cgatgtgaaa ctggttgccg gaggtcaatt agatttaggc   1800
aacggcaccg ttaacggcgg tcatatcagc ttagacagca ataaaggcag catggtggtg   1860
cagaatgtac acctgaatgc ccgcgcatca ctgaaagtgg atgcggatca aactttaacc   1920
attaataaca gcaagctcaa ttccgatcac aatacccaga ttaatacaaa tcatggtcat   1980
atgacgctta atcagcttga tgctcattca cgtcgtcata tgagtatcag tgcacagggt   2040
aaaggcaaag gaaaagacag cggtcaaatt ttacaaaacg accagcaaaa cagtaaaagt   2100
actttggcgg cagatggtgt attgtcattg aacagcagcg cattacaggt tttggacaat   2160
actaccctgc gcggtggcgc gataaacatc aaagctggcg gaggcatcat caaacggggg   2220
catatcgatt gggaaaccca agatacggca actatgcgtt cagcggaact gaaaccactg   2280
tccggtatga tgtcgataga atcgggcggt gataaccctt taaccgttga acccggtaac   2340
cgtatcgttt ctgcaggtga tttggccgtg aaccacaacg gcacattcca aatcagtgcc   2400
agagcaggaa ataacggcaa tccgagtgcg caaacagcca gcgtttcagc taaaggcaat   2460
atcgggattg tggcgggaga ggtggatatt gatgcagcaa atattgccgc agggaaagat   2520
ttggctttag tggcaactaa agggaatatt tcactaaaca gtattaggaa tacgtttagt   2580
aactatcaat tgaaaacaga taaacacaat atcacacagc aacttactga tgtagagcag   2640
gagcttagta agttaacgag cgatcctaaa tatcgtaaag cacaggatct ttcacaaatg   2700
ttgaggcgta aatataagag gcgtgacaaa gtattcggtg atagtgaggc cagattacgt   2760
ggtttacgag caaagataaa tgctgctgat gaggcttggg cagaacgcca atccccagta   2820
aaagcgttac ttgaacgtaa acaattgtta caacaagccc ttttaacagt ttcccaaccg   2880
ggtagtggtc acgaaaacca aggtagcacc cttagcggtc aaaatatcaa actgctcgct   2940
gcaggtggta tccgtatcca gggctccaaa gttgctgcca cccaacaggc aaatatccaa   3000
gctgcaggat ttttacctgc accagccgca gaggaactgc aagaaggtcg acttcaatca   3060
gccattgaca tcagcggtgt acttgatact tttgaatatg gtcagcaagg cagcgataaa   3120
tacggctatg ccattttcag caggccatct gaaatttcag gaaaaacagg tgttaccctc   3180
tctgcaccaa atgccaatga gaacagccgc atcagtctga gtgcggcaaa catcgaagct   3240
gaaaacggca aaatcaaaat tcaatcctac ggcgaccaat cctattacgc cggacagggc   3300
gaactctata cctttgaacg ccgcagctac aaaaccggca aatggtacaa ccgcaaacac   3360
attaccgaag tcaaagaaca caaaaacgcc aagcccgacg cagtaaacct cagcgcatcc   3420
caaggcatcg acatcaaatc tggtggcagc atcgacgcct acgccaccgc attcgatgcc   3480
cccaaaggca gcattaacat cgaagccggg cggaaattga cactctatgc cgtagaagag   3540
ctcaactacg acaaactaga cagccaaaaa aggcgcagat ttctcggcat cagctacagc   3600
aaagcacacg acaccaccac ccaagtcatg aaaaccgcgc tgccctcaag ggtagttgca   3660
gaatcagcca atctgcaatc aggttgggat accaaactgc aaggcacaca gtttgaaacc   3720
acactgggtg gcgcaaccat acgcgcaggc gtaggcgagc aggcacgggc agatgccaag   3780
attatcctcg aagggatcaa aagcagcatc cacacagaaa ccgtgagcag cagcaaatct   3840
actctatggc aaaaacaggc aggacggggc agtaacatcg aaaccttgca attgccgagt   3900
ttcaccggtc ccgttgcgcc cgtactgtcc gcacccggcg gttacattgt cgatattccc   3960
caaggcaatc tgaaaaccca aatcgaaacc ctcaccaaac agcccgagta tgcttatttg   4020
aacaacttca agttgcgaaa aacatcaact ggaatcacgt gcagcttgct tacgataaat   4080
gggactacaa acaggagnnn nncacacact taa                                4113
```

<210> SEQ ID NO 20
<211> LENGTH: 1370
<212> TYPE: PRT
<213> ORGANISM: Neisseria meningitidis
<220> FEATURE:
<221> NAME/KEY: VARIANT
<222> LOCATION: 2, 3, 4, 1366, 1367, 1368
<223> OTHER INFORMATION: Xaa = Any Amino Acid

<400> SEQUENCE: 20

```
Met Xaa Xaa Xaa Pro Asn Gly Arg Gly Leu Ser His Asn Arg Tyr Thr
 1              5                   10                  15

Gln Phe Asp Val Asp Asn Lys Gly Ala Val Leu Asn Asn Asp Arg Asn
            20                  25                  30

Asn Asn Pro Phe Leu Val Lys Gly Ser Ala Gln Leu Ile Leu Asn Glu
        35                  40                  45

Val Arg Gly Thr Ala Ser Lys Leu Asn Gly Ile Val Thr Val Gly Gly
    50                  55                  60

Gln Lys Ala Asp Val Ile Ile Ala Asn Pro Asn Gly Ile Thr Val Asn
65                  70                  75                  80

Gly Gly Gly Phe Lys Asn Val Gly Arg Gly Ile Leu Thr Thr Gly Thr
                85                  90                  95

Pro Gln Ile Gly Lys Asp Gly Ala Leu Thr Gly Phe Asp Val Arg Gln
            100                 105                 110

Gly Thr Leu Thr Val Gly Thr Ser Gly Trp Asn Asp Lys Gly Gly Ala
        115                 120                 125

Asp Tyr Thr Glu Val Leu Ala Arg Ala Val Ala Leu Gln Gly Lys Leu
    130                 135                 140

Gln Gly Lys Asn Leu Ala Val Ser Thr Gly Ala Gln Lys Val Asp Tyr
145                 150                 155                 160

Ala Ser Gly Glu Ile Ser Ala Gly Thr Ala Ala Gly Thr Lys Pro Thr
                165                 170                 175

Val Ala Leu Asp Thr Ala Ala Leu Gly Gly Met Tyr Ala Asp Ser Ile
            180                 185                 190

Thr Leu Ile Ala Asn Glu Lys Gly Val Gly Val Lys Asn Ala Gly Thr
        195                 200                 205

Leu Glu Ala Ala Lys Gln Leu Ile Val Thr Ser Ser Gly Arg Ile Glu
    210                 215                 220

Asn Ser Gly Arg Ile Ala Thr Thr Ala Asp Gly Thr Glu Ala Ser Pro
225                 230                 235                 240

Thr Tyr Leu Ser Ile Glu Thr Thr Glu Lys Gly Ala Ala Gly Thr Phe
                245                 250                 255

Ile Ser Asn Gly Gly Arg Ile Glu Ser Lys Gly Leu Leu Val Ile Glu
            260                 265                 270

Thr Gly Glu Asp Ile Ser Leu Arg Asn Gly Ala Val Val Gln Asn Asn
        275                 280                 285

Gly Ser Arg Pro Ala Thr Thr Val Leu Asn Ala Gly His Asn Leu Val
    290                 295                 300

Ile Glu Ser Lys Thr Asn Val Asn Asn Ala Lys Gly Ser Ala Asn Leu
305                 310                 315                 320

Ser Ala Gly Gly Arg Thr Thr Ile Asn Asp Ala Thr Ile Gln Ala Gly
                325                 330                 335

Ser Ser Val Tyr Ser Ser Thr Lys Gly Asp Thr Glu Leu Gly Glu Asn
            340                 345                 350

Thr Arg Ile Ile Ala Glu Asn Val Thr Val Leu Ser Asn Gly Ser Ile
```

-continued

```
        355                 360                 365

Gly Ser Ala Ala Val Ile Glu Ala Lys Asp Thr Ala His Ile Glu Ala
    370                 375                 380

Gly Lys Pro Leu Ser Leu Glu Thr Ser Asn Val Ala Ser Asn Ile Arg
385                 390                 395                 400

Leu Asn Asn Gly Ser Ile Lys Gly Gly Lys Gln Val Val Leu Met Ala
                405                 410                 415

Asp Asp Asp Ile Gln Ala Lys Ala Ser His Leu Asn Ala Ser Gly Asn
            420                 425                 430

Leu Tyr Ile His Ala Gly Lys Asp Leu Asp Leu Asn Ala Asp Lys Asp
        435                 440                 445

Leu Ser Thr Gln Ser Ile Ser Leu Arg Ala Asp Asn Thr Ala Leu Ile
    450                 455                 460

Ser Ser Asn Gly Asn Thr Leu Thr Ala Glu Lys Asn Leu Asp Ile Gln
465                 470                 475                 480

Ala Gly Ser Leu Ser Val Arg Gln Ser Asn Leu Gln Ser Ser Gly Gly
                485                 490                 495

Asn Val Gln Met Ser Ala Thr Lys Gly Asn Ile Ser Leu Asn Gln Ser
            500                 505                 510

Trp Ile Asn Ala Ser Gln Asn Ile Asp Thr Ala Ala Leu Gln Gly Asn
        515                 520                 525

Ile Ile Ser Asp Gly Leu Thr Ala Val Ala Glu Val Gly Arg Val Ser
    530                 535                 540

Leu Leu Ala Asn Gly Asn Val Asp Phe Asn Gly Leu Asn Thr Leu Ile
545                 550                 555                 560

Ala Glu Gly Asp Ile Asn Ala Gly Ser Val Gly Lys Gly Arg Leu Lys
                565                 570                 575

Met Asp Asn Thr Asp Ile Tyr Ala Ser Ala Gly Asp Val Lys Leu Val
            580                 585                 590

Ala Gly Gly Gln Leu Asp Leu Gly Asn Gly Thr Val Asn Gly Gly His
        595                 600                 605

Ile Ser Leu Asp Ser Asn Lys Gly Ser Met Val Val Gln Asn Val His
    610                 615                 620

Leu Asn Ala Arg Ala Ser Leu Lys Val Asp Ala Asp Gln Thr Leu Thr
625                 630                 635                 640

Ile Asn Asn Ser Lys Leu Asn Ser Asp His Asn Thr Gln Ile Asn Thr
                645                 650                 655

Asn His Gly His Met Thr Leu Asn Gln Leu Asp Ala His Ser Arg Arg
            660                 665                 670

His Met Ser Ile Ser Ala Gln Gly Lys Gly Lys Gly Lys Asp Ser Gly
        675                 680                 685

Gln Ile Leu Gln Asn Asp Gln Gln Asn Ser Lys Ser Thr Leu Ala Ala
    690                 695                 700

Asp Gly Val Leu Ser Leu Asn Ser Ser Ala Leu Gln Val Leu Asp Asn
705                 710                 715                 720

Thr Thr Leu Arg Gly Gly Ala Ile Asn Ile Lys Ala Gly Gly Gly Ile
                725                 730                 735

Ile Lys Arg Gly His Ile Asp Trp Glu Thr Gln Asp Thr Ala Thr Met
            740                 745                 750

Arg Ser Ala Glu Leu Lys Pro Leu Ser Gly Met Met Ser Ile Glu Ser
        755                 760                 765

Gly Gly Asp Asn Pro Leu Thr Val Glu Pro Gly Asn Arg Ile Val Ser
    770                 775                 780
```

-continued

```
Ala Gly Asp Leu Ala Val Asn His Asn Gly Thr Phe Gln Ile Ser Ala
785                 790                 795                 800

Arg Ala Gly Asn Asn Gly Asn Pro Ser Ala Gln Thr Ala Ser Val Ser
                805                 810                 815

Ala Lys Gly Asn Ile Gly Ile Val Ala Gly Glu Val Asp Ile Asp Ala
            820                 825                 830

Ala Asn Ile Ala Ala Gly Lys Asp Leu Ala Leu Val Ala Thr Lys Gly
        835                 840                 845

Asn Ile Ser Leu Asn Ser Ile Arg Asn Thr Phe Ser Asn Tyr Gln Leu
    850                 855                 860

Lys Thr Asp Lys His Asn Ile Thr Gln Gln Leu Thr Asp Val Glu Gln
865                 870                 875                 880

Glu Leu Ser Lys Leu Thr Ser Asp Pro Lys Tyr Arg Lys Ala Gln Asp
                885                 890                 895

Leu Ser Gln Met Leu Arg Arg Lys Tyr Lys Arg Arg Asp Lys Val Phe
            900                 905                 910

Gly Asp Ser Glu Ala Arg Leu Arg Gly Leu Arg Ala Lys Ile Asn Ala
        915                 920                 925

Ala Asp Glu Ala Trp Ala Glu Arg Gln Ser Pro Val Lys Ala Leu Leu
    930                 935                 940

Glu Arg Lys Gln Leu Leu Gln Gln Ala Leu Leu Thr Val Ser Gln Pro
945                 950                 955                 960

Gly Ser Gly His Glu Asn Gln Gly Ser Thr Leu Ser Gly Gln Asn Ile
                965                 970                 975

Lys Leu Leu Ala Ala Gly Gly Ile Arg Ile Gln Gly Ser Lys Val Ala
            980                 985                 990

Ala Thr Gln Gln Ala Asn Ile Gln Ala Ala Gly Phe Leu Pro Ala Pro
        995                 1000                1005

Ala Ala Glu Glu Leu Gln Glu Gly Arg Leu Gln Ser Ala Ile Asp Ile
    1010                1015                1020

Ser Gly Val Leu Asp Thr Phe Glu Tyr Gly Gln Gln Gly Ser Asp Lys
1025                1030                1035                1040

Tyr Gly Tyr Ala Ile Phe Ser Arg Pro Ser Glu Ile Ser Gly Lys Thr
                1045                1050                1055

Gly Val Thr Leu Ser Ala Pro Asn Ala Asn Glu Asn Ser Arg Ile Ser
            1060                1065                1070

Leu Ser Ala Ala Asn Ile Glu Ala Glu Asn Gly Lys Ile Lys Ile Gln
        1075                1080                1085

Ser Tyr Gly Asp Gln Ser Tyr Tyr Ala Gly Gln Gly Glu Leu Tyr Thr
    1090                1095                1100

Phe Glu Arg Arg Ser Tyr Lys Thr Gly Lys Trp Tyr Asn Arg Lys His
1105                1110                1115                1120

Ile Thr Glu Val Lys Glu His Lys Asn Ala Lys Pro Asp Ala Val Asn
                1125                1130                1135

Leu Ser Ala Ser Gln Gly Ile Asp Ile Lys Ser Gly Gly Ser Ile Asp
            1140                1145                1150

Ala Tyr Ala Thr Ala Phe Asp Ala Pro Lys Gly Ser Ile Asn Ile Glu
        1155                1160                1165

Ala Gly Arg Lys Leu Thr Leu Tyr Ala Val Glu Glu Leu Asn Tyr Asp
    1170                1175                1180

Lys Leu Asp Ser Gln Lys Arg Arg Arg Phe Leu Gly Ile Ser Tyr Ser
1185                1190                1195                1200

Lys Ala His Asp Thr Thr Thr Gln Val Met Lys Thr Ala Leu Pro Ser
                1205                1210                1215
```

-continued

```
Arg Val Val Ala Glu Ser Ala Asn Leu Gln Ser Gly Trp Asp Thr Lys
            1220                1225                1230

Leu Gln Gly Thr Gln Phe Glu Thr Thr Leu Gly Gly Ala Thr Ile Arg
        1235                1240                1245

Ala Gly Val Gly Glu Gln Ala Arg Ala Asp Ala Lys Ile Ile Leu Glu
    1250                1255                1260

Gly Ile Lys Ser Ser Ile His Thr Glu Thr Val Ser Ser Ser Lys Ser
1265                1270                1275                1280

Thr Leu Trp Gln Lys Gln Ala Gly Arg Gly Ser Asn Ile Glu Thr Leu
                1285                1290                1295

Gln Leu Pro Ser Phe Thr Gly Pro Val Ala Pro Val Leu Ser Ala Pro
            1300                1305                1310

Gly Gly Tyr Ile Val Asp Ile Pro Gln Gly Asn Leu Lys Thr Gln Ile
        1315                1320                1325

Glu Thr Leu Thr Lys Gln Pro Glu Tyr Ala Tyr Leu Asn Asn Phe Lys
    1330                1335                1340

Leu Arg Lys Thr Ser Thr Gly Ile Thr Cys Ser Leu Leu Thr Ile Asn
1345                1350                1355                1360

Gly Thr Thr Asn Arg Xaa Xaa Xaa His Thr
                1365                1370


<210> SEQ ID NO 21
<211> LENGTH: 2205
<212> TYPE: DNA
<213> ORGANISM: Neisseria meningitidis
<220> FEATURE:
<221> NAME/KEY: misc_feature
<222> LOCATION: 4, 5, 6, 7, 8
<223> OTHER INFORMATION: n = A,T,C or G

<400> SEQUENCE: 21

gtgnnnnngc aaatcaaact gcaatcctac ggcgaccaat cctattacgc cggacagggc     60

gaactctata cctttgaacg ccgcagctac aaaaccggca aatggtacaa ccgcaaacac    120

attaccgaag tcaaagaaca caaaaacgcc aagcccgacg cagtaaacct cagcgcatcc    180

caaggcatcg acatcaaatc tggtggcagc atcgacgcct acgccaccgc attcgatgcc    240

cccaaaggca gcattaacat cgaagccggg cggaaattga cactctatgc cgtagaagag    300

ctcaactacg acaaactaga cagccaaaaa aggcgcagat ttctcggcat cagctacagc    360

aaagcacacg acaccaccac ccaagtcatg aaaaccgcgc tgccctcaag ggtagttgca    420

gaatcagcca atctgcaatc aggttgggat accaaactgc aaggcacaca gtttgaaacc    480

acactgggtg gcgcaaccat acgcgcaggc gtaggcgagc aggcacgggc agatgccaag    540

attatcctcg aagggatcaa aagcagcatc cacacagaaa ccgtgagcag cagcaaatct    600

actctatggc aaaaacaggc aggacggggc agtaacatcg aaaccttgca attgccgagt    660

ttcaccggtc ccgttgcgcc cgtactgtcc gcacccggcg gttacattgt cgatattccc    720

caaggcaatc tgaaaaccca aatcgaaacc ctcaccaaac agcccgagta tgcttatttg    780

aaacaacttc aagttgcgaa aaacatcaac tggaatcagg tgcagcttgc ttacgataaa    840

tgggactaca aacaggaggg cttaaccgaa gcaggtgcgg cgattatcgc actggccgtt    900

accgtggtca cctcaggcgc aggaaccgga gccgtattgg gattaaacgg tgcggccgcc    960

gccgcaaccg atgcagcatt tgcctctttg gccagccagg cttccgtatc gttcatcaac   1020

aacaaaggca atatcggtaa caccctgaaa gagctgggca gaagcagcac ggtgaaaaat   1080

ctggtggttg ccgccgctac cgcaggcgta tccaacaaaa tcggtgcttc ctcccttgcc   1140
```

```
acttggagcg aaaccccttg ggtaaacaac ctcaacgtca acttggccaa tgcgggcagt   1200

gccgcactga ttaataccgc tgtcaacggc ggcagcctga aagacaatct ggaagcgaat   1260

atccttgcgg ctttggtcaa taccgcgcat ggagaagcag ccagtaaaat caaacagttg   1320

gatcagcact acatagtcca caagattgcc catgccatag cgggctgtgc ggcagcggcg   1380

gcgaataagg gcaagtgtca ggatggtgcg ataggcgctg cagtcggtga gattgttggt   1440

gaggctttgg ttaagaatac cgatttcagc ggtatgactg cttctgaaat tgaaaaagct   1500

aaagcgaata ttactgcgta tgcaaaattg gtagccggag cgactgtagg tgttacagga   1560

ggcaatgttg atgtggcggc aaatgcttcc gaaacagctg ttaaaaataa tgcattagat   1620

attatttggg atatcggcaa cctcgtatgg gacggcggta aatggattta cgccaaatct   1680

attggcgata agcagatggc tcgagaagcg gcgattgatt ttggtgtgga tgccgccgca   1740

gctgccgttc cctttgttcc ggcaggtgcg actaaaatca gccgaggcgg ggcttatgtt   1800

ctgaaggcgg gagacgaagc agttgatacg gctaaagcca tacaggaaat tcagaagcag   1860

accggaatca agcttactta tgataaggtt aataaggttt ggacaacacc ggcggggtta   1920

gattatgggt tagatgctaa gcatggtaat aggattaaac atgttttagc ccatacaatt   1980

ccaaatccaa acaaacctgt tcattctgtt tttaatgtgt cccgtaaaga agttttgcct   2040

ttggttgatg aagcttggag aatgaaagga aatcctttgc caaatgattc atccgtatat   2100

cttgtagata tgaagaaacc tattggaaca aaaggagaaa caaaagtgcg gattgttgtg   2160

caaaaaggaa caaataaaat catttctgca tatcctcaga aataa                   2205
```

```
<210> SEQ ID NO 22
<211> LENGTH: 734
<212> TYPE: PRT
<213> ORGANISM: Neisseria meningitidis
<220> FEATURE:
<221> NAME/KEY: VARIANT
<222> LOCATION: 2, 3
<223> OTHER INFORMATION: Xaa = Any Amino Acid

<400> SEQUENCE: 22

Met Xaa Xaa Gln Ile Lys Leu Gln Ser Tyr Gly Asp Gln Ser Tyr Tyr
 1               5                  10                  15

Ala Gly Gln Gly Glu Leu Tyr Thr Phe Glu Arg Arg Ser Tyr Lys Thr
            20                  25                  30

Gly Lys Trp Tyr Asn Arg Lys His Ile Thr Glu Val Lys Glu His Lys
        35                  40                  45

Asn Ala Lys Pro Asp Ala Val Asn Leu Ser Ala Ser Gln Gly Ile Asp
    50                  55                  60

Ile Lys Ser Gly Gly Ser Ile Asp Ala Tyr Ala Thr Ala Phe Asp Ala
65                  70                  75                  80

Pro Lys Gly Ser Ile Asn Ile Glu Ala Gly Arg Lys Leu Thr Leu Tyr
                85                  90                  95

Ala Val Glu Glu Leu Asn Tyr Asp Lys Leu Asp Ser Gln Lys Arg Arg
            100                 105                 110

Arg Phe Leu Gly Ile Ser Tyr Ser Lys Ala His Asp Thr Thr Thr Gln
        115                 120                 125

Val Met Lys Thr Ala Leu Pro Ser Arg Val Val Ala Glu Ser Ala Asn
    130                 135                 140

Leu Gln Ser Gly Trp Asp Thr Lys Leu Gln Gly Thr Gln Phe Glu Thr
145                 150                 155                 160

Thr Leu Gly Gly Ala Thr Ile Arg Ala Gly Val Gly Glu Gln Ala Arg
```

```
                165                 170                 175

Ala Asp Ala Lys Ile Ile Leu Glu Gly Ile Lys Ser Ser Ile His Thr
            180                 185                 190

Glu Thr Val Ser Ser Ser Lys Ser Thr Leu Trp Gln Lys Gln Ala Gly
        195                 200                 205

Arg Gly Ser Asn Ile Glu Thr Leu Gln Leu Pro Ser Phe Thr Gly Pro
    210                 215                 220

Val Ala Pro Val Leu Ser Ala Pro Gly Gly Tyr Ile Val Asp Ile Pro
225                 230                 235                 240

Gln Gly Asn Leu Lys Thr Gln Ile Glu Thr Leu Thr Lys Gln Pro Glu
                245                 250                 255

Tyr Ala Tyr Leu Lys Gln Leu Gln Val Ala Lys Asn Ile Asn Trp Asn
            260                 265                 270

Gln Val Gln Leu Ala Tyr Asp Lys Trp Asp Tyr Lys Gln Glu Gly Leu
        275                 280                 285

Thr Glu Ala Gly Ala Ala Ile Ile Ala Leu Ala Val Thr Val Val Thr
    290                 295                 300

Ser Gly Ala Gly Thr Gly Ala Val Leu Gly Leu Asn Gly Ala Ala Ala
305                 310                 315                 320

Ala Ala Thr Asp Ala Ala Phe Ala Ser Leu Ala Ser Gln Ala Ser Val
                325                 330                 335

Ser Phe Ile Asn Asn Lys Gly Asn Ile Gly Asn Thr Leu Lys Glu Leu
            340                 345                 350

Gly Arg Ser Ser Thr Val Lys Asn Leu Val Val Ala Ala Ala Thr Ala
        355                 360                 365

Gly Val Ser Asn Lys Ile Gly Ala Ser Ser Leu Ala Thr Trp Ser Glu
    370                 375                 380

Thr Pro Trp Val Asn Asn Leu Asn Val Asn Leu Ala Asn Ala Gly Ser
385                 390                 395                 400

Ala Ala Leu Ile Asn Thr Ala Val Asn Gly Gly Ser Leu Lys Asp Asn
                405                 410                 415

Leu Glu Ala Asn Ile Leu Ala Ala Leu Val Asn Thr Ala His Gly Glu
            420                 425                 430

Ala Ala Ser Lys Ile Lys Gln Leu Asp Gln His Tyr Ile Val His Lys
        435                 440                 445

Ile Ala His Ala Ile Ala Gly Cys Ala Ala Ala Ala Ala Asn Lys Gly
    450                 455                 460

Lys Cys Gln Asp Gly Ala Ile Gly Ala Ala Val Gly Glu Ile Val Gly
465                 470                 475                 480

Glu Ala Leu Val Lys Asn Thr Asp Phe Ser Gly Met Thr Ala Ser Glu
                485                 490                 495

Ile Glu Lys Ala Lys Ala Asn Ile Thr Ala Tyr Ala Lys Leu Val Ala
            500                 505                 510

Gly Ala Thr Val Gly Val Thr Gly Gly Asn Val Asp Val Ala Ala Asn
        515                 520                 525

Ala Ser Glu Thr Ala Val Lys Asn Asn Ala Leu Asp Ile Ile Trp Asp
    530                 535                 540

Ile Gly Asn Leu Val Trp Asp Gly Gly Lys Trp Ile Tyr Ala Lys Ser
545                 550                 555                 560

Ile Gly Asp Lys Gln Met Ala Arg Glu Ala Ala Ile Asp Phe Gly Val
                565                 570                 575

Asp Ala Ala Ala Ala Ala Val Pro Phe Val Pro Ala Gly Ala Thr Lys
            580                 585                 590
```

```
Ile Ser Arg Gly Gly Ala Tyr Val Leu Lys Ala Gly Asp Glu Ala Val
        595                 600                 605

Asp Thr Ala Lys Ala Ile Gln Glu Ile Gln Lys Gln Thr Gly Ile Lys
    610                 615                 620

Leu Thr Tyr Asp Lys Val Asn Lys Val Trp Thr Thr Pro Ala Gly Leu
625                 630                 635                 640

Asp Tyr Gly Leu Asp Ala Lys His Gly Asn Arg Ile Lys His Val Leu
                645                 650                 655

Ala His Thr Ile Pro Asn Pro Asn Lys Pro Val His Ser Val Phe Asn
            660                 665                 670

Val Ser Arg Lys Glu Val Leu Pro Leu Val Asp Glu Ala Trp Arg Met
        675                 680                 685

Lys Gly Asn Pro Leu Pro Asn Asp Ser Ser Val Tyr Leu Val Asp Met
    690                 695                 700

Lys Lys Pro Ile Gly Thr Lys Gly Glu Thr Lys Val Arg Ile Val Val
705                 710                 715                 720

Gln Lys Gly Thr Asn Lys Ile Ile Ser Ala Tyr Pro Gln Lys
                725                 730


<210> SEQ ID NO 23
<211> LENGTH: 2664
<212> TYPE: DNA
<213> ORGANISM: Neisseria meningitidis

<400> SEQUENCE: 23

gtgagcatta gcgcaccgta tgccaatgag aacagtcgca tcctgctcag caccacggat     60

atcagttcgg aaaacggcaa aatcaaaatt caatcttacg gtgaccaata ttactatgcg    120

agacagagcg aactctatac ctttgaacgc cgcagctaca aaaccggcaa atggtacaac    180

cgcaaacaca ttaccgaagt caaagaacac aaaaacgcca agcccgacgc agtaaccctc    240

agcgcatccc aaggcatcga catcaaatct ggtggcagca tcgacgccta cgccaccgca    300

ttcgatgccc ccaaaggcag cattaacatc gaagccgggc ggaaattgac actctatgcc    360

gtagaagagc tcaactacga caaactagac agccaaaaaa ggcgcagatt tctcggcatc    420

agctacagca aagcacacga caccaccacc caagtcatga aaaccgcgct gccctcaagg    480

gtagttgcag aatcagccaa cctccaatcg ggctgggata ccaaactgca aggcacacag    540

tttgaaacca cactgggtgg cgcaaccata cgcgcaggcg taggtgagca ggcacgggca    600

gatgccaaga ttatcctcga aggcatcaaa accacgatcc acaacgaaac cgtgagcagc    660

agcaaatctg ctctatggca aaaacaggca ggacggggca gtaacatcga aaccttgcaa    720

ttgccgagtt tcaccggtcc cgttgcgccc gtactgtccg cacccggcgg ttacattgtc    780

gacatcccca aaggcaatct gaaaaccgaa atcgaaaagc tggccaaaca gcccgaatac    840

gcctacctga aacagcttca gacggccaag aacgtcgatt ggaaacaggt gcagctggcc    900

tacgacaaat gggactataa acaggaaggc ttgaccggag ccggtgcagc gattgtggtg    960

attattgtaa ccgctctaac ttatggatac ggagcggctg cagcgggtag cgtaactgcc   1020

gcaggaagta gtacagccgc agctgcaaca acgacagcgg cagcaactac cactgtttct   1080

actgcagctg ccatgcaaac cgcagcttta gcctccttgt atagccaagc agctgtagcc   1140

atcatcaata ataaaggcga tgtaggcaaa gcattaaaag atctcggcac cagtgatacg   1200

gtcaagcaga ttgttacttc cgcactgacg gcgggtgcat taaaccagat gggcgcagat   1260

attgcccaat tgaacagcaa ggtaagaacc gaactgttca gcagtacggg caatcaaacc   1320

attgccaacc ttggaggcag attggccacc aacctcagca atgcaggtat ctcagctggt   1380
```

atcaataccg ccgttaacgg cggcagcttg aaagacaact taggcaatgc cgcattggga 1440
gcattggtta atagcttcca aggggaagcc gccagcaaaa tcaaaacaac cttcagcgac 1500
gattatgttg ccaaacagtt cgcccacgct ttggcgggtt gtgttagcgg actggtacag 1560
ggaaaatgta aagatggggc aattggcgca gcagttgggg aaatcgtagc tgaatccata 1620
cttggcggca gaaaccctgc tacactcagc gatgcagaaa agcataaagt tatcagttac 1680
tcgaagatta ttgcgggcag cgtggcggca ctcaacggcg gcgatgtgaa tactgcggcg 1740
aatgcggctg aggtagctgt ggtgaataat gctttgaatt ttgacagtac ccctaccaat 1800
gcgaaaaagc atcaaccgca gaagcccgac aaaaccgcac tggaaaaaat catccaaagt 1860
attatgcctg cacatgcggc aggtgcgatg actaatccgc aggataagga tgctgccatt 1920
tggataagca atatccgtaa tggcatcaca ggcccgattg tgattaccag ctatggagtt 1980
tatgcagcag gttggacagc tccgctgatc ggtacagctg gtaaagcagc tatcagcacc 2040
tgtatggcta atccttctgg ttgtactgtc atggttacgc aggctgctga agcgggcgcg 2100
ggaatcgtca cgggtgcggt aacggtaggc aacgcttggg aagctccagt aggagcgttg 2160
tcgaaagcga aggcggctaa gcaagctgct cctaaagaaa caataaacaa tttggcaaat 2220
ttagccaaag cagaacagca gattttattc cgtattgccc aacgcgatac gcaactggat 2280
gcatggaaga cgggatttaa caatagagta aggaaaggag caggcttgct tgatgcaagt 2340
aatattccga taaccattaa cggaaaaacc atcaaacctg tacaagccat aagcttaaag 2400
ggagcacccg tttacagcgg cgtaagcgaa caggagattt ttgcgcttta tcggcagatg 2460
actggccaga atccgaattt tagagttttg cctgacggaa gattagcaaa tggcattatc 2520
agtactggag aatgggcagg aacaaaaatt gcattaagaa atttttcaaa aacagagaat 2580
tcaactcaag cacgatggac attagatttg cagaatcctc catcatttat taaaggtact 2640
aaattggagc ttaaattcca ataa 2664

<210> SEQ ID NO 24
<211> LENGTH: 887
<212> TYPE: PRT
<213> ORGANISM: Neisseria meningitidis

<400> SEQUENCE: 24

Met Ser Ile Ser Ala Pro Tyr Ala Asn Glu Asn Ser Arg Ile Leu Leu
1 5 10 15

Ser Thr Thr Asp Ile Ser Ser Glu Asn Gly Lys Ile Lys Ile Gln Ser
20 25 30

Tyr Gly Asp Gln Tyr Tyr Tyr Ala Arg Gln Ser Glu Leu Tyr Thr Phe
35 40 45

Glu Arg Arg Ser Tyr Lys Thr Gly Lys Trp Tyr Asn Arg Lys His Ile
50 55 60

Thr Glu Val Lys Glu His Lys Asn Ala Lys Pro Asp Ala Val Thr Leu
65 70 75 80

Ser Ala Ser Gln Gly Ile Asp Ile Lys Ser Gly Gly Ser Ile Asp Ala
85 90 95

Tyr Ala Thr Ala Phe Asp Ala Pro Lys Gly Ser Ile Asn Ile Glu Ala
100 105 110

Gly Arg Lys Leu Thr Leu Tyr Ala Val Glu Glu Leu Asn Tyr Asp Lys
115 120 125

Leu Asp Ser Gln Lys Arg Arg Arg Phe Leu Gly Ile Ser Tyr Ser Lys
130 135 140

```
Ala His Asp Thr Thr Thr Gln Val Met Lys Thr Ala Leu Pro Ser Arg
145                 150                 155                 160

Val Val Ala Glu Ser Ala Asn Leu Gln Ser Gly Trp Asp Thr Lys Leu
                165                 170                 175

Gln Gly Thr Gln Phe Glu Thr Thr Leu Gly Gly Ala Thr Ile Arg Ala
            180                 185                 190

Gly Val Gly Glu Gln Ala Arg Ala Asp Ala Lys Ile Ile Leu Glu Gly
        195                 200                 205

Ile Lys Thr Thr Ile His Asn Glu Thr Val Ser Ser Ser Lys Ser Ala
    210                 215                 220

Leu Trp Gln Lys Gln Ala Gly Arg Gly Ser Asn Ile Glu Thr Leu Gln
225                 230                 235                 240

Leu Pro Ser Phe Thr Gly Pro Val Ala Pro Val Leu Ser Ala Pro Gly
                245                 250                 255

Gly Tyr Ile Val Asp Ile Pro Lys Gly Asn Leu Lys Thr Glu Ile Glu
            260                 265                 270

Lys Leu Ala Lys Gln Pro Glu Tyr Ala Tyr Leu Lys Gln Leu Gln Thr
        275                 280                 285

Ala Lys Asn Val Asp Trp Lys Gln Val Gln Leu Ala Tyr Asp Lys Trp
    290                 295                 300

Asp Tyr Lys Gln Glu Gly Leu Thr Gly Ala Gly Ala Ala Ile Val Val
305                 310                 315                 320

Ile Ile Val Thr Ala Leu Thr Tyr Gly Tyr Gly Ala Ala Ala Ala Gly
                325                 330                 335

Ser Val Thr Ala Ala Gly Ser Ser Thr Ala Ala Ala Ala Thr Thr Thr
            340                 345                 350

Ala Ala Ala Thr Thr Thr Val Ser Thr Ala Ala Ala Met Gln Thr Ala
        355                 360                 365

Ala Leu Ala Ser Leu Tyr Ser Gln Ala Ala Val Ala Ile Ile Asn Asn
    370                 375                 380

Lys Gly Asp Val Gly Lys Ala Leu Lys Asp Leu Gly Thr Ser Asp Thr
385                 390                 395                 400

Val Lys Gln Ile Val Thr Ser Ala Leu Thr Ala Gly Ala Leu Asn Gln
                405                 410                 415

Met Gly Ala Asp Ile Ala Gln Leu Asn Ser Lys Val Arg Thr Glu Leu
            420                 425                 430

Phe Ser Ser Thr Gly Asn Gln Thr Ile Ala Asn Leu Gly Gly Arg Leu
        435                 440                 445

Ala Thr Asn Leu Ser Asn Ala Gly Ile Ser Ala Gly Ile Asn Thr Ala
    450                 455                 460

Val Asn Gly Gly Ser Leu Lys Asp Asn Leu Gly Asn Ala Ala Leu Gly
465                 470                 475                 480

Ala Leu Val Asn Ser Phe Gln Gly Glu Ala Ala Ser Lys Ile Lys Thr
                485                 490                 495

Thr Phe Ser Asp Asp Tyr Val Ala Lys Gln Phe Ala His Ala Leu Ala
            500                 505                 510

Gly Cys Val Ser Gly Leu Val Gln Gly Lys Cys Lys Asp Gly Ala Ile
        515                 520                 525

Gly Ala Ala Val Gly Glu Ile Val Ala Glu Ser Ile Leu Gly Gly Arg
    530                 535                 540

Asn Pro Ala Thr Leu Ser Asp Ala Glu Lys His Lys Val Ile Ser Tyr
545                 550                 555                 560

Ser Lys Ile Ile Ala Gly Ser Val Ala Ala Leu Asn Gly Gly Asp Val
                565                 570                 575
```

Asn Thr Ala Ala Asn Ala Ala Glu Val Ala Val Val Asn Asn Ala Leu
580 585 590

Asn Phe Asp Ser Thr Pro Thr Asn Ala Lys Lys His Gln Pro Gln Lys
595 600 605

Pro Asp Lys Thr Ala Leu Glu Lys Ile Ile Gln Ser Ile Met Pro Ala
610 615 620

His Ala Ala Gly Ala Met Thr Asn Pro Gln Asp Lys Asp Ala Ala Ile
625 630 635 640

Trp Ile Ser Asn Ile Arg Asn Gly Ile Thr Gly Pro Ile Val Ile Thr
645 650 655

Ser Tyr Gly Val Tyr Ala Ala Gly Trp Thr Ala Pro Leu Ile Gly Thr
660 665 670

Ala Gly Lys Ala Ala Ile Ser Thr Cys Met Ala Asn Pro Ser Gly Cys
675 680 685

Thr Val Met Val Thr Gln Ala Ala Glu Ala Gly Ala Gly Ile Val Thr
690 695 700

Gly Ala Val Thr Val Gly Asn Ala Trp Glu Ala Pro Val Gly Ala Leu
705 710 715 720

Ser Lys Ala Lys Ala Ala Lys Gln Ala Ala Pro Lys Glu Thr Ile Asn
725 730 735

Asn Leu Ala Asn Leu Ala Lys Ala Glu Gln Gln Ile Leu Phe Arg Ile
740 745 750

Ala Gln Arg Asp Thr Gln Leu Asp Ala Trp Lys Thr Gly Phe Asn Asn
755 760 765

Arg Val Arg Lys Gly Ala Gly Leu Leu Asp Ala Ser Asn Ile Pro Ile
770 775 780

Thr Ile Asn Gly Lys Thr Ile Lys Pro Val Gln Ala Ile Ser Leu Lys
785 790 795 800

Gly Ala Pro Val Tyr Ser Gly Val Ser Glu Gln Glu Ile Phe Ala Leu
805 810 815

Tyr Arg Gln Met Thr Gly Gln Asn Pro Asn Phe Arg Val Leu Pro Asp
820 825 830

Gly Arg Leu Ala Asn Gly Ile Ile Ser Thr Gly Glu Trp Ala Gly Thr
835 840 845

Lys Ile Ala Leu Arg Asn Phe Ser Lys Thr Glu Asn Ser Thr Gln Ala
850 855 860

Arg Trp Thr Leu Asp Leu Gln Asn Pro Pro Ser Phe Ile Lys Gly Thr
865 870 875 880

Lys Leu Glu Leu Lys Phe Gln
885

<210> SEQ ID NO 25
<211> LENGTH: 2385
<212> TYPE: DNA
<213> ORGANISM: Neisseria meningitidis

<400> SEQUENCE: 25
ttgacactct atgccgtaga agagctcaac tacgacaaac tagacagcca aaaaaggcgc 60
agatttctcg gcatcagcta cagcaaagca cacgacacca ccacccaagt catgaaaacc 120
gcgctgccct caagggtagt tgcagaatca gccaatctgc aatcaggttg ggataccaaa 180
ctgcaaggca cacagtttga aaccacactg ggtggcgcaa ccatacgcgc aggcgtaggc 240
gagcaggcac gggcagatgc caagattatc ctcgaaggga tcaaaagcag catccacaca 300
gaaaccgtga gcagcagcaa atctactcta tggcaaaaac aggcaggacg gggcagtaac 360

-continued

```
atcgaaacct tgcaattgcc gagtttcacc ggtcccgttg cgcccgtact gtccgcaccc    420
ggcggttaca ttgtcgatat tccccaaggc aatctgaaaa cccaaatcga aaccctcacc    480
aaacagcccg agtatgctta tttgaaacaa cttcaagttg cgaaaaacat caactggaat    540
caggtgcagc ttgcttacga taaatgggac tacaaacagg agggcttaac cgaagcaggt    600
gcggcgatta tcgcactggc cgttaccgtg gtcacctcag gcgcaggaac cggagccgta    660
ttgggattaa acggtgcggc cgccgccgca accgatgcag catttgcctc tttggccagc    720
caggcttccg tatcgttcat caacaacaaa ggcaatatcg gtaacaccct gaaagagctg    780
ggcagaagca gcacggtgaa aaatctggtg gttgccgccg ctaccgcagg cgtagccgac    840
aaaatcggcg cttcggcact gaacaatgtc agcgataagc agtggatcaa caacctgacc    900
gtcaacctag ccaatgcggg cagtgccgca ctgattaata ccgctgtcaa cggcggcagc    960
ctgaaagaca atctggaagc gaatatcctt gcggctttgg tcaataccgc gcatggagaa   1020
gcagccagta aaatcaaaca gttggatcag cactacatag tccacaagat tgcccatgcc   1080
atagcgggct gtgcggcagc ggcggcgaat aagggtaagt gtcaggatgg tgcgatcggt   1140
gcggctgtgg gcgagatagt cggggaggct ttgacaaacg gcaaaaatcc tgccactttg   1200
acagctaaag aacgcgaaca gattttggca tacagcaaac tggttgccgg tacggtaagc   1260
ggtgtggtcg gcggcgatgt gaatacagcg gcgaatgcgg ctaaagtcgc gattgaaaat   1320
aacctattat ctcaagaaga gtatgctctt agagaaaaat tgatcaaaaa agccaaaggg   1380
aaaggcctat tatctttaga ttggggcagc ctgaccgaac aagaggcaag gcagtttatc   1440
tatttgattg agaaagatcg atattctaat caattgcttg accgatatca aaaaaatcca   1500
agtagtttaa ataatcaaga aaaaaatatt cttgcatatt ttattaacca aacctctgga   1560
ggtaacacag cttgggcagc ttcgatactg aaaacgcccc agtcaatggg taatctcact   1620
attccttcca aagatattaa taacacctta tcgaaagcct atcaaacatt gagtcgttat   1680
gattcttttg attacaaatc agctgttgcc gcacaacctg cactttactt attaaacgga   1740
ccgcttggct tcagtgtcaa agcagctact gtggcagcag gaggatataa cattggacag   1800
ggagcgaaag caatctctaa tggagaatat ctgcatggta cagttcaggt tgttaatggc   1860
acattgatgg ttgcaggatc tgtatctgca caggctgcaa tatcggccaa gcctgcacct   1920
gttacccgtt atctgagcaa tgacagtgct cctgctttaa gacaagcttt aactgctgaa   1980
agccagagaa tccgcatgaa actgccggaa gagtatcgac aaatagggaa tcttgcgata   2040
gcaaaaaattg atgttaaagg attaccgcaa aggatggaag catttagttc tttccaaaaa   2100
ggggaacatg gatttatttc gttacctgaa acaaaaattt ttaaacctat atctgttgat   2160
aaatatcata atattgcctc tcctcctaga ggaacattaa gaaatataga tggagaatat   2220
aaattacttg aaactatagc acagcaactc ggaaataatc gtaatgtatc aggtagaatt   2280
gatctattta cagaattaaa ggcctgtcaa tcttgcagca atgttatttt agagtttaga   2340
aatcgctatc caaatattca attaaatatt tttacaggaa aatag                   2385
```

<210> SEQ ID NO 26
<211> LENGTH: 794
<212> TYPE: PRT
<213> ORGANISM: Neisseria meningitidis

<400> SEQUENCE: 26

```
Met Thr Leu Tyr Ala Val Glu Glu Leu Asn Tyr Asp Lys Leu Asp Ser
 1               5                  10                  15
```

-continued

```
Gln Lys Arg Arg Arg Phe Leu Gly Ile Ser Tyr Ser Lys Ala His Asp
            20                  25                  30

Thr Thr Thr Gln Val Met Lys Thr Ala Leu Pro Ser Arg Val Val Ala
        35                  40                  45

Glu Ser Ala Asn Leu Gln Ser Gly Trp Asp Thr Lys Leu Gln Gly Thr
    50                  55                  60

Gln Phe Glu Thr Thr Leu Gly Gly Ala Thr Ile Arg Ala Gly Val Gly
65                  70                  75                  80

Glu Gln Ala Arg Ala Asp Ala Lys Ile Ile Leu Glu Gly Ile Lys Ser
                85                  90                  95

Ser Ile His Thr Glu Thr Val Ser Ser Ser Lys Ser Thr Leu Trp Gln
            100                 105                 110

Lys Gln Ala Gly Arg Gly Ser Asn Ile Glu Thr Leu Gln Leu Pro Ser
        115                 120                 125

Phe Thr Gly Pro Val Ala Pro Val Leu Ser Ala Pro Gly Gly Tyr Ile
    130                 135                 140

Val Asp Ile Pro Gln Gly Asn Leu Lys Thr Gln Ile Glu Thr Leu Thr
145                 150                 155                 160

Lys Gln Pro Glu Tyr Ala Tyr Leu Lys Gln Leu Gln Val Ala Lys Asn
                165                 170                 175

Ile Asn Trp Asn Gln Val Gln Leu Ala Tyr Asp Lys Trp Asp Tyr Lys
            180                 185                 190

Gln Glu Gly Leu Thr Glu Ala Gly Ala Ala Ile Ile Ala Leu Ala Val
        195                 200                 205

Thr Val Val Thr Ser Gly Ala Gly Thr Gly Ala Val Leu Gly Leu Asn
    210                 215                 220

Gly Ala Ala Ala Ala Ala Thr Asp Ala Ala Phe Ala Ser Leu Ala Ser
225                 230                 235                 240

Gln Ala Ser Val Ser Phe Ile Asn Asn Lys Gly Asn Ile Gly Asn Thr
                245                 250                 255

Leu Lys Glu Leu Gly Arg Ser Ser Thr Val Lys Asn Leu Val Val Ala
            260                 265                 270

Ala Ala Thr Ala Gly Val Ala Asp Lys Ile Gly Ala Ser Ala Leu Asn
        275                 280                 285

Asn Val Ser Asp Lys Gln Trp Ile Asn Asn Leu Thr Val Asn Leu Ala
    290                 295                 300

Asn Ala Gly Ser Ala Ala Leu Ile Asn Thr Ala Val Asn Gly Gly Ser
305                 310                 315                 320

Leu Lys Asp Asn Leu Glu Ala Asn Ile Leu Ala Ala Leu Val Asn Thr
                325                 330                 335

Ala His Gly Glu Ala Ala Ser Lys Ile Lys Gln Leu Asp Gln His Tyr
            340                 345                 350

Ile Val His Lys Ile Ala His Ala Ile Ala Gly Cys Ala Ala Ala Ala
        355                 360                 365

Ala Asn Lys Gly Lys Cys Gln Asp Gly Ala Ile Gly Ala Ala Val Gly
    370                 375                 380

Glu Ile Val Gly Glu Ala Leu Thr Asn Gly Lys Asn Pro Ala Thr Leu
385                 390                 395                 400

Thr Ala Lys Glu Arg Glu Gln Ile Leu Ala Tyr Ser Lys Leu Val Ala
                405                 410                 415

Gly Thr Val Ser Gly Val Val Gly Gly Asp Val Asn Thr Ala Ala Asn
            420                 425                 430

Ala Ala Lys Val Ala Ile Glu Asn Asn Leu Leu Ser Gln Glu Glu Tyr
        435                 440                 445
```

```
Ala Leu Arg Glu Lys Leu Ile Lys Lys Ala Lys Gly Lys Gly Leu Leu
    450                 455                 460

Ser Leu Asp Trp Gly Ser Leu Thr Glu Gln Glu Ala Arg Gln Phe Ile
465                 470                 475                 480

Tyr Leu Ile Glu Lys Asp Arg Tyr Ser Asn Gln Leu Leu Asp Arg Tyr
                485                 490                 495

Gln Lys Asn Pro Ser Ser Leu Asn Asn Gln Glu Lys Asn Ile Leu Ala
            500                 505                 510

Tyr Phe Ile Asn Gln Thr Ser Gly Gly Asn Thr Ala Trp Ala Ala Ser
        515                 520                 525

Ile Leu Lys Thr Pro Gln Ser Met Gly Asn Leu Thr Ile Pro Ser Lys
    530                 535                 540

Asp Ile Asn Asn Thr Leu Ser Lys Ala Tyr Gln Thr Leu Ser Arg Tyr
545                 550                 555                 560

Asp Ser Phe Asp Tyr Lys Ser Ala Val Ala Ala Gln Pro Ala Leu Tyr
                565                 570                 575

Leu Leu Asn Gly Pro Leu Gly Phe Ser Val Lys Ala Ala Thr Val Ala
            580                 585                 590

Ala Gly Gly Tyr Asn Ile Gly Gln Gly Ala Lys Ala Ile Ser Asn Gly
        595                 600                 605

Glu Tyr Leu His Gly Thr Val Gln Val Val Asn Gly Thr Leu Met Val
    610                 615                 620

Ala Gly Ser Val Ser Ala Gln Ala Ala Ile Ser Ala Lys Pro Ala Pro
625                 630                 635                 640

Val Thr Arg Tyr Leu Ser Asn Asp Ser Ala Pro Ala Leu Arg Gln Ala
                645                 650                 655

Leu Thr Ala Glu Ser Gln Arg Ile Arg Met Lys Leu Pro Glu Glu Tyr
            660                 665                 670

Arg Gln Ile Gly Asn Leu Ala Ile Ala Lys Ile Asp Val Lys Gly Leu
        675                 680                 685

Pro Gln Arg Met Glu Ala Phe Ser Ser Phe Gln Lys Gly Glu His Gly
    690                 695                 700

Phe Ile Ser Leu Pro Glu Thr Lys Ile Phe Lys Pro Ile Ser Val Asp
705                 710                 715                 720

Lys Tyr His Asn Ile Ala Ser Pro Pro Arg Gly Thr Leu Arg Asn Ile
                725                 730                 735

Asp Gly Glu Tyr Lys Leu Leu Glu Thr Ile Ala Gln Gln Leu Gly Asn
            740                 745                 750

Asn Arg Asn Val Ser Gly Arg Ile Asp Leu Phe Thr Glu Leu Lys Ala
        755                 760                 765

Cys Gln Ser Cys Ser Asn Val Ile Leu Glu Phe Arg Asn Arg Tyr Pro
    770                 775                 780

Asn Ile Gln Leu Asn Ile Phe Thr Gly Lys
785                 790

<210> SEQ ID NO 27
<211> LENGTH: 621
<212> TYPE: DNA
<213> ORGANISM: Neisseria meningitidis

<400> SEQUENCE: 27

ttgctgggtg tggttccggg tatcggtgaa tcgatacagg cctataaagt agcgaaagcg      60

gcaaaaaatt tacaaggcat gaaaaaagcc ttggacaagg cagcaaccgt tgccactgca     120

cagggctatg tcagtaaaac caaaatcaaa atcggtcaaa ctgaattaag ggttactgca     180
```

-continued

```
gcaactgaca aacaattgct gaaagctatt ggcgaaggaa gggacacgac aggtaaaatg    240

accgagcagt tatttgactc tttagctaaa caaaatggct tcagagtgct ttcgggcggc    300

aaatacggcg gaaataacgg ttttgatcat gtatggcagg ctgccgatgg tagtgtcgtt    360

ttgattgtag aaagtaagca gattaggaac ggtacggtac agctgaatcc gaatggtgcg    420

ggtggatata cgcaaatgag tgaggattgg attagacaag ttttagatca attacccgat    480

ggtagtcccg ctaaagctgc tgtcttcaaa gcaaataaga acggcacatt aaaaacagca    540

atagcaggcg ttgatcgtca aacaggtaag gccgttattc ttcctgtcaa agttccttct    600

aaaaccaata taaggagata a                                              621
```

<210> SEQ ID NO 28
<211> LENGTH: 206
<212> TYPE: PRT
<213> ORGANISM: Neisseria meningitidis

<400> SEQUENCE: 28

```
Met Leu Gly Val Val Pro Gly Ile Gly Glu Ser Ile Gln Ala Tyr Lys
 1               5                  10                  15

Val Ala Lys Ala Ala Lys Asn Leu Gln Gly Met Lys Lys Ala Leu Asp
            20                  25                  30

Lys Ala Ala Thr Val Ala Thr Ala Gln Gly Tyr Val Ser Lys Thr Lys
        35                  40                  45

Ile Lys Ile Gly Gln Thr Glu Leu Arg Val Thr Ala Ala Thr Asp Lys
    50                  55                  60

Gln Leu Leu Lys Ala Ile Gly Glu Gly Arg Asp Thr Thr Gly Lys Met
65                  70                  75                  80

Thr Glu Gln Leu Phe Asp Ser Leu Ala Lys Gln Asn Gly Phe Arg Val
                85                  90                  95

Leu Ser Gly Gly Lys Tyr Gly Gly Asn Asn Gly Phe Asp His Val Trp
            100                 105                 110

Gln Ala Ala Asp Gly Ser Val Val Leu Ile Val Glu Ser Lys Gln Ile
        115                 120                 125

Arg Asn Gly Thr Val Gln Leu Asn Pro Asn Gly Ala Gly Gly Tyr Thr
    130                 135                 140

Gln Met Ser Glu Asp Trp Ile Arg Gln Val Leu Asp Gln Leu Pro Asp
145                 150                 155                 160

Gly Ser Pro Ala Lys Ala Ala Val Phe Lys Ala Asn Lys Asn Gly Thr
                165                 170                 175

Leu Lys Thr Ala Ile Ala Gly Val Asp Arg Gln Thr Gly Lys Ala Val
            180                 185                 190

Ile Leu Pro Val Lys Val Pro Ser Lys Thr Asn Ile Arg Arg
        195                 200                 205
```

<210> SEQ ID NO 29
<211> LENGTH: 4509
<212> TYPE: DNA
<213> ORGANISM: Neisseria meningitidis

<400> SEQUENCE: 29

```
atgaatgagg gtgaagttgt tttaacacca gaacaaatcc aaaccttgcg tggttatgct     60

ttccgtggcg atacctatgg cggttggcgt tatttggcta atttgggtga ccgttatgcg    120

gatgatgctg ctgcaattgt cggtaaggat gcaaacttaa atggtttgaa tttatggatg    180

aaaaaaggtg tggaaaacct atgggatgat acggtcggta aaaagacccg tttagagaaa    240
```

-continued

```
tttgatcggg ttgcattgca acatttcagc caatatgtag atctaattaa tgaaaataat    300

ggtagattac ctaacactag tgaaattgag agaagttact ataaagccgt taccgaaaat    360

ggtgtttctt ctagtgcagc tattgattta gttattaatc gctcacttcc ggatatggca    420

gatggttatt gggcattagg tttggggata gaagccgaac gtatccacaa tgcgcaagca    480

gtaaataatc cgaacggtag cgaatgggat aatagaaagc agttaatatc tgctttagat    540

aaaggatttg atggatcttt taaagagaag cattttactt ttttacaatc tgtgataatg    600

gatgtaacaa agttaggtgt tgaatataca atagatggtt ggcaaaaaat tggaggttgg    660

ggtaatggga taatcaatga tttatataaa agtgttgcaa aaagagagtg gactggaata    720

tttgagatcg ttaataataa catcaagcaa tttagagatc tgttcccaaa tccggaaggc    780

tggatcgatg atggtcacca atgtttcgct ccttgggtta aagaaactaa aaaacgcaat    840

ggcaaatatc atgtctacga ccccctcgcc ctagatttgg acggagacgg tatagaaacc    900

gttgccacca aaggctttgc aggcagctta tttgatcaca ccaacaacgg tatccgcacc    960

gccaccggtt gggtttctgc cgatgacggt ttactcgtcc gcgatttgaa cggcaacggc   1020

atcatcgaca acggtgcgga actcttcggc gacaacacca aactggcaga cggttctttt   1080

gccaaacacg gctatgcagc tttggccgaa ttggattcaa acggcgacaa catcatcaac   1140

gcggcagacg ccgcattcca aaccctgcgt gtatggcagg atctcaatca ggacggcatt   1200

tcccaaacca acgaactccg cacccttgaa gaattgggta ttcaatcttt ggatctcgcc   1260

tataaagatg taaataaaaa tctcggtaac ggtaacactt tggctcagca aggtagctac   1320

accaaaacaa acggtacaac cgcaaaaatg gggggattac ttttagcagc cgacaatctg   1380

cacagccgct tcaaagacaa agtggaactc actgccaaac aggcaaaagc cgccaatctt   1440

gcgggcattg gtcgtctgcg cgatttgcgc gaagctgccg cattgtccgg cgatttggcc   1500

aatatgctga aagcttattc tgccgccgaa actaaagaag cacagttggc attgttagat   1560

aatttgattc acaaatgggc ggaaaccgat tcgaactggg gcaaaaaatc gccaatgcga   1620

ctttcaaccg attggacgca aacggctaat gaaggtattg cactgacacc atcccaagta   1680

gcacaactaa aaaagaacgc tttagtttcc ctttctgata aagctaaagc agctattgac   1740

gccgcccgcg accgcattgc cgtgcttgat gcctacacgg ggcaggattc cagcacactc   1800

tattacatga gcgaagaaga cgcgcttaat atcgtcaaag taaccaacga tacatacgac   1860

catctcgcca aaaacatcta ccaaaacctg ttgttccaaa cccgtttgca gccatatttg   1920

aatcaaatca gtttcaaaat ggaaaatgat acgttcactt tggattttag tggtcttgtt   1980

caagcattta accatgtcaa agaaactaat ccgcaaaaag cttttgtgga tttggccgag   2040

atgcttgcat atggcgaact tcgttcttgg tatgaaggcc gaagactaat ggccgattat   2100

gtggaggagg caaaaaaagc aggtaaattt gaagattacc agaaagtgtt gggtcaggag   2160

accgttgcat tattagctaa aacatcgggt acgcaagcag atgatatcct gcaaaatgta   2220

ggctttggtc ataataaaaa tgtttcttta tatggtaatg acggcaacga cactctgatc   2280

ggcggtgccg gtaatgatta cttggagggc ggcagcggtt cggatactta tgtcttcggc   2340

aaaggcttcg gtcaggatac ggtctataat tacgactacg ctaccggacg caaagacatc   2400

atccgcttta ccgacggtat tacagccgat atgctgactt ttacccgaga gggcaaccat   2460

cttcttatca aggcaaaaga cggcagtgga caagtgactg ttcagtacta tttccagaac   2520

gatggctcag gagcttaccg tatcgacgag attcatttcg ataacggcaa agtactggat   2580

gttgccactg tcaaagaact ggtacagcaa tccaccgacg gctcggacag attgtatgcc   2640
```

-continued

```
taccaatccg gaaatacctt aaatggcgga ttgggcgatg actatctgta cggtgccgac   2700
ggggatgacc tgctgaatgg tgatgcaggc aacgacagta tctacagtgg caatggcaat   2760
gatacgctcg atggaggaga aggcaacgac gccctgtacg gctataatgg taacgatgta   2820
ctgaatggtg gcgaaggcaa tgatcatttg aacggcgaag acggtaacga cactctgatc   2880
ggcggtgccg gtaatgatta cttggagggc ggcagcggtt cggatactta tgtcttcggc   2940
aaaggcttcg gtcaggatac ggtctataat tacgactacg ctaccggacg caaagacatc   3000
atccgcttta ccgacggtat tacagccgat atgctgactt ttacccgaga gggcaaccat   3060
cttcttatca aggcaaaaga cggcagtgga caagtgactg ttcagtccta tttccagaac   3120
gatggctcag gtgcttaccg tatcgatgag attcatttcg ataacggcaa agtactggat   3180
gttgccactg tcaaagaact ggtacagcaa tccaccgacg gctcggacag attgtatgcc   3240
taccaatccg gaaatacctt aaatggcgga ttgggcgatg actatctgta cggtgccgac   3300
ggggatgacc tgctgaatgg tgatgcaggc aacgacagta tctacagtgg caatggcaat   3360
gatacgctcg atggaggaga aggcaacgac gccctgtacg gctataatgg taacgatgta   3420
ctgaatggtg gcgaaggcaa tgatcatttg aacggcgaag acggtaacga cactctgatc   3480
ggcggtgcag gcaatgatta cttggagggc ggcagcggtt cggatactta tgtcttcggc   3540
gaaggcttcg gtcaggatac ggtctataat tacgactacg ctaccggacg caaagacatc   3600
atccgcttta ccgacggtat tacagccgat atgctgactt ttacccgaga gggcaaccat   3660
cttcttatca aggcaaaaga cggcagtgga caagtgactg ttcagtccta tttccagaac   3720
gatggctcag gtgcttaccg tatcgatgag attcatttcg ataacggcaa agtactggat   3780
gttgccactg tcaaagaact ggtacagcaa tccaccgacg gctcggacag attgtatgcc   3840
taccaatccg gaaatacctt aaatggcgga ttgggcgatg actatctgta cggtgccgac   3900
ggggatgacc tgctgaatgg tgatgcaggc aacgacagta tctacagtgg caatggcaat   3960
gatacgctcg atggaggaga aggcaacgac gccctgtacg gctataatgg taacgatgta   4020
ctgaatggtg gcgaaggcaa tgatcatttg aacggcgaag acggtaacga cactctgatc   4080
ggcggtgccg gtaatgatta cttggagggc ggcagcggtt cggatactta tgtcttcggc   4140
aaaggcttcg gtcaggatac ggtctataat taccatgtgg ataaaaactc tgacactatg   4200
cactttaaag gatttaaagc agcagatgtt cattttatcc gttccggaag tgatttggtg   4260
cttagcgctt ctgaacaaga caacgtacgt atttccggat tcttctatgg tgaaaaccat   4320
cgtgtagata catttgtctt tgatgatgca gctatcagta atccagattt tgccaagtat   4380
attaatgctg gcaataattt ggtacagtct atgtctgtgt tcggttctaa tactgctgcg   4440
acaggaggaa atgtggatgc caatacacaa tccgtacagc agccgttatt ggtaacgcca   4500
tctgcataa                                                           4509
```

<210> SEQ ID NO 30
<211> LENGTH: 1502
<212> TYPE: PRT
<213> ORGANISM: Neisseria meningitidis

<400> SEQUENCE: 30

```
Met Asn Glu Gly Glu Val Val Leu Thr Pro Glu Gln Ile Gln Thr Leu
 1               5                  10                  15

Arg Gly Tyr Ala Phe Arg Gly Asp Thr Tyr Gly Gly Trp Arg Tyr Leu
            20                  25                  30

Ala Asn Leu Gly Asp Arg Tyr Ala Asp Asp Ala Ala Ala Ile Val Gly
        35                  40                  45
```

-continued

```
Lys Asp Ala Asn Leu Asn Gly Leu Asn Leu Trp Met Lys Lys Gly Val
    50                  55                  60

Glu Asn Leu Trp Asp Asp Thr Val Gly Lys Lys Thr Arg Leu Glu Lys
65                  70                  75                  80

Phe Asp Arg Val Ala Leu Gln His Phe Ser Gln Tyr Val Asp Leu Ile
                85                  90                  95

Asn Glu Asn Asn Gly Arg Leu Pro Asn Thr Ser Glu Ile Glu Arg Ser
            100                 105                 110

Tyr Tyr Lys Ala Val Thr Glu Asn Gly Val Ser Ser Ser Ala Ala Ile
        115                 120                 125

Asp Leu Val Ile Asn Arg Ser Leu Pro Asp Met Ala Asp Gly Tyr Trp
    130                 135                 140

Ala Leu Gly Leu Gly Ile Glu Ala Glu Arg Ile His Asn Ala Gln Ala
145                 150                 155                 160

Val Asn Asn Pro Asn Gly Ser Glu Trp Asp Asn Arg Lys Gln Leu Ile
                165                 170                 175

Ser Ala Leu Asp Lys Gly Phe Asp Gly Ser Phe Lys Glu Lys His Phe
            180                 185                 190

Thr Phe Leu Gln Ser Val Ile Met Asp Val Thr Lys Leu Gly Val Glu
        195                 200                 205

Tyr Thr Ile Asp Gly Trp Gln Lys Ile Gly Gly Trp Gly Asn Gly Ile
    210                 215                 220

Ile Asn Asp Leu Tyr Lys Ser Val Ala Lys Arg Glu Trp Thr Gly Ile
225                 230                 235                 240

Phe Glu Ile Val Asn Asn Asn Ile Lys Gln Phe Arg Asp Leu Phe Pro
                245                 250                 255

Asn Pro Glu Gly Trp Ile Asp Asp Gly His Gln Cys Phe Ala Pro Trp
            260                 265                 270

Val Lys Glu Thr Lys Lys Arg Asn Gly Lys Tyr His Val Tyr Asp Pro
        275                 280                 285

Leu Ala Leu Asp Leu Asp Gly Asp Gly Ile Glu Thr Val Ala Thr Lys
    290                 295                 300

Gly Phe Ala Gly Ser Leu Phe Asp His Thr Asn Asn Gly Ile Arg Thr
305                 310                 315                 320

Ala Thr Gly Trp Val Ser Ala Asp Asp Gly Leu Leu Val Arg Asp Leu
                325                 330                 335

Asn Gly Asn Gly Ile Ile Asp Asn Gly Ala Glu Leu Phe Gly Asp Asn
            340                 345                 350

Thr Lys Leu Ala Asp Gly Ser Phe Ala Lys His Gly Tyr Ala Ala Leu
        355                 360                 365

Ala Glu Leu Asp Ser Asn Gly Asp Asn Ile Ile Asn Ala Ala Asp Ala
    370                 375                 380

Ala Phe Gln Thr Leu Arg Val Trp Gln Asp Leu Asn Gln Asp Gly Ile
385                 390                 395                 400

Ser Gln Thr Asn Glu Leu Arg Thr Leu Glu Glu Leu Gly Ile Gln Ser
                405                 410                 415

Leu Asp Leu Ala Tyr Lys Asp Val Asn Lys Asn Leu Gly Asn Gly Asn
            420                 425                 430

Thr Leu Ala Gln Gln Gly Ser Tyr Thr Lys Thr Asn Gly Thr Thr Ala
        435                 440                 445

Lys Met Gly Asp Leu Leu Leu Ala Ala Asp Asn Leu His Ser Arg Phe
    450                 455                 460

Lys Asp Lys Val Glu Leu Thr Ala Lys Gln Ala Lys Ala Ala Asn Leu
```

-continued

```
465                 470                 475                 480

Ala Gly Ile Gly Arg Leu Arg Asp Leu Arg Glu Ala Ala Ala Leu Ser
                485                 490                 495

Gly Asp Leu Ala Asn Met Leu Lys Ala Tyr Ser Ala Ala Glu Thr Lys
            500                 505                 510

Glu Ala Gln Leu Ala Leu Leu Asp Asn Leu Ile His Lys Trp Ala Glu
        515                 520                 525

Thr Asp Ser Asn Trp Gly Lys Lys Ser Pro Met Arg Leu Ser Thr Asp
    530                 535                 540

Trp Thr Gln Thr Ala Asn Glu Gly Ile Ala Leu Thr Pro Ser Gln Val
545                 550                 555                 560

Ala Gln Leu Lys Lys Asn Ala Leu Val Ser Leu Ser Asp Lys Ala Lys
                565                 570                 575

Ala Ala Ile Asp Ala Ala Arg Asp Arg Ile Ala Val Leu Asp Ala Tyr
            580                 585                 590

Thr Gly Gln Asp Ser Ser Thr Leu Tyr Tyr Met Ser Glu Glu Asp Ala
        595                 600                 605

Leu Asn Ile Val Lys Val Thr Asn Asp Thr Tyr Asp His Leu Ala Lys
    610                 615                 620

Asn Ile Tyr Gln Asn Leu Leu Phe Gln Thr Arg Leu Gln Pro Tyr Leu
625                 630                 635                 640

Asn Gln Ile Ser Phe Lys Met Glu Asn Asp Thr Phe Thr Leu Asp Phe
                645                 650                 655

Ser Gly Leu Val Gln Ala Phe Asn His Val Lys Glu Thr Asn Pro Gln
            660                 665                 670

Lys Ala Phe Val Asp Leu Ala Glu Met Leu Ala Tyr Gly Glu Leu Arg
        675                 680                 685

Ser Trp Tyr Glu Gly Arg Arg Leu Met Ala Asp Tyr Val Glu Glu Ala
    690                 695                 700

Lys Lys Ala Gly Lys Phe Glu Asp Tyr Gln Lys Val Leu Gly Gln Glu
705                 710                 715                 720

Thr Val Ala Leu Leu Ala Lys Thr Ser Gly Thr Gln Ala Asp Asp Ile
                725                 730                 735

Leu Gln Asn Val Gly Phe Gly His Asn Lys Asn Val Ser Leu Tyr Gly
            740                 745                 750

Asn Asp Gly Asn Asp Thr Leu Ile Gly Gly Ala Gly Asn Asp Tyr Leu
        755                 760                 765

Glu Gly Gly Ser Gly Ser Asp Thr Tyr Val Phe Gly Lys Gly Phe Gly
    770                 775                 780

Gln Asp Thr Val Tyr Asn Tyr Asp Tyr Ala Thr Gly Arg Lys Asp Ile
785                 790                 795                 800

Ile Arg Phe Thr Asp Gly Ile Thr Ala Asp Met Leu Thr Phe Thr Arg
                805                 810                 815

Glu Gly Asn His Leu Leu Ile Lys Ala Lys Asp Gly Ser Gly Gln Val
            820                 825                 830

Thr Val Gln Tyr Tyr Phe Gln Asn Asp Gly Ser Gly Ala Tyr Arg Ile
        835                 840                 845

Asp Glu Ile His Phe Asp Asn Gly Lys Val Leu Asp Val Ala Thr Val
    850                 855                 860

Lys Glu Leu Val Gln Gln Ser Thr Asp Gly Ser Asp Arg Leu Tyr Ala
865                 870                 875                 880

Tyr Gln Ser Gly Asn Thr Leu Asn Gly Gly Leu Gly Asp Asp Tyr Leu
                885                 890                 895
```

```
Tyr Gly Ala Asp Gly Asp Asp Leu Leu Asn Gly Asp Ala Gly Asn Asp
            900                 905                 910

Ser Ile Tyr Ser Gly Asn Gly Asn Asp Thr Leu Asp Gly Gly Glu Gly
        915                 920                 925

Asn Asp Ala Leu Tyr Gly Tyr Asn Gly Asn Asp Val Leu Asn Gly Gly
    930                 935                 940

Glu Gly Asn Asp His Leu Asn Gly Glu Asp Gly Asn Asp Thr Leu Ile
945                 950                 955                 960

Gly Gly Ala Gly Asn Asp Tyr Leu Glu Gly Gly Ser Gly Ser Asp Thr
                965                 970                 975

Tyr Val Phe Gly Lys Gly Phe Gly Gln Asp Thr Val Tyr Asn Tyr Asp
            980                 985                 990

Tyr Ala Thr Gly Arg Lys Asp Ile Ile Arg Phe Thr Asp Gly Ile Thr
        995                 1000                1005

Ala Asp Met Leu Thr Phe Thr Arg Glu Gly Asn His Leu Leu Ile Lys
    1010                1015                1020

Ala Lys Asp Gly Ser Gly Gln Val Thr Val Gln Ser Tyr Phe Gln Asn
1025                1030                1035                1040

Asp Gly Ser Gly Ala Tyr Arg Ile Asp Glu Ile His Phe Asp Asn Gly
                1045                1050                1055

Lys Val Leu Asp Val Ala Thr Val Lys Glu Leu Val Gln Gln Ser Thr
            1060                1065                1070

Asp Gly Ser Asp Arg Leu Tyr Ala Tyr Gln Ser Gly Asn Thr Leu Asn
        1075                1080                1085

Gly Gly Leu Gly Asp Asp Tyr Leu Tyr Gly Ala Asp Gly Asp Asp Leu
    1090                1095                1100

Leu Asn Gly Asp Ala Gly Asn Asp Ser Ile Tyr Ser Gly Asn Gly Asn
1105                1110                1115                1120

Asp Thr Leu Asp Gly Gly Glu Gly Asn Asp Ala Leu Tyr Gly Tyr Asn
                1125                1130                1135

Gly Asn Asp Val Leu Asn Gly Gly Glu Gly Asn Asp His Leu Asn Gly
            1140                1145                1150

Glu Asp Gly Asn Asp Thr Leu Ile Gly Gly Ala Gly Asn Asp Tyr Leu
        1155                1160                1165

Glu Gly Gly Ser Gly Ser Asp Thr Tyr Val Phe Gly Glu Gly Phe Gly
    1170                1175                1180

Gln Asp Thr Val Tyr Asn Tyr Asp Tyr Ala Thr Gly Arg Lys Asp Ile
1185                1190                1195                1200

Ile Arg Phe Thr Asp Gly Ile Thr Ala Asp Met Leu Thr Phe Thr Arg
                1205                1210                1215

Glu Gly Asn His Leu Leu Ile Lys Ala Lys Asp Gly Ser Gly Gln Val
            1220                1225                1230

Thr Val Gln Ser Tyr Phe Gln Asn Asp Gly Ser Gly Ala Tyr Arg Ile
        1235                1240                1245

Asp Glu Ile His Phe Asp Asn Gly Lys Val Leu Asp Val Ala Thr Val
    1250                1255                1260

Lys Glu Leu Val Gln Gln Ser Thr Asp Gly Ser Asp Arg Leu Tyr Ala
1265                1270                1275                1280

Tyr Gln Ser Gly Asn Thr Leu Asn Gly Gly Leu Gly Asp Asp Tyr Leu
                1285                1290                1295

Tyr Gly Ala Asp Gly Asp Asp Leu Leu Asn Gly Asp Ala Gly Asn Asp
            1300                1305                1310

Ser Ile Tyr Ser Gly Asn Gly Asn Asp Thr Leu Asp Gly Gly Glu Gly
        1315                1320                1325
```

Asn Asp Ala Leu Tyr Gly Tyr Asn Gly Asn Asp Val Leu Asn Gly Gly
    1330                1335                1340

Glu Gly Asn Asp His Leu Asn Gly Glu Asp Gly Asn Asp Thr Leu Ile
1345                1350                1355                1360

Gly Gly Ala Gly Asn Asp Tyr Leu Glu Gly Gly Ser Gly Ser Asp Thr
                1365                1370                1375

Tyr Val Phe Gly Lys Gly Phe Gly Gln Asp Thr Val Tyr Asn Tyr His
            1380                1385                1390

Val Asp Lys Asn Ser Asp Thr Met His Phe Lys Gly Phe Lys Ala Ala
        1395                1400                1405

Asp Val His Phe Ile Arg Ser Gly Ser Asp Leu Val Leu Ser Ala Ser
    1410                1415                1420

Glu Gln Asp Asn Val Arg Ile Ser Gly Phe Phe Tyr Gly Glu Asn His
1425                1430                1435                1440

Arg Val Asp Thr Phe Val Phe Asp Asp Ala Ala Ile Ser Asn Pro Asp
                1445                1450                1455

Phe Ala Lys Tyr Ile Asn Ala Gly Asn Asn Leu Val Gln Ser Met Ser
            1460                1465                1470

Val Phe Gly Ser Asn Thr Ala Ala Thr Gly Gly Asn Val Asp Ala Asn
        1475                1480                1485

Thr Gln Ser Val Gln Gln Pro Leu Leu Val Thr Pro Ser Ala
    1490                1495                1500

<210> SEQ ID NO 31
<211> LENGTH: 774
<212> TYPE: DNA
<213> ORGANISM: Neisseria meningitidis

<400> SEQUENCE: 31
atgaacgcca ttgcagacgt gcaatccagc cgcgatttac gcaacctgcc gattaatcag 60
gtcggcatca aagacctgcg ctttccaatc tcccttaaaa gcaaagaagg cgaacaatcc 120
accgtcgccc acctgaccat gacggttttc ctgcctgccg accaaaaagg cacgcatatg 180
tcgcgctttg tcgccctgat ggaaaaacaa accgaagcct tggatttcga tacgctgcac 240
aaactgaccg tcgatatggt tgccctgttg gattcgcatt ccggaaaaat cagcgtttgc 300
ttcccgtttt tccgcaagaa aagtgcgccc gtctccggca tccaatcgct gcttgactat 360
gatgttaccc tgaccggcga aatcaaaaac ggtacataca gccacaatct gaaagtaatg 420
gttccggtta cttcattgtg tccgtgttcc aaagaaattt cccaatacgg cgcacacaac 480
caacgttcgc atgtgactgt cagcctgatt gcaaacgcgg atgtaggtat tgaagaaatc 540
atcgattacg ttgaagcgca agcaagctgc caactctacg gtttgctcaa acgccccgat 600
gaaaaatatg ttaccgaaaa agcctacgaa aacccgaaat tcgtggaaga tatggtgcgt 660
gatgtcgcta cttcgctgat cgccgacaaa cgcatcaaga gtttcgttgt cgagagcgag 720
aatttcgagt ctatccacaa ccattcggct tatgcctata tcgcctaccc gtag 774

<210> SEQ ID NO 32
<211> LENGTH: 257
<212> TYPE: PRT
<213> ORGANISM: Neisseria meningitidis

<400> SEQUENCE: 32

Met Asn Ala Ile Ala Asp Val Gln Ser Ser Arg Asp Leu Arg Asn Leu
 1               5                  10                  15

Pro Ile Asn Gln Val Gly Ile Lys Asp Leu Arg Phe Pro Ile Ser Leu

```
            20                  25                  30

Lys Ser Lys Glu Gly Glu Gln Ser Thr Val Ala His Leu Thr Met Thr
        35                  40                  45

Val Phe Leu Pro Ala Asp Gln Lys Gly Thr His Met Ser Arg Phe Val
    50                  55                  60

Ala Leu Met Glu Lys Gln Thr Glu Ala Leu Asp Phe Asp Thr Leu His
65                  70                  75                  80

Lys Leu Thr Val Asp Met Val Ala Leu Leu Asp Ser His Ser Gly Lys
                85                  90                  95

Ile Ser Val Cys Phe Pro Phe Phe Arg Lys Lys Ser Ala Pro Val Ser
            100                 105                 110

Gly Ile Gln Ser Leu Leu Asp Tyr Asp Val Thr Leu Thr Gly Glu Ile
        115                 120                 125

Lys Asn Gly Thr Tyr Ser His Asn Leu Lys Val Met Val Pro Val Thr
    130                 135                 140

Ser Leu Cys Pro Cys Ser Lys Glu Ile Ser Gln Tyr Gly Ala His Asn
145                 150                 155                 160

Gln Arg Ser His Val Thr Val Ser Leu Ile Ala Asn Ala Asp Val Gly
                165                 170                 175

Ile Glu Glu Ile Ile Asp Tyr Val Glu Ala Gln Ala Ser Cys Gln Leu
            180                 185                 190

Tyr Gly Leu Leu Lys Arg Pro Asp Glu Lys Tyr Val Thr Glu Lys Ala
        195                 200                 205

Tyr Glu Asn Pro Lys Phe Val Glu Asp Met Val Arg Asp Val Ala Thr
    210                 215                 220

Ser Leu Ile Ala Asp Lys Arg Ile Lys Ser Phe Val Val Glu Ser Glu
225                 230                 235                 240

Asn Phe Glu Ser Ile His Asn His Ser Ala Tyr Ala Tyr Ile Ala Tyr
                245                 250                 255

Pro


<210> SEQ ID NO 33
<211> LENGTH: 714
<212> TYPE: DNA
<213> ORGANISM: Neisseria meningitidis

<400> SEQUENCE: 33

atgttgttcc gtaaaacgac cgccgccgtt ttggcggcaa ccttgatgct gaatggctgt      60

acggcaatga tgtggggcat gaacgacccg ttcagccaaa cgaccgccta taaacacgtt     120

gacaaagacc aaatccgcgc cttcggtgtg gttgccaaag acaatgccca attggaaaag     180

ggcagcctgg tgatgatggg cgggaaatac tggttcgtcg tcaatcctga agattcggcg     240

aagctgacgg gcattttgaa ggccgggttg gacaagcagt ttcaaatggt tgagcccaac     300

ccgcgctttg cctaccaagc cctgccggtc aaactcgaat cgcccgccag ccagaatttc     360

agtaccgacg acctttgcct gcgctacgat accgacagac ctgccgacat cgccaagctg     420

aaacagcttg agtttgaagc ggtcgaactc gacaatcgga ccatttacac gcgctgcgtc     480

tccgccaaag gcaaatacta cgccacaccg caaaaactga acgccgatta tcattttgag     540

caaagtgtgc ctgccgatat ttattacacg gttacgaaaa aacataccga caaatccaag     600

ttgtttgaaa atattgcata tacgcccacc acgttgatac tggatgcggc gggtgcggta     660

ctggtcttgc ctatggcggc gttgattgca gccgcgaatt cctcagacaa atga           714


<210> SEQ ID NO 34
```

<211> LENGTH: 237
<212> TYPE: PRT
<213> ORGANISM: Neisseria meningitidis

<400> SEQUENCE: 34

```
Met Leu Phe Arg Lys Thr Thr Ala Ala Val Leu Ala Ala Thr Leu Met
 1               5                  10                  15

Leu Asn Gly Cys Thr Ala Met Met Trp Gly Met Asn Asp Pro Phe Ser
            20                  25                  30

Gln Thr Thr Ala Tyr Lys His Val Asp Lys Asp Gln Ile Arg Ala Phe
        35                  40                  45

Gly Val Val Ala Lys Asp Asn Ala Gln Leu Glu Lys Gly Ser Leu Val
    50                  55                  60

Met Met Gly Gly Lys Tyr Trp Phe Val Val Asn Pro Glu Asp Ser Ala
65                  70                  75                  80

Lys Leu Thr Gly Ile Leu Lys Ala Gly Leu Asp Lys Gln Phe Gln Met
                85                  90                  95

Val Glu Pro Asn Pro Arg Phe Ala Tyr Gln Ala Leu Pro Val Lys Leu
            100                 105                 110

Glu Ser Pro Ala Ser Gln Asn Phe Ser Thr Asp Asp Leu Cys Leu Arg
        115                 120                 125

Tyr Asp Thr Asp Arg Pro Ala Asp Ile Ala Lys Leu Lys Gln Leu Glu
    130                 135                 140

Phe Glu Ala Val Glu Leu Asp Asn Arg Thr Ile Tyr Thr Arg Cys Val
145                 150                 155                 160

Ser Ala Lys Gly Lys Tyr Tyr Ala Thr Pro Gln Lys Leu Asn Ala Asp
                165                 170                 175

Tyr His Phe Glu Gln Ser Val Pro Ala Asp Ile Tyr Tyr Thr Val Thr
            180                 185                 190

Lys Lys His Thr Asp Lys Ser Lys Leu Phe Glu Asn Ile Ala Tyr Thr
        195                 200                 205

Pro Thr Thr Leu Ile Leu Asp Ala Ala Gly Ala Val Leu Val Leu Pro
    210                 215                 220

Met Ala Ala Leu Ile Ala Ala Ala Asn Ser Ser Asp Lys
225                 230                 235
```

<210> SEQ ID NO 35
<211> LENGTH: 1209
<212> TYPE: DNA
<213> ORGANISM: Neisseria meningitidis

<400> SEQUENCE: 35

```
atgtccgaac cgttgcacgt cctcgtcatc ccctcatggt atccgcaatc cgaacaggat      60

gtggacggga ttttttttca aaatcaggca ctggcattgc agagaaaagg catcaaaact     120

gccgtgcttg caccgatgtt ccgctacttg cggaaagaaa cagcaagcat cctgaccggt     180

ccttacggtt ttgcccaata ccggcaaaaa ggtttggaca tctatgcatg gcacggcatg     240

tatttcttcc cccgttttcc gctaatcgac atcgaccgca tccgctgggt gcgggcagga     300

ttaaaggcct ttgagcgcta tatcggggaa aacggcattc ccgacatcat ccatgcccac     360

tgtatgaact atgccggcat acttgccttc aagatttccc aaaaatacgg catcccctat     420

gtcgtcacgg aacacagcag caccattacg cgcggtttgg tgcgtccgca ccaatggcag     480

cctatgaaaa atgcggcggc acacgcctcc gcactgctcg ctgtcagctg ccgtttcgcc     540

caagtcctgc aacataaata cggcactaca tggcaatatc tgcctaacat tctgggtaac     600

atctttaccc gagccttcaa tcccccgcaa atcaaccgtc cggacaaata ttttaccttc     660
```

```
tgcactatct cccatctgcg ccggctaaaa ggacatgatg tcctcctgtc cgcctttgcc    720

cgtgctttgg caaaacaccc aaacctccgt ttgaatatcg gcggcagcgg acaagaagaa    780

acaagcctga aacggcaggc acgtcagttg ggaattgccc atgccgttac atttttgggc    840

gcattgcagc ccgaagcagt cttggatttg atgaggaaca gcgacgcatt cgtccttgcc    900

agccgcacag aaaccttcgg cgtggtctat atcgaagcac tgtcccaagg attgcccgtc    960

attgcaacac gctgcggcgg tgcggaatct attgtttcag acggcaacgg atatttggtt   1020

cctgttgacg acgacgatgc ccttgccgac gcactcatca aaatgtatga acaccactct   1080

gattttgaac ctgaccgact tagggaaaac tgtctgaacg aatttggcga agataccgtt   1140

ataggcaagt tgatcggcat tttccgacag gcaatcgcag aatacggtaa gaaaataccg   1200

gtgaaatag                                                           1209


<210> SEQ ID NO 36
<211> LENGTH: 402
<212> TYPE: PRT
<213> ORGANISM: Neisseria meningitidis

<400> SEQUENCE: 36

Met Ser Glu Pro Leu His Val Leu Val Ile Pro Ser Trp Tyr Pro Gln
 1               5                  10                  15

Ser Glu Gln Asp Val Asp Gly Ile Phe Phe Gln Asn Gln Ala Leu Ala
            20                  25                  30

Leu Gln Arg Lys Gly Ile Lys Thr Ala Val Leu Ala Pro Met Phe Arg
        35                  40                  45

Tyr Leu Arg Lys Glu Thr Ala Ser Ile Leu Thr Gly Pro Tyr Gly Phe
    50                  55                  60

Ala Gln Tyr Arg Gln Lys Gly Leu Asp Ile Tyr Ala Trp His Gly Met
65                  70                  75                  80

Tyr Phe Phe Pro Arg Phe Pro Leu Ile Asp Ile Asp Arg Ile Arg Trp
                85                  90                  95

Val Arg Ala Gly Leu Lys Ala Phe Glu Arg Tyr Ile Gly Glu Asn Gly
            100                 105                 110

Ile Pro Asp Ile Ile His Ala His Cys Met Asn Tyr Ala Gly Ile Leu
        115                 120                 125

Ala Phe Lys Ile Ser Gln Lys Tyr Gly Ile Pro Tyr Val Val Thr Glu
    130                 135                 140

His Ser Ser Thr Ile Thr Arg Gly Leu Val Arg Pro His Gln Trp Gln
145                 150                 155                 160

Pro Met Lys Asn Ala Ala Ala His Ala Ser Ala Leu Leu Ala Val Ser
                165                 170                 175

Cys Arg Phe Ala Gln Val Leu Gln His Lys Tyr Gly Thr Thr Trp Gln
            180                 185                 190

Tyr Leu Pro Asn Ile Leu Gly Asn Ile Phe Thr Arg Ala Phe Asn Pro
        195                 200                 205

Pro Gln Ile Asn Arg Pro Asp Lys Tyr Phe Thr Phe Cys Thr Ile Ser
    210                 215                 220

His Leu Arg Arg Leu Lys Gly His Asp Val Leu Leu Ser Ala Phe Ala
225                 230                 235                 240

Arg Ala Leu Ala Lys His Pro Asn Leu Arg Leu Asn Ile Gly Gly Ser
                245                 250                 255

Gly Gln Glu Glu Thr Ser Leu Lys Arg Gln Ala Arg Gln Leu Gly Ile
            260                 265                 270
```

```
Ala His Ala Val Thr Phe Leu Gly Ala Leu Gln Pro Glu Ala Val Leu
        275                 280                 285

Asp Leu Met Arg Asn Ser Asp Ala Phe Val Leu Ala Ser Arg Thr Glu
    290                 295                 300

Thr Phe Gly Val Val Tyr Ile Glu Ala Leu Ser Gln Gly Leu Pro Val
305                 310                 315                 320

Ile Ala Thr Arg Cys Gly Gly Ala Glu Ser Ile Val Ser Asp Gly Asn
                325                 330                 335

Gly Tyr Leu Val Pro Val Asp Asp Asp Asp Ala Leu Ala Asp Ala Leu
            340                 345                 350

Ile Lys Met Tyr Glu His His Ser Asp Phe Glu Pro Asp Arg Leu Arg
        355                 360                 365

Glu Asn Cys Leu Asn Glu Phe Gly Glu Asp Thr Val Ile Gly Lys Leu
    370                 375                 380

Ile Gly Ile Phe Arg Gln Ala Ile Ala Glu Tyr Gly Lys Lys Ile Pro
385                 390                 395                 400

Val Lys
```

<210> SEQ ID NO 37
<211> LENGTH: 894
<212> TYPE: DNA
<213> ORGANISM: Neisseria meningitidis

<400> SEQUENCE: 37

```
atgaagggtt ttaccattat tgaatttttg gttgcgggca tgctcagtat gattgtcctg     60

atggcggtcg gatcgagtta ctttacgtcc cggaaattaa atgatgcggc aaacgagcgt    120

cttgccgcgc aacaggattt gcggaatgcg gcaacattga ttgtccgcga tgcgagaatg    180

gcgggcggct tcggttgttt caatatgtcc gagcattctg caactgatgt tattcccgat    240

acgacgcaac aaaattctcc tttttcctta aaaaggaacg gtatagataa acttattccc    300

atagcggaat cttcaaatat cggatatccg gattttaccc agcgccttaa cgcattgatt    360

ttccaatacg gaatcgatga tgttaatgca agcgccgata ctaccgtcgt cagcagctgt    420

gccaaaatag caaaaccggg taagaaaata tctaccttgc aagaagcaaa gagtgcatta    480

cagattacta atgatgataa acaaaatgga aatatcaccc gtcaaaggca tgtggtcaat    540

gcctatgcgg tcggcaggat tgccggtgag gaaggtttgt tccgcttcca attgaatgat    600

aatgggcagt ggggtaatcc tcagttgttg gttaaaaaga ttaataaaat ggatatacgg    660

tatatttatg tttccaactg tcctgaagat gacgatgccg gcaaagagga aacattcaaa    720

tatacggata aattcaacag cgcccaaaat gctgttacgc ccgccggggt ggaggtttta    780

ttgagtagcg gtactgatac caagattgcc gcttcttcag acaatcatat ttatgcttac    840

cgtatcgatg cgacaatacg cgggggaaat gtatgcgcaa acagaacact ttga          894
```

<210> SEQ ID NO 38
<211> LENGTH: 297
<212> TYPE: PRT
<213> ORGANISM: Neisseria meningitidis

<400> SEQUENCE: 38

```
Met Lys Gly Phe Thr Ile Ile Glu Phe Leu Val Ala Gly Met Leu Ser
 1               5                  10                  15

Met Ile Val Leu Met Ala Val Gly Ser Ser Tyr Phe Thr Ser Arg Lys
            20                  25                  30

Leu Asn Asp Ala Ala Asn Glu Arg Leu Ala Ala Gln Gln Asp Leu Arg
        35                  40                  45
```

```
Asn Ala Ala Thr Leu Ile Val Arg Asp Ala Arg Met Ala Gly Gly Phe
    50                  55                  60

Gly Cys Phe Asn Met Ser Glu His Ser Ala Thr Asp Val Ile Pro Asp
65                  70                  75                  80

Thr Thr Gln Gln Asn Ser Pro Phe Ser Leu Lys Arg Asn Gly Ile Asp
                85                  90                  95

Lys Leu Ile Pro Ile Ala Glu Ser Ser Asn Ile Gly Tyr Pro Asp Phe
            100                 105                 110

Thr Gln Arg Leu Asn Ala Leu Ile Phe Gln Tyr Gly Ile Asp Asp Val
        115                 120                 125

Asn Ala Ser Ala Asp Thr Thr Val Val Ser Ser Cys Ala Lys Ile Ala
    130                 135                 140

Lys Pro Gly Lys Lys Ile Ser Thr Leu Gln Glu Ala Lys Ser Ala Leu
145                 150                 155                 160

Gln Ile Thr Asn Asp Asp Lys Gln Asn Gly Asn Ile Thr Arg Gln Arg
                165                 170                 175

His Val Val Asn Ala Tyr Ala Val Gly Arg Ile Ala Gly Glu Glu Gly
            180                 185                 190

Leu Phe Arg Phe Gln Leu Asn Asp Asn Gly Gln Trp Gly Asn Pro Gln
        195                 200                 205

Leu Leu Val Lys Lys Ile Asn Lys Met Asp Ile Arg Tyr Ile Tyr Val
    210                 215                 220

Ser Asn Cys Pro Glu Asp Asp Asp Ala Gly Lys Glu Glu Thr Phe Lys
225                 230                 235                 240

Tyr Thr Asp Lys Phe Asn Ser Ala Gln Asn Ala Val Thr Pro Ala Gly
                245                 250                 255

Val Glu Val Leu Leu Ser Ser Gly Thr Asp Thr Lys Ile Ala Ala Ser
            260                 265                 270

Ser Asp Asn His Ile Tyr Ala Tyr Arg Ile Asp Ala Thr Ile Arg Gly
        275                 280                 285

Gly Asn Val Cys Ala Asn Arg Thr Leu
    290                 295
```

<210> SEQ ID NO 39
<211> LENGTH: 681
<212> TYPE: DNA
<213> ORGANISM: Neisseria meningitidis

<400> SEQUENCE: 39

```
gtgcaggcgg atttagctta tgccgccgaa cgtattaccc acgattatcc gaaagcaacc     60

ggtgcagaca aagacaaaat aagcacagta agcgattatt tcagaaacat ccgtgcgcat    120

tccatccacc ctcgtgtgtc ggtcggctac gacttcggcg gctggagaat agcggcagat    180

tatgccagtt acagaaaatg gaacaacaat aaatattccg tcaacacaaa aaaggtgcaa    240

gaaaaccaag gcaccagaaa agacctgaag acggaaaatc aggaaaacgg cagcttccac    300

gccgcttctt ctctcggctt atccgccatt tacgatttca aactcaacga taaattcaaa    360

ccctatatcg gtgcgcgcgt cgcctacgga cacgtcagac acagcatcga ttcgaccaaa    420

aaaacaacag aggttgttac ctccacccat ggtggtgctg acacaaaacc tacgatttat    480

aatggggaaa gtacgcaaaa cgcctatcac gaaagccaca gcatccgccg cttgggtctt    540

ggtgtcgtcg ccggtgtcgg tttcgacatc acgcccaagc tgactttaga caccggatac    600

cgctaccaca actggggacg cttggaaaac acccgcttca aaacccacga agtctcattg    660

ggcatgcgct accgcttctg a                                               681
```

<210> SEQ ID NO 40
<211> LENGTH: 226
<212> TYPE: PRT
<213> ORGANISM: Neisseria meningitidis

<400> SEQUENCE: 40

```
Met Gln Ala Asp Leu Ala Tyr Ala Ala Glu Arg Ile Thr His Asp Tyr
 1               5                  10                  15

Pro Lys Ala Thr Gly Ala Asp Lys Asp Lys Ile Ser Thr Val Ser Asp
            20                  25                  30

Tyr Phe Arg Asn Ile Arg Ala His Ser Ile His Pro Arg Val Ser Val
        35                  40                  45

Gly Tyr Asp Phe Gly Gly Trp Arg Ile Ala Ala Asp Tyr Ala Ser Tyr
    50                  55                  60

Arg Lys Trp Asn Asn Asn Lys Tyr Ser Val Asn Thr Lys Lys Val Gln
65                  70                  75                  80

Glu Asn Gln Gly Thr Arg Lys Asp Leu Lys Thr Glu Asn Gln Glu Asn
                85                  90                  95

Gly Ser Phe His Ala Ala Ser Ser Leu Gly Leu Ser Ala Ile Tyr Asp
            100                 105                 110

Phe Lys Leu Asn Asp Lys Phe Lys Pro Tyr Ile Gly Ala Arg Val Ala
        115                 120                 125

Tyr Gly His Val Arg His Ser Ile Asp Ser Thr Lys Lys Thr Thr Glu
    130                 135                 140

Val Val Thr Ser Thr His Gly Gly Ala Asp Thr Lys Pro Thr Ile Tyr
145                 150                 155                 160

Asn Gly Glu Ser Thr Gln Asn Ala Tyr His Glu Ser His Ser Ile Arg
                165                 170                 175

Arg Leu Gly Leu Gly Val Val Ala Gly Val Gly Phe Asp Ile Thr Pro
            180                 185                 190

Lys Leu Thr Leu Asp Thr Gly Tyr Arg Tyr His Asn Trp Gly Arg Leu
        195                 200                 205

Glu Asn Thr Arg Phe Lys Thr His Glu Val Ser Leu Gly Met Arg Tyr
    210                 215                 220

Arg Phe
225
```

<210> SEQ ID NO 41
<211> LENGTH: 1767
<212> TYPE: DNA
<213> ORGANISM: Neisseria meningitidis

<400> SEQUENCE: 41

```
atgaacaaaa tataccgcat catttggaat agtgccctca atgcctgggt cgccgtatcc      60

gagctcacac gcaaccacac caaacgcgcc tccgcaaccg tggcgaccgc cgtattggcg     120

acactgttgt ttgcaacggt tcaggcgagt actaccgatg aagatgaaga agaagagtta     180

gaacccgtag tacgctctgc tctggtgttg caattcatga tcgataaaga aggcaatgga     240

gaaaacgaat ctacaggaaa tataggttgg agtatatatt acgacaatca caacactcta     300

cacggcgcaa ccgttaccct caaagccggc gacaacctga aaatcaaaca aaacggcaca     360

aacttcacct actcgctgaa aaaagccctc acaggtctga ccagtgttgg aactgaagaa     420

ttatcgtttg gcgcaaacgg caagaaagtc aacatcacaa gcgacaccaa aggcttgaat     480

tttgcgaaag aaacggctgg gacgaacggc gacaccacgg ttcatctgaa cggtattggt     540
```

```
tctactttaa ccgatacgct tgcgggttct tctgcttctc acgttgatgc gggtaaccaa    600

agtacacatt acactcgtgc agcaagtatt aaggatgtgt tgaatgcggg ttggaatatt    660

aagggtgtta aaactggctc aacaactggt caatcagaaa atgtcgattt cgtccgcact    720

tacgacacag tcgagttctt gagcgcagat acgaaaacaa cgactgttaa tgtggaaagc    780

aaagacaacg gcaagagaac cgaagttaaa atcggtgcga agacttctgt tatcaaagaa    840

aaagacggta agttggttac tggtaaaggc aaaggcgaga atggttcttc tacagacgaa    900

ggcgaaggct tagtgactgc aaaagaagtg attgatgcag taaacaaggc tggttggaga    960

atgaaaacaa caaccgctaa tggtcaaaca ggtcaagctg acaagtttga aaccgttaca   1020

tcaggcacaa atgtaacctt tgctagtggt aaaggtacaa ctgcgactgt aagtaaagat   1080

gctcaaggca acatcactgt taagtatgat gtaaatgtcg gcgatgccct aaacgtcaat   1140

cagctgcaaa acagcggttg gaatttggat tccaaagcgg ttgcaggttc ttcgggcaaa   1200

gtcatcagcg gcaatgtttc gccgagcaag ggaaagatgg atgaaaccgt caacattaat   1260

gccggcaaca acatcgagat tacccgcaac ggtaaaaata tcgacatcgc cacttcgatg   1320

accccgcagt tttccagcgt ttcgctcggc gcgggggcgg atgcgcccac tttgagcgtg   1380

gatggggacg cattgaatgt cggcagcaag aaggacaaca aacccgtccg cattaccaat   1440

gtcgccccgg gcgttaaaga gggggatgtt acaaacgtcg cacaacttaa aggcgtggcg   1500

caaaacttga acaaccgcat cgacaatgtg gacggcaacg cgcgtgcggg catcgcccaa   1560

gcgattgcaa ccgcaggtct ggttcaggcg tatttgcccg gcaagagtat gatggcgatc   1620

ggcggcggca cttatcgcgg cgaagccggt tacgccatcg gctactccag tatttccgac   1680

ggcggaaatt ggattatcaa aggcacggct tccggcaatt cgcgcggcca tttcggtgct   1740

tccgcatctg tcggttatca gtggtaa                                       1767
```

<210> SEQ ID NO 42
<211> LENGTH: 588
<212> TYPE: PRT
<213> ORGANISM: Neisseria meningitidis

<400> SEQUENCE: 42

```
Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
        35                  40                  45

Ala Ser Thr Thr Asp Glu Asp Glu Glu Glu Glu Leu Glu Pro Val Val
    50                  55                  60

Arg Ser Ala Leu Val Leu Gln Phe Met Ile Asp Lys Glu Gly Asn Gly
65                  70                  75                  80

Glu Asn Glu Ser Thr Gly Asn Ile Gly Trp Ser Ile Tyr Tyr Asp Asn
                85                  90                  95

His Asn Thr Leu His Gly Ala Thr Val Thr Leu Lys Ala Gly Asp Asn
            100                 105                 110

Leu Lys Ile Lys Gln Asn Gly Thr Asn Phe Thr Tyr Ser Leu Lys Lys
        115                 120                 125

Ala Leu Thr Gly Leu Thr Ser Val Gly Thr Glu Glu Leu Ser Phe Gly
    130                 135                 140

Ala Asn Gly Lys Lys Val Asn Ile Thr Ser Asp Thr Lys Gly Leu Asn
145                 150                 155                 160
```

-continued

```
Phe Ala Lys Glu Thr Ala Gly Thr Asn Gly Asp Thr Thr Val His Leu
                165                 170                 175

Asn Gly Ile Gly Ser Thr Leu Thr Asp Thr Leu Ala Gly Ser Ser Ala
            180                 185                 190

Ser His Val Asp Ala Gly Asn Gln Ser Thr His Tyr Thr Arg Ala Ala
        195                 200                 205

Ser Ile Lys Asp Val Leu Asn Ala Gly Trp Asn Ile Lys Gly Val Lys
    210                 215                 220

Thr Gly Ser Thr Thr Gly Gln Ser Glu Asn Val Asp Phe Val Arg Thr
225                 230                 235                 240

Tyr Asp Thr Val Glu Phe Leu Ser Ala Asp Thr Lys Thr Thr Thr Val
                245                 250                 255

Asn Val Glu Ser Lys Asp Asn Gly Lys Arg Thr Glu Val Lys Ile Gly
            260                 265                 270

Ala Lys Thr Ser Val Ile Lys Glu Lys Asp Gly Lys Leu Val Thr Gly
        275                 280                 285

Lys Gly Lys Gly Glu Asn Gly Ser Ser Thr Asp Glu Gly Glu Gly Leu
    290                 295                 300

Val Thr Ala Lys Glu Val Ile Asp Ala Val Asn Lys Ala Gly Trp Arg
305                 310                 315                 320

Met Lys Thr Thr Thr Ala Asn Gly Gln Thr Gly Gln Ala Asp Lys Phe
                325                 330                 335

Glu Thr Val Thr Ser Gly Thr Asn Val Thr Phe Ala Ser Gly Lys Gly
            340                 345                 350

Thr Thr Ala Thr Val Ser Lys Asp Ala Gln Gly Asn Ile Thr Val Lys
        355                 360                 365

Tyr Asp Val Asn Val Gly Asp Ala Leu Asn Val Asn Gln Leu Gln Asn
    370                 375                 380

Ser Gly Trp Asn Leu Asp Ser Lys Ala Val Ala Gly Ser Ser Gly Lys
385                 390                 395                 400

Val Ile Ser Gly Asn Val Ser Pro Ser Lys Gly Lys Met Asp Glu Thr
                405                 410                 415

Val Asn Ile Asn Ala Gly Asn Asn Ile Glu Ile Thr Arg Asn Gly Lys
            420                 425                 430

Asn Ile Asp Ile Ala Thr Ser Met Thr Pro Gln Phe Ser Ser Val Ser
        435                 440                 445

Leu Gly Ala Gly Ala Asp Ala Pro Thr Leu Ser Val Asp Gly Asp Ala
    450                 455                 460

Leu Asn Val Gly Ser Lys Lys Asp Asn Lys Pro Val Arg Ile Thr Asn
465                 470                 475                 480

Val Ala Pro Gly Val Lys Glu Gly Asp Val Thr Asn Val Ala Gln Leu
                485                 490                 495

Lys Gly Val Ala Gln Asn Leu Asn Asn Arg Ile Asp Asn Val Asp Gly
            500                 505                 510

Asn Ala Arg Ala Gly Ile Ala Gln Ala Ile Ala Thr Ala Gly Leu Val
        515                 520                 525

Gln Ala Tyr Leu Pro Gly Lys Ser Met Met Ala Ile Gly Gly Gly Thr
    530                 535                 540

Tyr Arg Gly Glu Ala Gly Tyr Ala Ile Gly Tyr Ser Ser Ile Ser Asp
545                 550                 555                 560

Gly Gly Asn Trp Ile Ile Lys Gly Thr Ala Ser Gly Asn Ser Arg Gly
                565                 570                 575

His Phe Gly Ala Ser Ala Ser Val Gly Tyr Gln Trp
            580                 585
```

<210> SEQ ID NO 43
<211> LENGTH: 606
<212> TYPE: DNA
<213> ORGANISM: Neisseria meningitidis

<400> SEQUENCE: 43
atgattgaat ccatagaaaa accacaggaa tctatcagaa aaaacagaaa cccccaccgc 60
gtcattcccg cgaaagcggg aatccagaaa cgcaacgcaa caggaattta tcggaaaaaa 120
cagaaacctc accgccgtca ttcccgcaaa agctggaatc caaaaacgca acgcggcagg 180
actttatcgg aaaaaacaga aaccccaccg accgtcattc ccgcaaaagc gggaatccaa 240
aaacgcaacg caacaggaat ttatcggaaa aaacagaaac cccaccgacc gtcattcccg 300
caaaagcggg aatccagcaa ccgaaaaacc acaggaatct atcagcaaaa acagaaaccc 360
ccaccgaccg tcattcccgc gcaggcggga atccagaaac acaacgcggc aggactttat 420
cggaaaaaac agaaactcca ccgaccgtca ttcccgcaaa agctggaatc caaaaacgca 480
acgcaacagg aatttatcgg aaaaaacaga aaccccaccg ccgtcattcc cgcaaaagcg 540
ggaatccaga cccgtcggca cggaatctta ccggataaaa cagtttcctt agattccacg 600
tcctag 606

<210> SEQ ID NO 44
<211> LENGTH: 201
<212> TYPE: PRT
<213> ORGANISM: Neisseria meningitidis

<400> SEQUENCE: 44

Met Ile Glu Ser Ile Glu Lys Pro Gln Glu Ser Ile Arg Lys Asn Arg
1               5                   10                  15

Asn Pro His Arg Val Ile Pro Ala Lys Ala Gly Ile Gln Lys Arg Asn
            20                  25                  30

Ala Thr Gly Ile Tyr Arg Lys Lys Gln Lys Pro His Arg Arg His Ser
        35                  40                  45

Arg Lys Ser Trp Asn Pro Lys Thr Gln Arg Gly Arg Thr Leu Ser Glu
    50                  55                  60

Lys Thr Glu Thr Pro Pro Thr Val Ile Pro Ala Lys Ala Gly Ile Gln
65                  70                  75                  80

Lys Arg Asn Ala Thr Gly Ile Tyr Arg Lys Lys Gln Lys Pro His Arg
                85                  90                  95

Pro Ser Phe Pro Gln Lys Arg Glu Ser Ser Asn Arg Lys Thr Thr Gly
            100                 105                 110

Ile Tyr Gln Gln Lys Gln Lys Pro Pro Pro Thr Val Ile Pro Ala Gln
        115                 120                 125

Ala Gly Ile Gln Lys His Asn Ala Ala Gly Leu Tyr Arg Lys Lys Gln
    130                 135                 140

Lys Leu His Arg Pro Ser Phe Pro Gln Lys Leu Glu Ser Lys Asn Ala
145                 150                 155                 160

Thr Gln Gln Glu Phe Ile Gly Lys Asn Arg Asn Pro Thr Ala Val Ile
                165                 170                 175

Pro Ala Lys Ala Gly Ile Gln Thr Arg Arg His Gly Ile Leu Pro Asp
            180                 185                 190

Lys Thr Val Ser Leu Asp Ser Thr Ser
        195                 200

<210> SEQ ID NO 45

<211> LENGTH: 1014
<212> TYPE: DNA
<213> ORGANISM: Neisseria meningitidis

<400> SEQUENCE: 45

```
atgattttct ccatcatcgt ccctatttac aatgtggaaa aatacctccg ctgctgcgtg      60

gattccgtgc ttgccgaaaa ttttgccgat tatgaaatga ttttggtcga tgacggttcg     120

ccggatggct gcgggaagat ttgcgacgaa tatgcaggca aatatccgca tataaaagtg     180

attcatcaag aaaacggcgg gctgtcggat gcccgcaacg ccggtatccg agcggcaaaa     240

ggcgattacc tgatcttttt ggacagcgac gactattggg ccgataccaa ccgttcaaaa     300

aacgcggggg gggggattct ctttgattta caacaacttg cagacaaaaa ggttgatttg     360

atcctgcatc cctcgtccct caattaccac gtcatcccca aggggcgga cttttcggat      420

aatgattttg tccgccattt tgaaacgttg gtggaggggc ggtactatat cgccaacgcg     480

tggacaaaaa tcgtcaggcg ggaaataatc atcaaaaaca atctgttttt cccaaaagga     540

tacattcacg aggatttccc gtacagtttg caattggcgc gttttatcaa gacttttgcc     600

ttttacgata acccttttta ccagtaccgc gttctcggcg gctctatcag ccacaacatc     660

aaatacaaaa atttcagcga tgtgctgacg catctcgacc ggggtgtgga ttttttagtc     720

gaaaacaaaa attcccccat ctacggcggt ttgcaaaaat ttgtcttcga caatatcggc     780

tatctgaggt ctatattggt aaggctttat ttttccaaaa acattatcgt catctaccgg     840

aaatattttt catttaaaga aaaatgcaga aagatattcg gcgcgaaggc aatccgtccg     900

gtttttatcg ggaagaccgc attcatcata ggattgccga tattgcgcct gctcgtaccg     960

cctatgctgt acccggcaat caaggccgtt tatcaaaaat ttttttcgga ataa          1014
```

<210> SEQ ID NO 46
<211> LENGTH: 337
<212> TYPE: PRT
<213> ORGANISM: Neisseria meningitidis

<400> SEQUENCE: 46

```
Met Ile Phe Ser Ile Ile Val Pro Ile Tyr Asn Val Glu Lys Tyr Leu
 1               5                  10                  15

Arg Cys Cys Val Asp Ser Val Leu Ala Glu Asn Phe Ala Asp Tyr Glu
            20                  25                  30

Met Ile Leu Val Asp Asp Gly Ser Pro Asp Gly Cys Gly Lys Ile Cys
        35                  40                  45

Asp Glu Tyr Ala Gly Lys Tyr Pro His Ile Lys Val Ile His Gln Glu
    50                  55                  60

Asn Gly Gly Leu Ser Asp Ala Arg Asn Ala Gly Ile Arg Ala Ala Lys
65                  70                  75                  80

Gly Asp Tyr Leu Ile Phe Leu Asp Ser Asp Asp Tyr Trp Ala Asp Thr
                85                  90                  95

Asn Arg Ser Lys Asn Ala Gly Gly Gly Ile Leu Phe Asp Leu Gln Gln
            100                 105                 110

Leu Ala Asp Lys Lys Val Asp Leu Ile Leu His Pro Ser Ser Leu Asn
        115                 120                 125

Tyr His Val Ile Pro Lys Gly Ala Asp Phe Ser Asp Asn Asp Phe Val
    130                 135                 140

Arg His Phe Glu Thr Leu Val Glu Gly Arg Tyr Tyr Ile Ala Asn Ala
145                 150                 155                 160

Trp Thr Lys Ile Val Arg Arg Glu Ile Ile Ile Lys Asn Asn Leu Phe
                165                 170                 175
```

Phe Pro Lys Gly Tyr Ile His Glu Asp Phe Pro Tyr Ser Leu Gln Leu
180 185 190

Ala Arg Phe Ile Lys Thr Phe Ala Phe Tyr Asp Asn Pro Phe Tyr Gln
195 200 205

Tyr Arg Val Leu Gly Gly Ser Ile Ser His Asn Ile Lys Tyr Lys Asn
210 215 220

Phe Ser Asp Val Leu Thr His Leu Asp Arg Gly Val Asp Phe Leu Val
225 230 235 240

Glu Asn Lys Asn Ser Pro Ile Tyr Gly Gly Leu Gln Lys Phe Val Phe
245 250 255

Asp Asn Ile Gly Tyr Leu Arg Ser Ile Leu Val Arg Leu Tyr Phe Ser
260 265 270

Lys Asn Ile Ile Val Ile Tyr Arg Lys Tyr Phe Ser Phe Lys Glu Lys
275 280 285

Cys Arg Lys Ile Phe Gly Ala Lys Ala Ile Arg Pro Val Phe Ile Gly
290 295 300

Lys Thr Ala Phe Ile Ile Gly Leu Pro Ile Leu Arg Leu Leu Val Pro
305 310 315 320

Pro Met Leu Tyr Pro Ala Ile Lys Ala Val Tyr Gln Lys Phe Phe Ser
325 330 335

Glu

<210> SEQ ID NO 47
<211> LENGTH: 1590
<212> TYPE: DNA
<213> ORGANISM: Neisseria meningitidis
<220> FEATURE:
<221> NAME/KEY: misc_feature
<222> LOCATION: 1571, 1572, 1573, 1574, 1575
<223> OTHER INFORMATION: n = A,T,C or G

<400> SEQUENCE: 47
atgacatctg caaattttaa tattaacggt tttggagatg tgaaattaac accctattca 60
ccactcttgg gatataaagc ttgggattca tttattggtt ctattcaatc cttatctgat 120
ttaatctata atgtggataa caatagaaat aaaatggaaa ttactgttaa taatgctatc 180
caagctgcag atagcttttt aagcagtatt ggaagagata acaaaataac aaatactgct 240
tctttacttg catccctcga taacattttt ttaaatttaa gaaatgtatc tcgagatata 300
cgagaaacag gaaaatttaa acctaatgat attcaacaag caattggtga tatattcatt 360
gctgctggtg atggattaca atatataaaa caacaaacag aggcgatggc tcaaagcaaa 420
ttcttaccaa ctaaattaaa aactggttta aatgatgtcc ttaattctag aatgctaaaa 480
tcctctactg ttttacagca tgaattgaat tatttgggat ttaaaataaa ggattatgga 540
aacgagaggc ttggcgaatc tataatgaat atagatgatt ttacaccaag taagatagca 600
aacttttttg cggatcctga tacatacagc aatgtattag aagaagtatc taggtttata 660
tattccttag ttcctgatga tgcaaaccct tggaaagggg gcgaagatta tattggacga 720
gggataagtg aatggggaga gttactggaa aaatggtata aacaagattt tctcccttat 780
cttgaaaaag aatgggacca atttccgaaa tttgaagatt ggctgcctga attccctgaa 840
tgggcaagag agtggttgaa attagatccc aaacgttcag gcaaatatca tgtctacgac 900
cccctcgccc tagatctaga cggcgacggt atagaaaccg ttgccaccaa aggctttgca 960
ggcagcttat ttgatcacac caacaacggt atccgcaccg ccaccggttg ggtttctgcc 1020
gatgacggtt tactcgtccg cgatttgaac ggcaacggca tcatcgacaa cggtgcggaa 1080

-continued

```
ctcttcggcg acaacaccaa actggcagac ggttcttttg ccaaacacgg ctatgcagct   1140

ttggccgaat tggattcaaa cggcgacaac atcatcaacg cggcagacgc cgcattccaa   1200

accctgcgtg tatggcagga tctcaatcag gacggcattt cccaaaccaa cgaactccgc   1260

acccttgaag aattgggtat tcaatctttg gatctcgcct ataaagatgt aaataaaaat   1320

ctcggtaacg gtaacacttt ggctcagcaa ggtagctaca ccaaaacaaa cggtacaacc   1380

gcaaaaatgg gggatttact tttagcagcc gacaatctgc acagccgctt caaagacaaa   1440

gtggaactca ctgccaaaca ggcaaaagcc gccaatcttg cgggcattgg tcgtctgcgc   1500

gatttgcgcg aagctgccgc attgtccggc gatttggcca atatgctgaa agcttattct   1560

gccgccgaaa nnnnncacac acttaattaa                                    1590
```

<210> SEQ ID NO 48
<211> LENGTH: 529
<212> TYPE: PRT
<213> ORGANISM: Neisseria meningitidis
<220> FEATURE:
<221> NAME/KEY: VARIANT
<222> LOCATION: 524, 525
<223> OTHER INFORMATION: Xaa = Any Amino Acid

<400> SEQUENCE: 48

```
Met Thr Ser Ala Asn Phe Asn Ile Asn Gly Phe Gly Asp Val Lys Leu
 1               5                  10                  15

Thr Pro Tyr Ser Pro Leu Leu Gly Tyr Lys Ala Trp Asp Ser Phe Ile
            20                  25                  30

Gly Ser Ile Gln Ser Leu Ser Asp Leu Ile Tyr Asn Val Asp Asn Asn
        35                  40                  45

Arg Asn Lys Met Glu Ile Thr Val Asn Asn Ala Ile Gln Ala Ala Asp
    50                  55                  60

Ser Phe Leu Ser Ser Ile Gly Arg Asp Asn Lys Ile Thr Asn Thr Ala
65                  70                  75                  80

Ser Leu Leu Ala Ser Leu Asp Asn Ile Phe Leu Asn Leu Arg Asn Val
                85                  90                  95

Ser Arg Asp Ile Arg Glu Thr Gly Lys Phe Lys Pro Asn Asp Ile Gln
            100                 105                 110

Gln Ala Ile Gly Asp Ile Phe Ile Ala Ala Gly Asp Gly Leu Gln Tyr
        115                 120                 125

Ile Lys Gln Gln Thr Glu Ala Met Ala Gln Ser Lys Phe Leu Pro Thr
    130                 135                 140

Lys Leu Lys Thr Gly Leu Asn Asp Val Leu Asn Ser Arg Met Leu Lys
145                 150                 155                 160

Ser Ser Thr Val Leu Gln His Glu Leu Asn Tyr Leu Gly Phe Lys Ile
                165                 170                 175

Lys Asp Tyr Gly Asn Glu Arg Leu Gly Glu Ser Ile Met Asn Ile Asp
            180                 185                 190

Asp Phe Thr Pro Ser Lys Ile Ala Asn Phe Phe Ala Asp Pro Asp Thr
        195                 200                 205

Tyr Ser Asn Val Leu Glu Glu Val Ser Arg Phe Ile Tyr Ser Leu Val
    210                 215                 220

Pro Asp Asp Ala Asn Pro Trp Lys Gly Gly Glu Asp Tyr Ile Gly Arg
225                 230                 235                 240

Gly Ile Ser Glu Trp Gly Glu Leu Leu Glu Lys Trp Tyr Lys Gln Asp
                245                 250                 255

Phe Leu Pro Tyr Leu Glu Lys Glu Trp Asp Gln Phe Pro Lys Phe Glu
```

```
            260                 265                 270

Asp Trp Leu Pro Glu Phe Pro Glu Trp Ala Arg Glu Trp Leu Lys Leu
        275                 280                 285

Asp Pro Lys Arg Ser Gly Lys Tyr His Val Tyr Asp Pro Leu Ala Leu
    290                 295                 300

Asp Leu Asp Gly Asp Gly Ile Glu Thr Val Ala Thr Lys Gly Phe Ala
305                 310                 315                 320

Gly Ser Leu Phe Asp His Thr Asn Asn Gly Ile Arg Thr Ala Thr Gly
                325                 330                 335

Trp Val Ser Ala Asp Asp Gly Leu Leu Val Arg Asp Leu Asn Gly Asn
            340                 345                 350

Gly Ile Ile Asp Asn Gly Ala Glu Leu Phe Gly Asp Asn Thr Lys Leu
        355                 360                 365

Ala Asp Gly Ser Phe Ala Lys His Gly Tyr Ala Ala Leu Ala Glu Leu
    370                 375                 380

Asp Ser Asn Gly Asp Asn Ile Ile Asn Ala Ala Asp Ala Ala Phe Gln
385                 390                 395                 400

Thr Leu Arg Val Trp Gln Asp Leu Asn Gln Asp Gly Ile Ser Gln Thr
                405                 410                 415

Asn Glu Leu Arg Thr Leu Glu Glu Leu Gly Ile Gln Ser Leu Asp Leu
            420                 425                 430

Ala Tyr Lys Asp Val Asn Lys Asn Leu Gly Asn Gly Asn Thr Leu Ala
        435                 440                 445

Gln Gln Gly Ser Tyr Thr Lys Thr Asn Gly Thr Thr Ala Lys Met Gly
    450                 455                 460

Asp Leu Leu Leu Ala Ala Asp Asn Leu His Ser Arg Phe Lys Asp Lys
465                 470                 475                 480

Val Glu Leu Thr Ala Lys Gln Ala Lys Ala Ala Asn Leu Ala Gly Ile
                485                 490                 495

Gly Arg Leu Arg Asp Leu Arg Glu Ala Ala Ala Leu Ser Gly Asp Leu
            500                 505                 510

Ala Asn Met Leu Lys Ala Tyr Ser Ala Ala Glu Xaa Xaa His Thr Leu
        515                 520                 525

Asn


<210> SEQ ID NO 49
<211> LENGTH: 2031
<212> TYPE: DNA
<213> ORGANISM: Neisseria meningitidis

<400> SEQUENCE: 49

ttgaggcgga atatcgcaac ttctgataag gatggcaatg attttccaaa tagcaaacaa      60

gcagaagaaa agctgtcgtt taaagaggaa gatatcctgt ttttatacgg ttccaaaaaa     120

gatcaacgtc agcagcttga agataaaatt catcaacgca atcctaatgt aaaaattagg     180

acatcagaaa atgaaaataa aaaatatggt tataactttg tagatgcagg ttatgtatat     240

gtaaagggag aagatgaaat tgagaggact tcaaattaca agtattttac tcaccggttt     300

ggttatgacg gttttgtata ttattccgga gaacgtcctt cccaatcttt accgagttcg     360

ggaacggtgc aatattccgg caactggcaa tatatgaccg atgccatacg tcatcggaca     420

ggaaaagcag gagatcctag cgaagatttg ggttatctcg tttattacgg tcaaaatgtc     480

ggagcaactt cttatgctgc gactgccgac gaccgggagg gggagggaaa acatcctgcc     540

gaatatacgg ttgatttcga caaaaaaacc ctgaatggca agctgattaa aaatcagtat     600
```

-continued

```
gtgcaaaaga aggacgatga aaagaaaccg ctgaccattt acaacattac tgcaaaattg    660

gacggcaacc gctttaccgg cagtgccaag gtcaatcctg atttagcgaa aaaccatgcc    720

aagaaggagc atttgttttt ccataccgat gccgatcagc ggcttgaggg cggtttttttc   780

ggcgataagg gggaagagct tgccggacgg tttatcagca acgacaacag cgtattcggc    840

gtattcgcag gcaaacaaaa aacagaggca gcaaacgcag cagatacaaa acttgccttg    900

ccgtctagaa aacacaccaa aatcttggat tctctaaaaa tttccgttga cgaggcaagt    960

gataacaatg cccgccagtt tgccatttcc tctatgcccg atcttggtca tcccgacaaa   1020

cttcttgtcg aagggcgtga aattcctttg gtaaaccaag aacaaaccat cgatcttgcc   1080

gacggcagga aatgaccgt ccgtgcttgt tgcgattttc tgacctatgt gaaactcgga    1140

cggataaaaa ccgaccgccc ggcaagtaaa tcaaaggcgg aagataaagg ggaggatgaa   1200

gagggtgcag gcgttgataa cggcgaagaa gacgaaatca gcgatgaaga cgaagtttcc   1260

gaagatgaaa gcgaagaaga cgaagaaatc gtcgaagaag aaaccgaaga agacgaaacc   1320

gaagaagacg aagaggggga agctgaagag gaagaagccg aagaagcaga agaaactgaa   1380

gaaaaatcgc cggcagaagg caacggcgat tcaggcagca tcctgcctgc cccggaagcc   1440

cctaaaggca gggacatcga cctttttcctg aaaggtatcc gcacggcgga agccgacatt  1500

ccgcaaaccg gaaaagcaca ctataccggc acttgggaag cgcgtatcag caaacccatt   1560

caatgggata ataaggcgga taaagcggca aaagcagagt ttaatgttga tttcggcgag   1620

aaatcgattt ccggaacgct gacggagaaa aatggtgtag aagctgcttt ctatattgaa   1680

aaaggtgtga ttgagggcaa cggtttccac gcgacagcgc gcactcggga gaacggcatc   1740

gacctttccg ggcagggttc gaccagatcg cagagcttca aagccgacaa tcttcttgta   1800

acgggcggct tttacggccc gaaggcggag gaattgggcg gtactatttt caataatgat   1860

gggaaatctc ttagtataac tgaaaatatt gaaaatgaag ttgaagttga agctgaagct   1920

gaagttgaag ttgaagctga tgttggcaaa cagttagaac ctgatgaagt taaacaccaa   1980

ttcggcgtgg tatttggtgc gaagaaagat aataaagagg tggaaaaatg a            2031
```

```
<210> SEQ ID NO 50
<211> LENGTH: 676
<212> TYPE: PRT
<213> ORGANISM: Neisseria meningitidis

<400> SEQUENCE: 50

Met Arg Arg Asn Ile Ala Thr Ser Asp Lys Asp Gly Asn Asp Phe Pro
1               5                   10                  15

Asn Ser Lys Gln Ala Glu Glu Lys Leu Ser Phe Lys Glu Glu Asp Ile
            20                  25                  30

Leu Phe Leu Tyr Gly Ser Lys Lys Asp Gln Arg Gln Gln Leu Glu Asp
        35                  40                  45

Lys Ile His Gln Arg Asn Pro Asn Val Lys Ile Arg Thr Ser Glu Asn
    50                  55                  60

Glu Asn Lys Lys Tyr Gly Tyr Asn Phe Val Asp Ala Gly Tyr Val Tyr
65                  70                  75                  80

Val Lys Gly Glu Asp Glu Ile Glu Arg Thr Ser Asn Tyr Lys Tyr Phe
                85                  90                  95

Thr His Arg Phe Gly Tyr Asp Gly Phe Val Tyr Tyr Ser Gly Glu Arg
            100                 105                 110

Pro Ser Gln Ser Leu Pro Ser Ser Gly Thr Val Gln Tyr Ser Gly Asn
        115                 120                 125
```

-continued

```
Trp Gln Tyr Met Thr Asp Ala Ile Arg His Arg Thr Gly Lys Ala Gly
    130                 135                 140

Asp Pro Ser Glu Asp Leu Gly Tyr Leu Val Tyr Tyr Gly Gln Asn Val
145                 150                 155                 160

Gly Ala Thr Ser Tyr Ala Ala Thr Ala Asp Asp Arg Glu Gly Glu Gly
                165                 170                 175

Lys His Pro Ala Glu Tyr Thr Val Asp Phe Asp Lys Lys Thr Leu Asn
            180                 185                 190

Gly Lys Leu Ile Lys Asn Gln Tyr Val Gln Lys Lys Asp Asp Glu Lys
        195                 200                 205

Lys Pro Leu Thr Ile Tyr Asn Ile Thr Ala Lys Leu Asp Gly Asn Arg
    210                 215                 220

Phe Thr Gly Ser Ala Lys Val Asn Pro Asp Leu Ala Lys Asn His Ala
225                 230                 235                 240

Lys Lys Glu His Leu Phe Phe His Thr Asp Ala Asp Gln Arg Leu Glu
                245                 250                 255

Gly Gly Phe Phe Gly Asp Lys Gly Glu Glu Leu Ala Gly Arg Phe Ile
            260                 265                 270

Ser Asn Asp Asn Ser Val Phe Gly Val Phe Ala Gly Lys Gln Lys Thr
        275                 280                 285

Glu Ala Ala Asn Ala Ala Asp Thr Lys Leu Ala Leu Pro Ser Arg Lys
    290                 295                 300

His Thr Lys Ile Leu Asp Ser Leu Lys Ile Ser Val Asp Glu Ala Ser
305                 310                 315                 320

Asp Asn Asn Ala Arg Gln Phe Ala Ile Ser Ser Met Pro Asp Leu Gly
                325                 330                 335

His Pro Asp Lys Leu Leu Val Glu Gly Arg Glu Ile Pro Leu Val Asn
            340                 345                 350

Gln Glu Gln Thr Ile Asp Leu Ala Asp Gly Arg Lys Met Thr Val Arg
        355                 360                 365

Ala Cys Cys Asp Phe Leu Thr Tyr Val Lys Leu Gly Arg Ile Lys Thr
    370                 375                 380

Asp Arg Pro Ala Ser Lys Ser Lys Ala Glu Asp Lys Gly Glu Asp Glu
385                 390                 395                 400

Glu Gly Ala Gly Val Asp Asn Gly Glu Glu Asp Glu Ile Ser Asp Glu
                405                 410                 415

Asp Glu Val Ser Glu Asp Glu Ser Glu Glu Asp Glu Glu Ile Val Glu
            420                 425                 430

Glu Glu Thr Glu Glu Asp Glu Thr Glu Glu Asp Glu Glu Gly Glu Ala
        435                 440                 445

Glu Glu Glu Glu Ala Glu Glu Ala Glu Glu Thr Glu Glu Lys Ser Pro
    450                 455                 460

Ala Glu Gly Asn Gly Asp Ser Gly Ser Ile Leu Pro Ala Pro Glu Ala
465                 470                 475                 480

Pro Lys Gly Arg Asp Ile Asp Leu Phe Leu Lys Gly Ile Arg Thr Ala
                485                 490                 495

Glu Ala Asp Ile Pro Gln Thr Gly Lys Ala His Tyr Thr Gly Thr Trp
            500                 505                 510

Glu Ala Arg Ile Ser Lys Pro Ile Gln Trp Asp Asn Lys Ala Asp Lys
        515                 520                 525

Ala Ala Lys Ala Glu Phe Asn Val Asp Phe Gly Glu Lys Ser Ile Ser
    530                 535                 540

Gly Thr Leu Thr Glu Lys Asn Gly Val Glu Ala Ala Phe Tyr Ile Glu
545                 550                 555                 560
```

```
Lys Gly Val Ile Glu Gly Asn Gly Phe His Ala Thr Ala Arg Thr Arg
                565                 570                 575

Glu Asn Gly Ile Asp Leu Ser Gly Gln Gly Ser Thr Arg Ser Gln Ser
            580                 585                 590

Phe Lys Ala Asp Asn Leu Leu Val Thr Gly Gly Phe Tyr Gly Pro Lys
        595                 600                 605

Ala Glu Glu Leu Gly Gly Thr Ile Phe Asn Asn Asp Gly Lys Ser Leu
    610                 615                 620

Ser Ile Thr Glu Asn Ile Glu Asn Glu Val Glu Val Glu Ala Glu Ala
625                 630                 635                 640

Glu Val Glu Val Glu Ala Asp Val Gly Lys Gln Leu Glu Pro Asp Glu
                645                 650                 655

Val Lys His Gln Phe Gly Val Val Phe Gly Ala Lys Lys Asp Asn Lys
            660                 665                 670

Glu Val Glu Lys
        675
```

<210> SEQ ID NO 51
<211> LENGTH: 612
<212> TYPE: DNA
<213> ORGANISM: Neisseria meningitidis
<220> FEATURE:
<221> NAME/KEY: misc_feature
<222> LOCATION: 589, 590, 591, 592, 593
<223> OTHER INFORMATION: n = A,T,C or G

<400> SEQUENCE: 51

```
gtgggaatcc agtttttga gtttcagtca ttcccgataa attgccttag cattgaatgt     60

ctagattccc gcctgcgcgg gaatgacgaa tccatccgta cggaaacctg caccacgtca    120

ttcccacgaa cctgcaccac gtcattccca cgaacctgca tcccgtcatt cccacgaacc    180

tgcatcccgt cattcccacg agcctgcatc ccgtcattcc cacgaacctg catcccgtca    240

ttcccacgaa cctgcatccc gtcattccca cgaacctgca tcccgtcatt cccacgaacc    300

tgcatcccgt cattcccacg aacctgcatc ccgtcattcc cacgaacctg catcccgtca    360

ttcccacgaa cctgcatccc gtcattccca cgaaagtggg aatccagttc gttcggtttc    420

gcttgtttta agtttcgggt aacttccact tcgtcattcc cgcgaacctg cattccgtca    480

ttcccacgaa agtgggaatc cagttcgttc ggtttcgctt gttttaagtt tcgggtaact    540

tccacttcgt cattcccgcg aacctacatt ccgtcattcc cacgaaagnn nnncacacac    600

ttaattaatt aa                                                        612
```

<210> SEQ ID NO 52
<211> LENGTH: 203
<212> TYPE: PRT
<213> ORGANISM: Neisseria meningitidis
<220> FEATURE:
<221> NAME/KEY: VARIANT
<222> LOCATION: 197, 198
<223> OTHER INFORMATION: Xaa = Any Amino Acid

<400> SEQUENCE: 52

```
Met Gly Ile Gln Phe Phe Glu Phe Gln Ser Phe Pro Ile Asn Cys Leu
 1               5                  10                  15

Ser Ile Glu Cys Leu Asp Ser Arg Leu Arg Gly Asn Asp Glu Ser Ile
            20                  25                  30

Arg Thr Glu Thr Cys Thr Thr Ser Phe Pro Arg Thr Cys Thr Thr Ser
        35                  40                  45
```

```
Phe Pro Arg Thr Cys Ile Pro Ser Phe Pro Arg Thr Cys Ile Pro Ser
    50                  55                  60

Phe Pro Arg Ala Cys Ile Pro Ser Phe Pro Arg Thr Cys Ile Pro Ser
65                  70                  75                  80

Phe Pro Arg Thr Cys Ile Pro Ser Phe Pro Arg Thr Cys Ile Pro Ser
                85                  90                  95

Phe Pro Arg Thr Cys Ile Pro Ser Phe Pro Arg Thr Cys Ile Pro Ser
            100                 105                 110

Phe Pro Arg Thr Cys Ile Pro Ser Phe Pro Arg Thr Cys Ile Pro Ser
        115                 120                 125

Phe Pro Arg Lys Trp Glu Ser Ser Ser Phe Gly Phe Ala Cys Phe Lys
    130                 135                 140

Phe Arg Val Thr Ser Thr Ser Ser Phe Pro Arg Thr Cys Ile Pro Ser
145                 150                 155                 160

Phe Pro Arg Lys Trp Glu Ser Ser Ser Phe Gly Phe Ala Cys Phe Lys
                165                 170                 175

Phe Arg Val Thr Ser Thr Ser Ser Phe Pro Arg Thr Tyr Ile Pro Ser
            180                 185                 190

Phe Pro Arg Lys Xaa Xaa Thr His Leu Ile Asn
        195                 200
```

<210> SEQ ID NO 53
<211> LENGTH: 1023
<212> TYPE: DNA
<213> ORGANISM: Neisseria meningitidis

<400> SEQUENCE: 53

```
atgctgacaa aaaaggagtt tgagaagttt ttagacgagg tttgcaccgt attgaggcaa     60

gaggcaaaaa acgcaccttt caaatcccaa gatatttttg aaaacagagt tcgtgcgctg    120

tgcattgcaa aaattcccgc ttatgctgac atagttatca atcctgaacc tgtgccgcaa    180

attttccccg atgttccaat aggggaatat ggcgtagaag tcaaattcac gctaaaagat    240

acttggcgca gcgtagcaaa cagtatccaa gagaaaaaca aagctgacgg tgtacagcat    300

atctatgtgg tattcggaaa aatggggggc attcccgatg tgaaatggca actttacgaa    360

gatagcgtaa ttcatgtccg cacatcgcat gttccgcgct ttgaggtaga aatagaatct    420

gatcgaccgt ctctgtttga gggtttcggt atttcctatg ctgaatttgc cgatttggat    480

atgcatgaaa aaatggaata tatccgaaaa tatgcccgta acaggctgaa agaaggcgag    540

cggttatggt ggatagaaga cattgacgca gtagacagcc atgatctgcc tttggaagtg    600

cgcctttaca cttccctgcc gcaggaagaa aaaatccgcc tccgagctga agcagcatta    660

gtctcccccc gtattgtctg ctcaggcagg gcgaagcaca aatacgataa tgccgtcctg    720

tatctgatta cctatcgcgg tgtgctttgt catcaggcgc gggacttatt cagtgcgggc    780

agcgttgcca actcggcgga agactaccgt ggcggaaact atgtagaaaa atctttaaaa    840

ttgattgagc atgaaattga aaaagctgct ttggaaatgg atgatgctct aattgtcgaa    900

tattggggag aaagcgtccc gacagaaaaa cgcctagagt attggattaa gatgttggat    960

gatttggcag atggctggat accttctgaa tcgctattca atggtaggta taaagccaaa   1020

taa                                                                 1023
```

<210> SEQ ID NO 54
<211> LENGTH: 340
<212> TYPE: PRT
<213> ORGANISM: Neisseria meningitidis

<400> SEQUENCE: 54

Met Leu Thr Lys Lys Glu Phe Glu Lys Phe Leu Asp Glu Val Cys Thr
1 5 10 15

Val Leu Arg Gln Glu Ala Lys Asn Ala Pro Phe Lys Ser Gln Asp Ile
20 25 30

Phe Glu Asn Arg Val Arg Ala Leu Cys Ile Ala Lys Ile Pro Ala Tyr
35 40 45

Ala Asp Ile Val Ile Asn Pro Glu Pro Val Pro Gln Ile Phe Pro Asp
50 55 60

Val Pro Ile Gly Glu Tyr Gly Val Glu Val Lys Phe Thr Leu Lys Asp
65 70 75 80

Thr Trp Arg Ser Val Ala Asn Ser Ile Gln Glu Lys Asn Lys Ala Asp
85 90 95

Gly Val Gln His Ile Tyr Val Val Phe Gly Lys Met Gly Gly Ile Pro
100 105 110

Asp Val Lys Trp Gln Leu Tyr Glu Asp Ser Val Ile His Val Arg Thr
115 120 125

Ser His Val Pro Arg Phe Glu Val Glu Ile Glu Ser Asp Arg Pro Ser
130 135 140

Leu Phe Glu Gly Phe Gly Ile Ser Tyr Ala Glu Phe Ala Asp Leu Asp
145 150 155 160

Met His Glu Lys Met Glu Tyr Ile Arg Lys Tyr Ala Arg Asn Arg Leu
165 170 175

Lys Glu Gly Glu Arg Leu Trp Trp Ile Glu Asp Ile Asp Ala Val Asp
180 185 190

Ser His Asp Leu Pro Leu Glu Val Arg Leu Tyr Thr Ser Leu Pro Gln
195 200 205

Glu Glu Lys Ile Arg Leu Arg Ala Glu Ala Ala Leu Val Ser Pro Arg
210 215 220

Ile Val Cys Ser Gly Arg Ala Lys His Lys Tyr Asp Asn Ala Val Leu
225 230 235 240

Tyr Leu Ile Thr Tyr Arg Gly Val Leu Cys His Gln Ala Arg Asp Leu
245 250 255

Phe Ser Ala Gly Ser Val Ala Asn Ser Ala Glu Asp Tyr Arg Gly Gly
260 265 270

Asn Tyr Val Glu Lys Ser Leu Lys Leu Ile Glu His Glu Ile Glu Lys
275 280 285

Ala Ala Leu Glu Met Asp Asp Ala Leu Ile Val Glu Tyr Trp Gly Glu
290 295 300

Ser Val Pro Thr Glu Lys Arg Leu Glu Tyr Trp Ile Lys Met Leu Asp
305 310 315 320

Asp Leu Ala Asp Gly Trp Ile Pro Ser Glu Ser Leu Phe Asn Gly Arg
325 330 335

Tyr Lys Ala Lys
340

<210> SEQ ID NO 55
<211> LENGTH: 1131
<212> TYPE: DNA
<213> ORGANISM: Neisseria meningitidis
<220> FEATURE:
<221> NAME/KEY: misc_feature
<222> LOCATION: 1112, 1113, 1114, 1115, 1116
<223> OTHER INFORMATION: n = A,T,C or G

<400> SEQUENCE: 55

-continued

```
atggtgattt ccaacccccg cgaacttgaa aaactcaaag accggattcc caatctgatc     60

aacatcatcc gcgtcgccat cgtttttccg ctgatgatta tgcacatcct cgggctggaa    120

accggcagcc gtgcgaacct gcacgcttcg tggacggcgt gggcgtttta tgtttggctc    180

gccattgcct gctggctgat ttcttttcc atcatccatc cgcattggca atggcaggct    240

ttgagaatac cgagtttcag cgcggtggcg gacatcacga tgatcggcgt gctgacctac    300

ctgttcggcg gcatcgactc cggcttcggc atcctgattc tgcccttcgt cgtctgctcc    360

tgcctgctca gctacgggcg ctaccccctg ctctattcca gctacgccgc catcctgctg    420

atattcaacg ccattgccga cggcgatatc aatatgtatc cgctgatttt ggatgcaaaa    480

accgtcacca acaccttcgt cctcgtgacc ggctcctatt tcgtcgccat gattgcctcg    540

ctgtcggtca gatacatcga ccgtgccggc aaacttgccc atgaaaacca cgccgcctac    600

cgccgcatca ggggcttgaa ccaaatcgtg ctcaaccgcg ttcaggaagc ggtcgtcatc    660

atcaacgtcg agtatcagac cgtactgttc aataaaaagg caaaagatct gctccccacg    720

cttgaaatcg gacagcatac cgccctgttc gaccctatta ccgttttatg ggacaaggcc    780

ccttcgcgta ctttcgaacg caatatcgac acgcccgccc tgaccgcccg catccgcgcc    840

gtgccgatga acaaagagca gaacaagctg ctcatcctct acatccgccc gcaaagcgaa    900

attcaggcag aagccctgtc cgtcaaactt gccgcgctcg gacaactgac cgccaacatc    960

gcccacgaaa tccgcaaccc catgtccgcc atccgccatg caaacgacct gttgcgcgaa   1020

aatatggaag cgggggcggc agatccgttc aacgccaaat tgtgcaaaat catcgacggc   1080

aacgtctgcc gtatcgacaa aatgctcgaa gnnnnncaca cacttaatta a            1131
```

<210> SEQ ID NO 56
<211> LENGTH: 376
<212> TYPE: PRT
<213> ORGANISM: Neisseria meningitidis
<220> FEATURE:
<221> NAME/KEY: VARIANT
<222> LOCATION: 371, 372
<223> OTHER INFORMATION: Xaa = Any Amino Acid

<400> SEQUENCE: 56

```
Met Val Ile Ser Asn Pro Arg Glu Leu Glu Lys Leu Lys Asp Arg Ile
 1               5                  10                  15

Pro Asn Leu Ile Asn Ile Ile Arg Val Ala Ile Val Phe Pro Leu Met
            20                  25                  30

Ile Met His Ile Leu Gly Leu Glu Thr Gly Ser Arg Ala Asn Leu His
        35                  40                  45

Ala Ser Trp Thr Ala Trp Ala Phe Tyr Val Trp Leu Ala Ile Ala Cys
    50                  55                  60

Trp Leu Ile Phe Phe Ser Ile Ile His Pro His Trp Gln Trp Gln Ala
65                  70                  75                  80

Leu Arg Ile Pro Ser Phe Ser Ala Val Ala Asp Ile Thr Met Ile Gly
                85                  90                  95

Val Leu Thr Tyr Leu Phe Gly Gly Ile Asp Ser Gly Phe Gly Ile Leu
            100                 105                 110

Ile Leu Pro Phe Val Val Cys Ser Cys Leu Leu Ser Tyr Gly Arg Tyr
        115                 120                 125

Pro Leu Leu Tyr Ser Ser Tyr Ala Ala Ile Leu Leu Ile Phe Asn Ala
    130                 135                 140

Ile Ala Asp Gly Asp Ile Asn Met Tyr Pro Leu Ile Leu Asp Ala Lys
145                 150                 155                 160
```

```
Thr Val Thr Asn Thr Phe Val Leu Val Thr Gly Ser Tyr Phe Val Ala
                165                 170                 175

Met Ile Ala Ser Leu Ser Val Arg Tyr Ile Asp Arg Ala Gly Lys Leu
            180                 185                 190

Ala His Glu Asn His Ala Ala Tyr Arg Arg Ile Arg Gly Leu Asn Gln
        195                 200                 205

Ile Val Leu Asn Arg Val Gln Glu Ala Val Val Ile Ile Asn Val Glu
    210                 215                 220

Tyr Gln Thr Val Leu Phe Asn Lys Lys Ala Lys Asp Leu Leu Pro Thr
225                 230                 235                 240

Leu Glu Ile Gly Gln His Thr Ala Leu Phe Asp Pro Ile Thr Val Leu
                245                 250                 255

Trp Asp Lys Ala Pro Ser Arg Thr Phe Glu Arg Asn Ile Asp Thr Pro
            260                 265                 270

Ala Leu Thr Ala Arg Ile Arg Ala Val Pro Met Asn Lys Glu Gln Asn
        275                 280                 285

Lys Leu Leu Ile Leu Tyr Ile Arg Pro Gln Ser Glu Ile Gln Ala Glu
    290                 295                 300

Ala Leu Ser Val Lys Leu Ala Ala Leu Gly Gln Leu Thr Ala Asn Ile
305                 310                 315                 320

Ala His Glu Ile Arg Asn Pro Met Ser Ala Ile Arg His Ala Asn Asp
                325                 330                 335

Leu Leu Arg Glu Asn Met Glu Ala Gly Ala Ala Asp Pro Phe Asn Ala
            340                 345                 350

Lys Leu Cys Lys Ile Ile Asp Gly Asn Val Cys Arg Ile Asp Lys Met
        355                 360                 365

Leu Glu Xaa Xaa His Thr Leu Asn
    370                 375


<210> SEQ ID NO 57
<211> LENGTH: 1041
<212> TYPE: DNA
<213> ORGANISM: Neisseria meningitidis
<220> FEATURE:
<221> NAME/KEY: misc_feature
<222> LOCATION: 8, 9, 10, 11, 12
<223> OTHER INFORMATION: n = A,T,C or G

<400> SEQUENCE: 57

gtgtgtgnnn nnaacacctt cgtcctcgtg accggctcct atttcgtcgc catgattgcc      60

tcgctgtcgg tcagatacat cgaccgtgcc ggcaaacttg cccatgaaaa ccacgccgcc     120

taccgccgca tcaggggctt gaaccaaatc gtgctcaacc gcgttcagga agcggtcgtc     180

atcatcaacg tcgagtatca gaccgtactg ttcaataaaa aggcaaaaga tctgctcccc     240

acgcttgaaa tcggacagca taccgccctg ttcgacccta ttaccgtttt atgggacaag     300

gccccttcgc gtactttcga acgcaatatc gacacgcccg ccctgaccgc ccgcatccgc     360

gccgtgccga tgaacaaaga gcagaacaag ctgctcatcc tctacatccg cccgcaaagc     420

gaaattcagg cagaagccct gtccgtcaaa cttgccgcgc tcggacaact gaccgccaac     480

atcgcccacg aaatccgcaa ccccatgtcc gccatccgcc atgcaaacga cctgttgcgc     540

gaaaatatgg aagcgggggc ggcagatccg ttcaacgcca aattgtgcaa aatcatcgac     600

ggcaacgtct gccgtatcga caaaatgctc gaagatattt cctcgctcaa caagcgcaac     660

aaaaccgaac gcgaaaccat cggcctgata ccgttttggg aagaattcaa acaagagttc     720

ctgctcggcc atcccgatgc cgccggctgc atccgcctag atatgcaggg caatcacctg     780
```

-continued

```
actgcctatt tcgatcctgc ccacctgcgg caaattatgt ggaacctcgc caacaacgcg    840

tggcggcaca gccgcaaaca gcccggctcg atttccgtca ccatccgccc cgcgcaaaaa    900

aacaccgtct gtatcctctt tgccgaccgc ccgaagtgca ggaacacctg ttcgaaccct    960

tttacaccac ggcggaaaac ggcaccggcc tcgggctgta tgtcgcccgc gaactggcgc   1020

acgccaattt cggcgatttg a                                             1041
```

```
<210> SEQ ID NO 58
<211> LENGTH: 346
<212> TYPE: PRT
<213> ORGANISM: Neisseria meningitidis
<220> FEATURE:
<221> NAME/KEY: VARIANT
<222> LOCATION: 3, 4
<223> OTHER INFORMATION: Xaa = Any Amino Acid

<400> SEQUENCE: 58

Met Cys Xaa Xaa Asn Thr Phe Val Leu Val Thr Gly Ser Tyr Phe Val
 1               5                  10                  15

Ala Met Ile Ala Ser Leu Ser Val Arg Tyr Ile Asp Arg Ala Gly Lys
            20                  25                  30

Leu Ala His Glu Asn His Ala Ala Tyr Arg Arg Ile Arg Gly Leu Asn
        35                  40                  45

Gln Ile Val Leu Asn Arg Val Gln Glu Ala Val Val Ile Ile Asn Val
    50                  55                  60

Glu Tyr Gln Thr Val Leu Phe Asn Lys Lys Ala Lys Asp Leu Leu Pro
65                  70                  75                  80

Thr Leu Glu Ile Gly Gln His Thr Ala Leu Phe Asp Pro Ile Thr Val
                85                  90                  95

Leu Trp Asp Lys Ala Pro Ser Arg Thr Phe Glu Arg Asn Ile Asp Thr
            100                 105                 110

Pro Ala Leu Thr Ala Arg Ile Arg Ala Val Pro Met Asn Lys Glu Gln
        115                 120                 125

Asn Lys Leu Leu Ile Leu Tyr Ile Arg Pro Gln Ser Glu Ile Gln Ala
    130                 135                 140

Glu Ala Leu Ser Val Lys Leu Ala Ala Leu Gly Gln Leu Thr Ala Asn
145                 150                 155                 160

Ile Ala His Glu Ile Arg Asn Pro Met Ser Ala Ile Arg His Ala Asn
                165                 170                 175

Asp Leu Leu Arg Glu Asn Met Glu Ala Gly Ala Ala Asp Pro Phe Asn
            180                 185                 190

Ala Lys Leu Cys Lys Ile Ile Asp Gly Asn Val Cys Arg Ile Asp Lys
        195                 200                 205

Met Leu Glu Asp Ile Ser Ser Leu Asn Lys Arg Asn Lys Thr Glu Arg
    210                 215                 220

Glu Thr Ile Gly Leu Ile Pro Phe Trp Glu Glu Phe Lys Gln Glu Phe
225                 230                 235                 240

Leu Leu Gly His Pro Asp Ala Ala Gly Cys Ile Arg Leu Asp Met Gln
                245                 250                 255

Gly Asn His Leu Thr Ala Tyr Phe Asp Pro Ala His Leu Arg Gln Ile
            260                 265                 270

Met Trp Asn Leu Ala Asn Asn Ala Trp Arg His Ser Arg Lys Gln Pro
        275                 280                 285

Gly Ser Ile Ser Val Thr Ile Arg Pro Ala Gln Lys Asn Thr Val Cys
    290                 295                 300

Ile Leu Phe Ala Asp Arg Pro Lys Cys Arg Asn Thr Cys Ser Asn Pro
```

305 310 315 320

Phe Thr Pro Arg Arg Lys Thr Ala Pro Ala Ser Gly Cys Met Ser Pro
325 330 335

Ala Asn Trp Arg Thr Pro Ile Ser Ala Ile
340 345

<210> SEQ ID NO 59
<211> LENGTH: 3081
<212> TYPE: DNA
<213> ORGANISM: Neisseria meningitidis

<400> SEQUENCE: 59
atgaataaaa ctttaaaaag gcgggttttc cgccataccg cgctttatgc cgccatcttg 60
atgttttccc ataccggcgg ggggggggg gcgatggcgc aaacccatca atacgctatt 120
atcatgaacg agcgaaagca gcccgaggta aagtcgaatg tgccatcttc aataaaggac 180
aaagacagga aacgcgaata tactcattat aagtacaaaa caggaggagg ctctgtctca 240
ttcaacaata gcgatgagct tgtttctcaa caaagcggta ctgccgtttt tggcacagcc 300
acctacctgc cgccctacgg caaggtttcc ggttttgatg acaaaaggct gaaagagcgc 360
ggcaatgccg ttaattggat tcatacgacc cacccagggt tgataggcta cagctacgcc 420
ggtgtcgtat gcagagacag cacaggctgt cccaaacttg tctataaaac ccgattttcc 480
ttcgataatc ccgacttggc aaaaacagga ggcgggctgg ataggcacac agagccaagc 540
cgcgacaatt cgcccattta caaattgaag gatcatccat ggttgggcgt gtctttcaat 600
ttgggcagcg agaataccgt caaaaatggc aactcattca acaaattgat atcttcttt 660 agtgaaaaca ataataatca aaccatcgtc tctacgacag aaagccaccc tatttccctt 720
ggcgacgggc agcgcgaaca taccgccgtg gtctattatc tgaacgccaa actgcacctg 780
ctggacaaaa aagggattaa agatatcacc gacaaaacag tgcagttggg tgtcttgaag 840
ccgagcatcg atgtgcggaa aggtgccggc tggctaagtt tttgggctag ttgggacatt 900
aaagataccg ggcagattcc agtcaagctc ggcctgcagc aagtcaaagc aggccgctgc 960
atcaataaac cgaaccccaa tcccaaagcc caagcccttt cccccgcact gactgccccc 1020
gcgctgtggt tcggacctgt gcaaaatggt aagatggaga tgtattccgc ttcggtttct 1080
acctaccccg acagttcgag cagccgcatc ttccttcaaa atctgaaaag aaaaaaacgac 1140 cccaacaaac ccggccgcta ttccctcgca gacttgagcg cgtcggagat taaaagtaaa 1200
gagccgactt tcacagggcg gcaaaccgtc atccgattgg ataaaggcgt acatcagatc 1260
aaacttaaag gcaatgaggt cgaaggtttt aagggaaaca acggcaacga cactttcggc 1320
attgttagtg aagggagctt catgcctgat gacagcgagt ggaaaaaagt gctgctgcct 1380
tggacggttc gtgctttcaa tgatgacggt caatttaaca cagtcaacaa agaagaaaac 1440
aacggcaagc caaaatacag tcaaaaatac cgcagccgca acaacggcaa gcacgagcgc 1500
aatttgggcg acatcgtcaa cagccccatc gtggcggtcg gcgagtattt ggctacttcc 1560
gccaacgacg ggatggtgca tatcttcaaa aaaagcggcg gggatgaccg caactatagt 1620
ctgaagctca gttatatccc gggcacgatg ccgcgcaagg atattcaaag ccaagactcc 1680
acccttgcca aagagctgcg cgcctttgcc gaaaaaagct atgtgggcga ccgctacggc 1740
gtggacggcg gctttgtctt gcgccaagtc gaatggaaag ggcaaaaccg cgtgtttatg 1800
ttcggcgcga tgggctttgg cggcagaggt gcatacgcct tggatttgac caaagccgaa 1860
aacggtgacc cgaccgccgt ttccctgttt gatgtcaaac atgacaataa tggcaagaat 1920

```
agcaataata gcgtgcaatt aggctacacc gtcggcacgc cgcaaatcgg caaaacccac   1980

aacggcaaat acgccgcctt cctcgcctct ggttatgcga ctaaagacat taacaacggc   2040

gacaataaaa ccgcgctgta tgtgtatgat ttggaaagca acaacggtac gccgattgca   2100

aaaatcgaag tacccaacgg caagggcggg ctttcgtccc ccacgctggt ggataaagat   2160

ttggacggca cggttgatat cgcctatgcc ggcgatcgcg gcggcagtat gtaccgcttt   2220

gatttaagcg gcaacaaccc gaccagttgg tctgcacgcg ccattttcag cggcaacaaa   2280

ccgattactt ccgcgcccgc catttcccaa ctgaaagaca aacgcgtggt catcttcggc   2340

acgggcagtg atttgagtga ggaggatgtg gacagcaaag aaatccaaca cgtttacggt   2400

atttttgaca atgaaacaga cacgggtacg gcgaaagacg ggcagggcaa cgggctgctc   2460

gagcaagtgc ttagtgagga aaataaaacc ttattcctga ccgattacaa gcgatccgac   2520

ggatcgggca gtaaggggtg ggtagtgaag ctgaaggaag gacagcgcgt taccgtcaaa   2580

ccgaccgtgg tattgcgtac cgcctttgta accatccgca aatataacga cggcggctgc   2640

ggcgcggaaa ccgccatttt gggcatcaat accgccgacg gcggcaagct gaccaagaaa   2700

agcgcgcgcc cgattgtgcc ggacaccaat acggctatcg cgcaatattc cggccataag   2760

aaaggcacca acggcaaatc catccctata ggttgtatgc aaaaaggcaa tgaaatcgtc   2820

tgcccgaacg gatatgttta cgacaaaccg gttaatgtgc gttatctgga tgaaaagaaa   2880

acagacggat tttcaacaac ggcagacggc gatgcgggcg gcagcggtat agaccccgcc   2940

ggcaagcgtg ccggcaaaaa caaccgctgc ttctcccaaa aaggggtgcg caccctgctg   3000

atgaacgatt tggacagctt ggacattacc ggcccgatgt gcggtatgaa acgaatcagc   3060

tggcgtgaag tcttctactg a                                              3081
```

<210> SEQ ID NO 60
<211> LENGTH: 1026
<212> TYPE: PRT
<213> ORGANISM: Neisseria meningitidis

<400> SEQUENCE: 60

```
Met Asn Lys Thr Leu Lys Arg Arg Val Phe Arg His Thr Ala Leu Tyr
 1               5                  10                  15

Ala Ala Ile Leu Met Phe Ser His Thr Gly Gly Gly Gly Gly Ala Met
            20                  25                  30

Ala Gln Thr His Gln Tyr Ala Ile Ile Met Asn Glu Arg Lys Gln Pro
        35                  40                  45

Glu Val Lys Ser Asn Val Pro Ser Ser Ile Lys Asp Lys Asp Arg Lys
    50                  55                  60

Arg Glu Tyr Thr His Tyr Lys Tyr Lys Thr Gly Gly Gly Ser Val Ser
65                  70                  75                  80

Phe Asn Asn Ser Asp Glu Leu Val Ser Gln Gln Ser Gly Thr Ala Val
                85                  90                  95

Phe Gly Thr Ala Thr Tyr Leu Pro Pro Tyr Gly Lys Val Ser Gly Phe
            100                 105                 110

Asp Asp Lys Arg Leu Lys Glu Arg Gly Asn Ala Val Asn Trp Ile His
        115                 120                 125

Thr Thr His Pro Gly Leu Ile Gly Tyr Ser Tyr Ala Gly Val Val Cys
    130                 135                 140

Arg Asp Ser Thr Gly Cys Pro Lys Leu Val Tyr Lys Thr Arg Phe Ser
145                 150                 155                 160

Phe Asp Asn Pro Asp Leu Ala Lys Thr Gly Gly Gly Leu Asp Arg His
                165                 170                 175
```

```
Thr Glu Pro Ser Arg Asp Asn Ser Pro Ile Tyr Lys Leu Lys Asp His
            180                 185                 190

Pro Trp Leu Gly Val Ser Phe Asn Leu Gly Ser Glu Asn Thr Val Lys
        195                 200                 205

Asn Gly Asn Ser Phe Asn Lys Leu Ile Ser Ser Phe Ser Glu Asn Asn
    210                 215                 220

Asn Asn Gln Thr Ile Val Ser Thr Thr Glu Ser His Pro Ile Ser Leu
225                 230                 235                 240

Gly Asp Gly Gln Arg Glu His Thr Ala Val Val Tyr Tyr Leu Asn Ala
                245                 250                 255

Lys Leu His Leu Leu Asp Lys Lys Gly Ile Lys Asp Ile Thr Asp Lys
            260                 265                 270

Thr Val Gln Leu Gly Val Leu Lys Pro Ser Ile Asp Val Arg Lys Gly
        275                 280                 285

Ala Gly Trp Leu Ser Phe Trp Ala Ser Trp Asp Ile Lys Asp Thr Gly
    290                 295                 300

Gln Ile Pro Val Lys Leu Gly Leu Gln Gln Val Lys Ala Gly Arg Cys
305                 310                 315                 320

Ile Asn Lys Pro Asn Pro Asn Pro Lys Ala Gln Ala Leu Ser Pro Ala
                325                 330                 335

Leu Thr Ala Pro Ala Leu Trp Phe Gly Pro Val Gln Asn Gly Lys Met
            340                 345                 350

Glu Met Tyr Ser Ala Ser Val Ser Thr Tyr Pro Asp Ser Ser Ser Ser
        355                 360                 365

Arg Ile Phe Leu Gln Asn Leu Lys Arg Lys Asn Asp Pro Asn Lys Pro
    370                 375                 380

Gly Arg Tyr Ser Leu Ala Asp Leu Ser Ala Ser Glu Ile Lys Ser Lys
385                 390                 395                 400

Glu Pro Thr Phe Thr Gly Arg Gln Thr Val Ile Arg Leu Asp Lys Gly
                405                 410                 415

Val His Gln Ile Lys Leu Lys Gly Asn Glu Val Glu Gly Phe Lys Gly
            420                 425                 430

Asn Asn Gly Asn Asp Thr Phe Gly Ile Val Ser Glu Gly Ser Phe Met
        435                 440                 445

Pro Asp Asp Ser Glu Trp Lys Lys Val Leu Leu Pro Trp Thr Val Arg
    450                 455                 460

Ala Phe Asn Asp Asp Gly Gln Phe Asn Thr Val Asn Lys Glu Glu Asn
465                 470                 475                 480

Asn Gly Lys Pro Lys Tyr Ser Gln Lys Tyr Arg Ser Arg Asn Asn Gly
                485                 490                 495

Lys His Glu Arg Asn Leu Gly Asp Ile Val Asn Ser Pro Ile Val Ala
            500                 505                 510

Val Gly Glu Tyr Leu Ala Thr Ser Ala Asn Asp Gly Met Val His Ile
        515                 520                 525

Phe Lys Lys Ser Gly Gly Asp Asp Arg Asn Tyr Ser Leu Lys Leu Ser
    530                 535                 540

Tyr Ile Pro Gly Thr Met Pro Arg Lys Asp Ile Gln Ser Gln Asp Ser
545                 550                 555                 560

Thr Leu Ala Lys Glu Leu Arg Ala Phe Ala Glu Lys Ser Tyr Val Gly
                565                 570                 575

Asp Arg Tyr Gly Val Asp Gly Gly Phe Val Leu Arg Gln Val Glu Trp
            580                 585                 590

Lys Gly Gln Asn Arg Val Phe Met Phe Gly Ala Met Gly Phe Gly Gly
```

```
        595                 600                 605

Arg Gly Ala Tyr Ala Leu Asp Leu Thr Lys Ala Glu Asn Gly Asp Pro
    610                 615                 620

Thr Ala Val Ser Leu Phe Asp Val Lys His Asp Asn Asn Gly Lys Asn
625                 630                 635                 640

Ser Asn Asn Ser Val Gln Leu Gly Tyr Thr Val Gly Thr Pro Gln Ile
                645                 650                 655

Gly Lys Thr His Asn Gly Lys Tyr Ala Ala Phe Leu Ala Ser Gly Tyr
            660                 665                 670

Ala Thr Lys Asp Ile Asn Asn Gly Asp Asn Lys Thr Ala Leu Tyr Val
        675                 680                 685

Tyr Asp Leu Glu Ser Asn Asn Gly Thr Pro Ile Ala Lys Ile Glu Val
    690                 695                 700

Pro Asn Gly Lys Gly Gly Leu Ser Ser Pro Thr Leu Val Asp Lys Asp
705                 710                 715                 720

Leu Asp Gly Thr Val Asp Ile Ala Tyr Ala Gly Asp Arg Gly Gly Ser
                725                 730                 735

Met Tyr Arg Phe Asp Leu Ser Gly Asn Asn Pro Thr Ser Trp Ser Ala
            740                 745                 750

Arg Ala Ile Phe Ser Gly Asn Lys Pro Ile Thr Ser Ala Pro Ala Ile
        755                 760                 765

Ser Gln Leu Lys Asp Lys Arg Val Val Ile Phe Gly Thr Gly Ser Asp
    770                 775                 780

Leu Ser Glu Glu Asp Val Asp Ser Lys Glu Ile Gln His Val Tyr Gly
785                 790                 795                 800

Ile Phe Asp Asn Glu Thr Asp Thr Gly Thr Ala Lys Asp Gly Gln Gly
                805                 810                 815

Asn Gly Leu Leu Glu Gln Val Leu Ser Glu Glu Asn Lys Thr Leu Phe
            820                 825                 830

Leu Thr Asp Tyr Lys Arg Ser Asp Gly Ser Gly Ser Lys Gly Trp Val
        835                 840                 845

Val Lys Leu Lys Glu Gly Gln Arg Val Thr Val Lys Pro Thr Val Val
    850                 855                 860

Leu Arg Thr Ala Phe Val Thr Ile Arg Lys Tyr Asn Asp Gly Gly Cys
865                 870                 875                 880

Gly Ala Glu Thr Ala Ile Leu Gly Ile Asn Thr Ala Asp Gly Gly Lys
                885                 890                 895

Leu Thr Lys Lys Ser Ala Arg Pro Ile Val Pro Asp Thr Asn Thr Ala
            900                 905                 910

Ile Ala Gln Tyr Ser Gly His Lys Lys Gly Thr Asn Gly Lys Ser Ile
        915                 920                 925

Pro Ile Gly Cys Met Gln Lys Gly Asn Glu Ile Val Cys Pro Asn Gly
    930                 935                 940

Tyr Val Tyr Asp Lys Pro Val Asn Val Arg Tyr Leu Asp Glu Lys Lys
945                 950                 955                 960

Thr Asp Gly Phe Ser Thr Thr Ala Asp Gly Asp Ala Gly Gly Ser Gly
                965                 970                 975

Ile Asp Pro Ala Gly Lys Arg Ala Gly Lys Asn Asn Arg Cys Phe Ser
            980                 985                 990

Gln Lys Gly Val Arg Thr Leu Leu Met Asn Asp Leu Asp Ser Leu Asp
        995                 1000                1005

Ile Thr Gly Pro Met Cys Gly Met Lys Arg Ile Ser Trp Arg Glu Val
    1010                1015                1020
```

Phe Tyr
1025

<210> SEQ ID NO 61
<211> LENGTH: 1002
<212> TYPE: DNA
<213> ORGANISM: Neisseria meningitidis

<400> SEQUENCE: 61
ttgcctgtaa acaaaatgcc gtctgaaccg ccgttcgggc gtcatttgat ttttgcttct 60
ttgacctgcc tcattgatgc agtatgcaaa aaaagatacc gcaaccaaaa cgtttatata 120
ttatctattc tgtgtatgac taggagtaaa cctgtgaacc gaactacctt ctgctgcctt 180
tctctgaccg ccgccctgat tctgaccgcc tgcagcagcg gaggcggcgg aagcggaggc 240
ggcggtgtcg ccgccgacat cggcgcgggg cttgccgatg cactaaccgc accgctcgac 300
cataaagaca aaggtttgaa atccctgaca ttggaagact ccatttccca aaacggaaca 360
ctgaccctgt cggcacaagg tgcggaaaga actttcaaag ccggcgacaa agacaacagt 420
ctcaacacag gcaaactgaa gaacgacaaa atcagccgct tcgactttat ccgtcaaatc 480
gaagtggacg ggcagctcat taccttggag agcggagagt tccaagtgta caaacaaagc 540
cattccgcct taaccgccct tcagaccgag caagtacaag actcggagca ttccgggaag 600
atggttgcga aacgccagtt cagaatcggc gacatagtgg gcgaacatac atcttttggc 660
aagcttccca aagacgtcat ggcgacatat cgcgggacgg cgttcggttc agacgatgcc 720
ggcggaaaac tgacctacac catagatttc gccgccaagc agggacacgg caaaatcgaa 780
catttgaaat cgccagaact caatgttgac ctggccgccg ccgatatcaa gccggatgaa 840
aaacaccatg ccgtcatcag cggttccgtc ctttacaacc aagccgagaa aggcagttac 900
tctctaggca tctttggcgg gcaagcccag gaagttgccg gcagcgcgga agtggaaacc 960
gcaaacggca tacgccatat cggtcttgcc gccaagcaat aa 1002

<210> SEQ ID NO 62
<211> LENGTH: 333
<212> TYPE: PRT
<213> ORGANISM: Neisseria meningitidis

<400> SEQUENCE: 62

Met Pro Val Asn Lys Met Pro Ser Glu Pro Pro Phe Gly Arg His Leu
1 5 10 15

Ile Phe Ala Ser Leu Thr Cys Leu Ile Asp Ala Val Cys Lys Lys Arg
20 25 30

Tyr Arg Asn Gln Asn Val Tyr Ile Leu Ser Ile Leu Cys Met Thr Arg
35 40 45

Ser Lys Pro Val Asn Arg Thr Thr Phe Cys Cys Leu Ser Leu Thr Ala
50 55 60

Ala Leu Ile Leu Thr Ala Cys Ser Ser Gly Gly Gly Gly Ser Gly Gly
65 70 75 80

Gly Gly Val Ala Ala Asp Ile Gly Ala Gly Leu Ala Asp Ala Leu Thr
85 90 95

Ala Pro Leu Asp His Lys Asp Lys Gly Leu Lys Ser Leu Thr Leu Glu
100 105 110

Asp Ser Ile Ser Gln Asn Gly Thr Leu Thr Leu Ser Ala Gln Gly Ala
115 120 125

Glu Arg Thr Phe Lys Ala Gly Asp Lys Asp Asn Ser Leu Asn Thr Gly
130 135 140

```
Lys Leu Lys Asn Asp Lys Ile Ser Arg Phe Asp Phe Ile Arg Gln Ile
145                 150                 155                 160

Glu Val Asp Gly Gln Leu Ile Thr Leu Glu Ser Gly Glu Phe Gln Val
                165                 170                 175

Tyr Lys Gln Ser His Ser Ala Leu Thr Ala Leu Gln Thr Glu Gln Val
            180                 185                 190

Gln Asp Ser Glu His Ser Gly Lys Met Val Ala Lys Arg Gln Phe Arg
        195                 200                 205

Ile Gly Asp Ile Val Gly Glu His Thr Ser Phe Gly Lys Leu Pro Lys
    210                 215                 220

Asp Val Met Ala Thr Tyr Arg Gly Thr Ala Phe Gly Ser Asp Asp Ala
225                 230                 235                 240

Gly Gly Lys Leu Thr Tyr Thr Ile Asp Phe Ala Ala Lys Gln Gly His
                245                 250                 255

Gly Lys Ile Glu His Leu Lys Ser Pro Glu Leu Asn Val Asp Leu Ala
            260                 265                 270

Ala Ala Asp Ile Lys Pro Asp Glu Lys His His Ala Val Ile Ser Gly
        275                 280                 285

Ser Val Leu Tyr Asn Gln Ala Glu Lys Gly Ser Tyr Ser Leu Gly Ile
    290                 295                 300

Phe Gly Gly Gln Ala Gln Glu Val Ala Gly Ser Ala Glu Val Glu Thr
305                 310                 315                 320

Ala Asn Gly Ile Arg His Ile Gly Leu Ala Ala Lys Gln
                325                 330
```

<210> SEQ ID NO 63
<211> LENGTH: 690
<212> TYPE: DNA
<213> ORGANISM: Neisseria meningitidis

<400> SEQUENCE: 63

```
gtgggcgaga tggaaaaaga cgcggatatt gccgcgatgg gttcctattt ggagattttg      60

gcggaagaaa acaataaaag cgtgcttgcc gccattgccc gaaacggcga aatttggaaa     120

aaccccctga cccatcagga aatcacgtct gccttccccc tccgcaaccc catacacaac     180

aacacgatga ttatgcggcg cagcgtcatt gacggcggtt tgcggttcga tcccgcctat     240

atccacgccg aagactataa gttttggtac gaagccggca aattgggcag gctggcgaat     300

taccccgaag ccttggtcaa ataccgtttc catcaagacc agacttcttc caaacacaac     360

ctgcaacagc gtaagacggc gtggaaaatc aaagaagaaa tcagggcggg gtattggaag     420

gcggcaggca taaccgtcgg gtcggactgc ctgaattacg ggcttttgaa atcaacggca     480

tatgcgttgc acgaaaaagc cttgtccgga caggatatcg gatacctccg cctgttcctg     540

tacgaatatt tcttgtcgtt ggaaaagtat tctttgaccg atttactgga ttttctgaca     600

gaccgcgtga tgaggaagct gtttgccgca ccgcaatata ggaaaatcct gaaaaaaatg     660

ttacgccctt ggaaataccg gggctattga                                      690
```

<210> SEQ ID NO 64
<211> LENGTH: 229
<212> TYPE: PRT
<213> ORGANISM: Neisseria meningitidis

<400> SEQUENCE: 64

```
Met Gly Glu Met Glu Lys Asp Ala Asp Ile Ala Ala Met Gly Ser Tyr
 1               5                  10                  15

Leu Glu Ile Leu Ala Glu Glu Asn Asn Lys Ser Val Leu Ala Ala Ile
```

```
            20                  25                  30

Ala Arg Asn Gly Glu Ile Trp Lys Asn Pro Leu Thr His Gln Glu Ile
        35                  40                  45

Thr Ser Ala Phe Pro Leu Arg Asn Pro Ile His Asn Asn Thr Met Ile
    50                  55                  60

Met Arg Arg Ser Val Ile Asp Gly Gly Leu Arg Phe Asp Pro Ala Tyr
65                  70                  75                  80

Ile His Ala Glu Asp Tyr Lys Phe Trp Tyr Glu Ala Gly Lys Leu Gly
                85                  90                  95

Arg Leu Ala Asn Tyr Pro Glu Ala Leu Val Lys Tyr Arg Phe His Gln
            100                 105                 110

Asp Gln Thr Ser Ser Lys His Asn Leu Gln Gln Arg Lys Thr Ala Trp
        115                 120                 125

Lys Ile Lys Glu Glu Ile Arg Ala Gly Tyr Trp Lys Ala Ala Gly Ile
    130                 135                 140

Thr Val Gly Ser Asp Cys Leu Asn Tyr Gly Leu Leu Lys Ser Thr Ala
145                 150                 155                 160

Tyr Ala Leu His Glu Lys Ala Leu Ser Gly Gln Asp Ile Gly Tyr Leu
                165                 170                 175

Arg Leu Phe Leu Tyr Glu Tyr Phe Leu Ser Leu Glu Lys Tyr Ser Leu
            180                 185                 190

Thr Asp Leu Leu Asp Phe Leu Thr Asp Arg Val Met Arg Lys Leu Phe
        195                 200                 205

Ala Ala Pro Gln Tyr Arg Lys Ile Leu Lys Lys Met Leu Arg Pro Trp
    210                 215                 220

Lys Tyr Arg Gly Tyr
225
```

```
<210> SEQ ID NO 65
<211> LENGTH: 627
<212> TYPE: DNA
<213> ORGANISM: Neisseria meningitidis

<400> SEQUENCE: 65

atgacgcaag aacgtttacc cgaatttttc gaccgcgccc cgacgctgac cgtacaagac      60

ccgcttgccg cattcctcgg cgcggccgaa aacggcatcc tcacttaccg ctacgccgat     120

gccgtgcgcc tgtgcggaca ttcctgcccg accgtcgcgg gcgcgtacct gatggttatc     180

aaaggtctga aagcccttta cggcgaagag ctgcccgaac gcggcggcat cgaagccgcc     240

atgcagggag cgcgcgacga aggcacggtc ggcgtaaccg catccgtcgt ccaactcctc     300

accggcgcag cccccgaaac cggcttcgga ggcatcggaa tacagggacg cttcgcccgc     360

cgcaacctct tatcctttgg tgcaggcgaa atcaacggca cactcgcgct ccgccgccgc     420

gacaccggca aaaccgtcgc cgtcagcctc aacgccgccc tgcaaccctt cgcaccgcaa     480

atgcgcgaca tcatgcccaa agccgtcagc ggcagcgcaa gtaccgacga actcaaacac     540

ttcggacaac tctggcaggc acgcgttaaa gcatttttga ccgaatcggc ggacgacccg     600

cagttcgtca tcgtccgcga agtgtga                                         627


<210> SEQ ID NO 66
<211> LENGTH: 208
<212> TYPE: PRT
<213> ORGANISM: Neisseria meningitidis

<400> SEQUENCE: 66

Met Thr Gln Glu Arg Leu Pro Glu Phe Phe Asp Arg Ala Pro Thr Leu
```

```
 1               5                   10                  15

Thr Val Gln Asp Pro Leu Ala Ala Phe Leu Gly Ala Ala Glu Asn Gly
            20                  25                  30

Ile Leu Thr Tyr Arg Tyr Ala Asp Ala Val Arg Leu Cys Gly His Ser
        35                  40                  45

Cys Pro Thr Val Ala Gly Ala Tyr Leu Met Val Ile Lys Gly Leu Lys
    50                  55                  60

Ala Leu Tyr Gly Glu Glu Leu Pro Glu Arg Gly Gly Ile Glu Ala Ala
65                  70                  75                  80

Met Gln Gly Ala Arg Asp Glu Gly Thr Val Gly Val Thr Ala Ser Val
                85                  90                  95

Val Gln Leu Leu Thr Gly Ala Ala Pro Glu Thr Gly Phe Gly Gly Ile
            100                 105                 110

Gly Ile Gln Gly Arg Phe Ala Arg Arg Asn Leu Leu Ser Phe Gly Ala
        115                 120                 125

Gly Glu Ile Asn Gly Thr Leu Ala Leu Arg Arg Arg Asp Thr Gly Lys
    130                 135                 140

Thr Val Ala Val Ser Leu Asn Ala Ala Leu Gln Pro Phe Ala Pro Gln
145                 150                 155                 160

Met Arg Asp Ile Met Pro Lys Ala Val Ser Gly Ser Ala Ser Thr Asp
                165                 170                 175

Glu Leu Lys His Phe Gly Gln Leu Trp Gln Ala Arg Val Lys Ala Phe
            180                 185                 190

Leu Thr Glu Ser Ala Asp Asp Pro Gln Phe Val Ile Val Arg Glu Val
        195                 200                 205


<210> SEQ ID NO 67
<211> LENGTH: 1431
<212> TYPE: DNA
<213> ORGANISM: Neisseria meningitidis
<220> FEATURE:
<221> NAME/KEY: misc_feature
<222> LOCATION: 6, 7, 8, 9, 10
<223> OTHER INFORMATION: n = A,T,C or G

<400> SEQUENCE: 67

gtgtgnnnnn cgaacggttt ggatgcccgt ttacgcgatg atatgcaggc aaaacactac      60

gaaccgggtg gtaaatacca tctgtttggt aatgctcgcg gcagtgttaa aaatcgggtt     120

tacgccgtcc aaacatttga tgcaactgcg gtcggcccca tactgcctat tacacacgaa     180

cggacaggat ttgaaggtgt tatcggctat gaaacccatt tttcagggca cggacatgaa     240

gtacacagtc cgttcgataa tcatgattca agaagcactt ctgatttcag cggcggtgta     300

gacggtggtt ttactgttta ccaacttcat cggacagggt cggaaatcca tccggaggat     360

ggatatgacg gaccgcaagg cagcgattat ccgccccccg gaggagcaag ggatatatac     420

agctactatg tcaaaggaac ttctacaaaa acaaagataa acactgttcc gcaagcccca     480

ttttcagacc gttggctaaa agaaaatgcc ggtgccgcct ctggttttct cagccgtgcg     540

gatgaagcag gaaaactgat atgggaaaac gaccccaatc aaaattggtg gggtaaccgt     600

atggatgata ttcgcggcat catccaaggt gcagccaatc cttttctaac gggttttcag     660

ggattgggag ttggggcaat tacagacagt gcggtaaacc cggtaaccta tgcggcagca     720

cggaaaactt tacagggtat tcacaattta ggaaatttaa gtccggaagc acaacttgcg     780

gccgcaaccg cattacaaga cagtgctttt gcggtaaaag acagtatcaa ctctgccaga     840

caatgggctg atgcccatcc gaatataact gcaacagccc aaactgccct ttccgtagca     900
```

-continued

```
gaggccgcag gtacggtttg gggcggtaaa aaagtagaac ttaacccgac taaatgggat    960

tgggttaaaa ataccgatta taaaacacct gctgcccgac ctatgcagac tttagatggg   1020

gaaatggccg gtgggaataa accgcctaaa tctataacgt ctggaggaaa agccaatgct   1080

gcaacttatc ctcaattagt taatcaatta actgggcaaa acttaaaaaa cattgcggct   1140

caagatccaa gattgagtct agctcttcat aagagtgaaa aaaattttcc aataggaact   1200

gcaacttatg aagaggcaga taggctaggt aaaatttggg ttggtgaggg tgcaagacaa   1260

actagtggag gcggatggtt aagtatagat ggcactcgac aatatcggcc accaacagaa   1320

aaaaattcac aatttgcaac tacaggtatt caagcaaatt ttgaaactta tactattgat   1380

tcaaatggaa aaaggaataa aattaaaaat ggacatttaa atattaggta a            1431
```

```
<210> SEQ ID NO 68
<211> LENGTH: 476
<212> TYPE: PRT
<213> ORGANISM: Neisseria meningitidis
<220> FEATURE:
<221> NAME/KEY: VARIANT
<222> LOCATION: 2, 3, 4
<223> OTHER INFORMATION: Xaa = Any Amino Acid

<400> SEQUENCE: 68

Met Xaa Xaa Xaa Asn Gly Leu Asp Ala Arg Leu Arg Asp Asp Met Gln
 1               5                  10                  15

Ala Lys His Tyr Glu Pro Gly Gly Lys Tyr His Leu Phe Gly Asn Ala
            20                  25                  30

Arg Gly Ser Val Lys Asn Arg Val Tyr Ala Val Gln Thr Phe Asp Ala
        35                  40                  45

Thr Ala Val Gly Pro Ile Leu Pro Ile Thr His Glu Arg Thr Gly Phe
    50                  55                  60

Glu Gly Val Ile Gly Tyr Glu Thr His Phe Ser Gly His Gly His Glu
65                  70                  75                  80

Val His Ser Pro Phe Asp Asn His Asp Ser Arg Ser Thr Ser Asp Phe
                85                  90                  95

Ser Gly Gly Val Asp Gly Gly Phe Thr Val Tyr Gln Leu His Arg Thr
            100                 105                 110

Gly Ser Glu Ile His Pro Glu Asp Gly Tyr Asp Gly Pro Gln Gly Ser
        115                 120                 125

Asp Tyr Pro Pro Pro Gly Gly Ala Arg Asp Ile Tyr Ser Tyr Tyr Val
    130                 135                 140

Lys Gly Thr Ser Thr Lys Thr Lys Ile Asn Thr Val Pro Gln Ala Pro
145                 150                 155                 160

Phe Ser Asp Arg Trp Leu Lys Glu Asn Ala Gly Ala Ala Ser Gly Phe
                165                 170                 175

Leu Ser Arg Ala Asp Glu Ala Gly Lys Leu Ile Trp Glu Asn Asp Pro
            180                 185                 190

Asn Gln Asn Trp Trp Gly Asn Arg Met Asp Asp Ile Arg Gly Ile Ile
        195                 200                 205

Gln Gly Ala Ala Asn Pro Phe Leu Thr Gly Phe Gln Gly Leu Gly Val
    210                 215                 220

Gly Ala Ile Thr Asp Ser Ala Val Asn Pro Val Thr Tyr Ala Ala Ala
225                 230                 235                 240

Arg Lys Thr Leu Gln Gly Ile His Asn Leu Gly Asn Leu Ser Pro Glu
                245                 250                 255

Ala Gln Leu Ala Ala Ala Thr Ala Leu Gln Asp Ser Ala Phe Ala Val
            260                 265                 270
```

Lys Asp Ser Ile Asn Ser Ala Arg Gln Trp Ala Asp Ala His Pro Asn
        275                 280                 285

Ile Thr Ala Thr Ala Gln Thr Ala Leu Ser Val Ala Glu Ala Ala Gly
    290                 295                 300

Thr Val Trp Gly Gly Lys Lys Val Glu Leu Asn Pro Thr Lys Trp Asp
305                 310                 315                 320

Trp Val Lys Asn Thr Asp Tyr Lys Thr Pro Ala Ala Arg Pro Met Gln
                325                 330                 335

Thr Leu Asp Gly Glu Met Ala Gly Gly Asn Lys Pro Pro Lys Ser Ile
            340                 345                 350

Thr Ser Gly Gly Lys Ala Asn Ala Ala Thr Tyr Pro Gln Leu Val Asn
        355                 360                 365

Gln Leu Thr Gly Gln Asn Leu Lys Asn Ile Ala Ala Gln Asp Pro Arg
    370                 375                 380

Leu Ser Leu Ala Leu His Lys Ser Glu Lys Asn Phe Pro Ile Gly Thr
385                 390                 395                 400

Ala Thr Tyr Glu Glu Ala Asp Arg Leu Gly Lys Ile Trp Val Gly Glu
                405                 410                 415

Gly Ala Arg Gln Thr Ser Gly Gly Gly Trp Leu Ser Ile Asp Gly Thr
            420                 425                 430

Arg Gln Tyr Arg Pro Pro Thr Glu Lys Asn Ser Gln Phe Ala Thr Thr
        435                 440                 445

Gly Ile Gln Ala Asn Phe Glu Thr Tyr Thr Ile Asp Ser Asn Gly Lys
    450                 455                 460

Arg Asn Lys Ile Lys Asn Gly His Leu Asn Ile Arg
465                 470                 475

<210> SEQ ID NO 69
<211> LENGTH: 690
<212> TYPE: DNA
<213> ORGANISM: Neisseria meningitidis
<220> FEATURE:
<221> NAME/KEY: misc_feature
<222> LOCATION: 675, 676, 677, 678, 679
<223> OTHER INFORMATION: n = A,T,C or G

<400> SEQUENCE: 69
gtgggcatca atgccaatcc taactgtgct gatgaagcag gaaaactgat atgggaaaac 60
gaccccaata aaaattggtg ggctaaccgt atggatgata ttcgcggcat cgtccaaggt 120
gcggttaatc ctttttaat gggttttcaa ggagtaggga ttggggcaat tacagacagt 180
gcagtaagcc cggtcacaga tacagccgcg cagcagactc tacaaggtat taatcattta 240
ggaaatttaa gtcccgaagc acaacttgcg gctgcaaccg cattacaaga cagtgctttt 300
gcggtaaaag acggtatcaa ttccgccaga caatgggctg atgcccatcc gaatataact 360
gcaacagccc aaactgccct tgccgtagca gaggccgcag gtacggtttg gcgcggtaaa 420
aaagtaaacc ttaacccgac caagtgggat tgggttaaaa ataccggcta taaaacacct 480
gctgcccgac ctatgcagac tttagatggg gagatggcag gggggaatag accgcctaaa 540
tctataacgt ccaacagcaa agcagatgct tccacacaac cgtctttaca agcgcaacta 600
attggagaac aaattagtag tgggcatgct tataacaagc atgtcataag acaacaagaa 660
tttacggatt taaannnnnc acacacttaa 690

<210> SEQ ID NO 70
<211> LENGTH: 229
<212> TYPE: PRT

<213> ORGANISM: Neisseria meningitidis
<220> FEATURE:
<221> NAME/KEY: VARIANT
<222> LOCATION: 225, 226, 227
<223> OTHER INFORMATION: Xaa = Any Amino Acid

<400> SEQUENCE: 70

```
Met Gly Ile Asn Ala Asn Pro Asn Cys Ala Asp Glu Ala Gly Lys Leu
 1               5                  10                  15

Ile Trp Glu Asn Asp Pro Asn Lys Asn Trp Trp Ala Asn Arg Met Asp
            20                  25                  30

Asp Ile Arg Gly Ile Val Gln Gly Ala Val Asn Pro Phe Leu Met Gly
        35                  40                  45

Phe Gln Gly Val Gly Ile Gly Ala Ile Thr Asp Ser Ala Val Ser Pro
    50                  55                  60

Val Thr Asp Thr Ala Ala Gln Gln Thr Leu Gln Gly Ile Asn His Leu
65                  70                  75                  80

Gly Asn Leu Ser Pro Glu Ala Gln Leu Ala Ala Ala Thr Ala Leu Gln
                85                  90                  95

Asp Ser Ala Phe Ala Val Lys Asp Gly Ile Asn Ser Ala Arg Gln Trp
            100                 105                 110

Ala Asp Ala His Pro Asn Ile Thr Ala Thr Ala Gln Thr Ala Leu Ala
        115                 120                 125

Val Ala Glu Ala Ala Gly Thr Val Trp Arg Gly Lys Lys Val Asn Leu
    130                 135                 140

Asn Pro Thr Lys Trp Asp Trp Val Lys Asn Thr Gly Tyr Lys Thr Pro
145                 150                 155                 160

Ala Ala Arg Pro Met Gln Thr Leu Asp Gly Glu Met Ala Gly Gly Asn
                165                 170                 175

Arg Pro Pro Lys Ser Ile Thr Ser Asn Ser Lys Ala Asp Ala Ser Thr
            180                 185                 190

Gln Pro Ser Leu Gln Ala Gln Leu Ile Gly Glu Gln Ile Ser Ser Gly
        195                 200                 205

His Ala Tyr Asn Lys His Val Ile Arg Gln Gln Glu Phe Thr Asp Leu
    210                 215                 220

Xaa Xaa Xaa His Thr
225
```

<210> SEQ ID NO 71
<211> LENGTH: 1299
<212> TYPE: DNA
<213> ORGANISM: Neisseria meningitidis

<400> SEQUENCE: 71

```
atgaagggga tgatgatgtt tgaacgcagt gtgattgcaa tggcttgtat ttttgccctt      60

tcagcctgtg gggggcggcgg tggcggatcg cccgatgtta aatcggcgga cacgctgtca    120

aaaccggccg ctcctgttgt tgctgaaaaa gagacagagg taaaagaaga tgcgccacag    180

gcaggttctc aaggacaggg tgcgccatcc acacaaggca gccaagatat ggcggcagtt    240

tcggcagaaa atacaggcaa tggcggtgcg gcaacaacgg acaaacccaa aaatgaagac    300

gagggaccgc aaaatgatat gctgcaaaat tccgccgaat ccgcaaatca aacagggaac    360

aaccaacccg ccgattcttc agattccgcc cccgcgtcaa accctgcacc tgcgaatggc    420

ggtagcaatt ttggaagggt tgatttggct aatggcgttt tgattgatgg gccgtcgcaa    480

aatataacgt tgacccactg taaaggcgat tcttgtaatg gtgataattt attggatgaa    540

gaagcaccgt caaaatcaga atttgaaaat ttaaatgagt ctgaacgaat tgagaaatat    600
```

```
aagaaagatg ggaaaagcga taaatttact aatttggttg cgacagcagt tcaagctaat    660

ggaactaaca aatatgtcat catttataaa gacaagtccg cttcatcttc atttgcgcga    720

ttcaggcgtt ctgcacggtc gaggaggtcg cttcctgccg agatgccgct aatccccgtc    780

aatcaggcgg atacgctgat tgtcgatggg gaagcggtca gcctgacggg gcattccggc    840

aatatcttcg cgcccgaagg gaattaccgg tatctgactt acggggcgga aaaattgccc    900

ggcggatcgt atgccctccg tgtgcaaggc gaaccggcaa aaggcgaaat gcttgctggc    960

acggccgtgt acaacggcga agtgctgcat tttcatacgg aaaacggccg tccgtacccg   1020

actagaggca ggtttgccgc aaaagtcgat ttcggcagca aatctgtgga cggcattatc   1080

gacagcggcg atgatttgca tatgggtacg caaaaattca aagccgccat cgatggaaac   1140

ggctttaagg ggacttggac ggaaaatggc ggcggggatg tttccggaag gttttatggc   1200

ccggccggcg aggaagtggc ggggaaatac agctatcgcc cgacagatgc ggaaaagggc   1260

ggattcggcg tgtttgccgg caaaaaagag caggattga                          1299
```

<210> SEQ ID NO 72
<211> LENGTH: 432
<212> TYPE: PRT
<213> ORGANISM: Neisseria meningitidis

<400> SEQUENCE: 72

```
Met Lys Gly Met Met Met Phe Glu Arg Ser Val Ile Ala Met Ala Cys
 1               5                  10                  15

Ile Phe Ala Leu Ser Ala Cys Gly Gly Gly Gly Gly Gly Ser Pro Asp
            20                  25                  30

Val Lys Ser Ala Asp Thr Leu Ser Lys Pro Ala Ala Pro Val Val Ala
        35                  40                  45

Glu Lys Glu Thr Glu Val Lys Glu Asp Ala Pro Gln Ala Gly Ser Gln
    50                  55                  60

Gly Gln Gly Ala Pro Ser Thr Gln Gly Ser Gln Asp Met Ala Ala Val
65                  70                  75                  80

Ser Ala Glu Asn Thr Gly Asn Gly Gly Ala Ala Thr Thr Asp Lys Pro
                85                  90                  95

Lys Asn Glu Asp Glu Gly Pro Gln Asn Asp Met Leu Gln Asn Ser Ala
            100                 105                 110

Glu Ser Ala Asn Gln Thr Gly Asn Asn Gln Pro Ala Asp Ser Ser Asp
        115                 120                 125

Ser Ala Pro Ala Ser Asn Pro Ala Pro Ala Asn Gly Gly Ser Asn Phe
    130                 135                 140

Gly Arg Val Asp Leu Ala Asn Gly Val Leu Ile Asp Gly Pro Ser Gln
145                 150                 155                 160

Asn Ile Thr Leu Thr His Cys Lys Gly Asp Ser Cys Asn Gly Asp Asn
                165                 170                 175

Leu Leu Asp Glu Glu Ala Pro Ser Lys Ser Glu Phe Glu Asn Leu Asn
            180                 185                 190

Glu Ser Glu Arg Ile Glu Lys Tyr Lys Lys Asp Gly Lys Ser Asp Lys
        195                 200                 205

Phe Thr Asn Leu Val Ala Thr Ala Val Gln Ala Asn Gly Thr Asn Lys
    210                 215                 220

Tyr Val Ile Ile Tyr Lys Asp Lys Ser Ala Ser Ser Ser Phe Ala Arg
225                 230                 235                 240

Phe Arg Arg Ser Ala Arg Ser Arg Arg Ser Leu Pro Ala Glu Met Pro
                245                 250                 255
```

-continued

```
Leu Ile Pro Val Asn Gln Ala Asp Thr Leu Ile Val Asp Gly Glu Ala
            260                 265                 270

Val Ser Leu Thr Gly His Ser Gly Asn Ile Phe Ala Pro Glu Gly Asn
        275                 280                 285

Tyr Arg Tyr Leu Thr Tyr Gly Ala Glu Lys Leu Pro Gly Gly Ser Tyr
    290                 295                 300

Ala Leu Arg Val Gln Gly Glu Pro Ala Lys Gly Glu Met Leu Ala Gly
305                 310                 315                 320

Thr Ala Val Tyr Asn Gly Glu Val Leu His Phe His Thr Glu Asn Gly
                325                 330                 335

Arg Pro Tyr Pro Thr Arg Gly Arg Phe Ala Ala Lys Val Asp Phe Gly
            340                 345                 350

Ser Lys Ser Val Asp Gly Ile Ile Asp Ser Gly Asp Asp Leu His Met
        355                 360                 365

Gly Thr Gln Lys Phe Lys Ala Ala Ile Asp Gly Asn Gly Phe Lys Gly
    370                 375                 380

Thr Trp Thr Glu Asn Gly Gly Gly Asp Val Ser Gly Arg Phe Tyr Gly
385                 390                 395                 400

Pro Ala Gly Glu Glu Val Ala Gly Lys Tyr Ser Tyr Arg Pro Thr Asp
                405                 410                 415

Ala Glu Lys Gly Gly Phe Gly Val Phe Ala Gly Lys Lys Glu Gln Asp
            420                 425                 430
```

<210> SEQ ID NO 73
<211> LENGTH: 2430
<212> TYPE: DNA
<213> ORGANISM: Neisseria meningitidis

<400> SEQUENCE: 73

```
atgcggttct caaggtttga gcccaaaggt cgtctgaaac aacaaatacg gtttcagacg      60
acctttcttt caacaagcca ccacggcaat cagacaaaag cagcacatcg ccacatccat     120
gtcggcagta cggccggcac aaccaccatc cgcagcggcg gggataccac cctcaaaggt     180
gcgcagctca tcggcaaagg catacaggca gatacgcgca acctgcatat agaaagtgta     240
caagatactg aaacctctca gagcaaacag caaaacggca atgtccaagt tactgtcggt     300
tacggattca gtgcaagcgg cagttacagc caaagcaaag tcaaagcaga ccatgcctcc     360
gtaaccgagc aaagcggtat ttatgccgga gaagacggct atcaaatcaa ggtcggaaac     420
catacagacc tcaagggcgg tatcatcacc tccggcaaga gtgccgaaga caaaggaaaa     480
aaccttttc agacggccac ccttactgcc agcgacattc aaaaccacag ccgctacgaa     540
ggcagaagct tcggcatagg cggcagtttc gacctgaacg gcggctggga cggcacggtt     600
accgacaaac aaggcaggcc taccgacagg ataagcctgg cagccggcta cggcagcgac     660
agcgacagtc aaagcagcat cacaaaaagc ggcatcaaca cccgcaacat acacatcacc     720
gacgaagcgg gacaacttgc ccgaacaggc aggactgcaa aagaaaccga agcgcgtatc     780
tacaccggca tcgacaccga aactgcggat caacacacag gccgtctgaa aaacagcttc     840
gacaaagacg cggtcgccaa agagatcaac ctgcaaaggg aagtaacgaa ggagttcggc     900
agaaacgccg cccaagccgt agcggccgtt gccgacaaac tcggtaatac ccaaagttac     960
gaacggtatc aggaagcccg aaccctgctg gaggccgaac tgcaaaacac ggacagcaaa    1020
gccgaaaaag ccgccatccg cgcatccctc ggccaagtaa acgcctatct tgccgaaaac    1080
caaagccgct acgacacctg gaaagaaggc ggcataggca ggagcatact gcacggggcg    1140
```

```
gcaggcggac tgacgaccgg aagcctcggc ggcatactgg ccggcagcgg cacttccctt   1200

gctgcaccat atttggacaa agcggcggaa aacctcggtc cggcgggcaa agcggcggtc   1260

aacgcactgg gcggggcggt catcggctat gcggcgggcg ggaatgtcgg tacggcggca   1320

gtgggggcga atgtcgattg gaacaatagg cagctgcatc cgaaagaaac acaaatcctt   1380

aacaaactgt caaaaggcaa atcggctgaa gaacagtacc gcctaaaagc cgctgcatgt   1440

gcattaaccc ggtgcgcgga aggcgtacct gacttcgacc ctctttataa aggactaaaa   1500

aacctccaag atgccggtaa acagtttgta gcggaacaaa acgtattgat gcggacggat   1560

gcatttaaat atggaacatg gaacagcctg aatgatatac gcagcagtta cgaccgtgct   1620

gccaccaaaa ttaagggtgc gggcaatatg ggattgggtg caacgacttt tgtcggttcg   1680

ggtgctatag gcggaggtct gtgcagtacc gggattggct gtgcggccgg tggacttatt   1740

gcaacggcag gtatgaccgg tggttataca caggcctcag aaggaagccg gcaattgttt   1800

ggcacttacc agtccgattt tggtaaaaaa gttgtcctat ctttgggtac accaatagaa   1860

tacgaatcgc cgttagtatc tgatgcgaaa aatctagccg tatggggatt ggaaacgctg   1920

attacgcgca aattgggaaa cttggcaacg ggtgtgaaaa cttccttgac tccgaaaact   1980

gctgacgtac agcgaaatat cctgtcccaa tccgaagtcg gtatcaagtg gggcaagggg   2040

attgaaggac agggaatgcc ttgggaggat tatgtcggta agggcttgtc tgccaatgca   2100

aggttaccta aaaattttaa aacatttgat tattttgatc gtggtacagg cacggcaatc   2160

agtgccaaaa ctctggatac gcaaactacg gcacgcctgt ccaaacccga acagctttac   2220

agtaccatga aagggtacat cgataagacg gcaaatttca aaagttatga attatcagaa   2280

gtaccgttaa gggcagacat gatcaaacag cgcgaaatcc atctggccat acccgcacaa   2340

actaataagg agcaaagatt gcagttgcaa cgtgtggtag agtatggcaa aagtcaaaac   2400

attacagtca aaattacgga gatcgaataa                                    2430
```

<210> SEQ ID NO 74
<211> LENGTH: 809
<212> TYPE: PRT
<213> ORGANISM: Neisseria meningitidis

<400> SEQUENCE: 74

```
Met Arg Phe Ser Arg Phe Glu Pro Lys Gly Arg Leu Lys Gln Gln Ile
 1               5                  10                  15

Arg Phe Gln Thr Thr Phe Leu Ser Thr Ser His His Gly Asn Gln Thr
            20                  25                  30

Lys Ala Ala His Arg His Ile His Val Gly Ser Thr Ala Gly Thr Thr
        35                  40                  45

Thr Ile Arg Ser Gly Gly Asp Thr Thr Leu Lys Gly Ala Gln Leu Ile
    50                  55                  60

Gly Lys Gly Ile Gln Ala Asp Thr Arg Asn Leu His Ile Glu Ser Val
65                  70                  75                  80

Gln Asp Thr Glu Thr Ser Gln Ser Lys Gln Gln Asn Gly Asn Val Gln
                85                  90                  95

Val Thr Val Gly Tyr Gly Phe Ser Ala Ser Gly Ser Tyr Ser Gln Ser
            100                 105                 110

Lys Val Lys Ala Asp His Ala Ser Val Thr Glu Gln Ser Gly Ile Tyr
        115                 120                 125

Ala Gly Glu Asp Gly Tyr Gln Ile Lys Val Gly Asn His Thr Asp Leu
    130                 135                 140

Lys Gly Gly Ile Ile Thr Ser Gly Lys Ser Ala Glu Asp Lys Gly Lys
```

-continued 145 150 155 160

Asn Leu Phe Gln Thr Ala Thr Leu Thr Ala Ser Asp Ile Gln Asn His
165 170 175

Ser Arg Tyr Glu Gly Arg Ser Phe Gly Ile Gly Gly Ser Phe Asp Leu
180 185 190

Asn Gly Gly Trp Asp Gly Thr Val Thr Asp Lys Gln Gly Arg Pro Thr
195 200 205

Asp Arg Ile Ser Leu Ala Ala Gly Tyr Gly Ser Asp Ser Asp Ser Gln
210 215 220

Ser Ser Ile Thr Lys Ser Gly Ile Asn Thr Arg Asn Ile His Ile Thr
225 230 235 240

Asp Glu Ala Gly Gln Leu Ala Arg Thr Gly Arg Thr Ala Lys Glu Thr
245 250 255

Glu Ala Arg Ile Tyr Thr Gly Ile Asp Thr Glu Thr Ala Asp Gln His
260 265 270

Thr Gly Arg Leu Lys Asn Ser Phe Asp Lys Asp Ala Val Ala Lys Glu
275 280 285

Ile Asn Leu Gln Arg Glu Val Thr Lys Glu Phe Gly Arg Asn Ala Ala
290 295 300

Gln Ala Val Ala Ala Val Ala Asp Lys Leu Gly Asn Thr Gln Ser Tyr
305 310 315 320

Glu Arg Tyr Gln Glu Ala Arg Thr Leu Leu Glu Ala Glu Leu Gln Asn
325 330 335

Thr Asp Ser Lys Ala Glu Lys Ala Ala Ile Arg Ala Ser Leu Gly Gln
340 345 350

Val Asn Ala Tyr Leu Ala Glu Asn Gln Ser Arg Tyr Asp Thr Trp Lys
355 360 365

Glu Gly Gly Ile Gly Arg Ser Ile Leu His Gly Ala Ala Gly Gly Leu
370 375 380

Thr Thr Gly Ser Leu Gly Gly Ile Leu Ala Gly Ser Gly Thr Ser Leu
385 390 395 400

Ala Ala Pro Tyr Leu Asp Lys Ala Ala Glu Asn Leu Gly Pro Ala Gly
405 410 415

Lys Ala Ala Val Asn Ala Leu Gly Gly Ala Val Ile Gly Tyr Ala Ala
420 425 430

Gly Gly Asn Val Gly Thr Ala Ala Val Gly Ala Asn Val Asp Trp Asn
435 440 445

Asn Arg Gln Leu His Pro Lys Glu Thr Gln Ile Leu Asn Lys Leu Ser
450 455 460

Lys Gly Lys Ser Ala Glu Glu Gln Tyr Arg Leu Lys Ala Ala Ala Cys
465 470 475 480

Ala Leu Thr Arg Cys Ala Glu Gly Val Pro Asp Phe Asp Pro Leu Tyr
485 490 495

Lys Gly Leu Lys Asn Leu Gln Asp Ala Gly Lys Gln Phe Val Ala Glu
500 505 510

Gln Asn Val Leu Met Arg Thr Asp Ala Phe Lys Tyr Gly Thr Trp Asn
515 520 525

Ser Leu Asn Asp Ile Arg Ser Ser Tyr Asp Arg Ala Ala Thr Lys Ile
530 535 540

Lys Gly Ala Gly Asn Met Gly Leu Gly Ala Thr Thr Phe Val Gly Ser
545 550 555 560

Gly Ala Ile Gly Gly Gly Leu Cys Ser Thr Gly Ile Gly Cys Ala Ala
565 570 575

```
Gly Gly Leu Ile Ala Thr Ala Gly Met Thr Gly Gly Tyr Thr Gln Ala
            580                 585                 590

Ser Glu Gly Ser Arg Gln Leu Phe Gly Thr Tyr Gln Ser Asp Phe Gly
        595                 600                 605

Lys Lys Val Val Leu Ser Leu Gly Thr Pro Ile Glu Tyr Glu Ser Pro
    610                 615                 620

Leu Val Ser Asp Ala Lys Asn Leu Ala Val Trp Gly Leu Glu Thr Leu
625                 630                 635                 640

Ile Thr Arg Lys Leu Gly Asn Leu Ala Thr Gly Val Lys Thr Ser Leu
                645                 650                 655

Thr Pro Lys Thr Ala Asp Val Gln Arg Asn Ile Leu Ser Gln Ser Glu
            660                 665                 670

Val Gly Ile Lys Trp Gly Lys Gly Ile Glu Gly Gln Gly Met Pro Trp
        675                 680                 685

Glu Asp Tyr Val Gly Lys Gly Leu Ser Ala Asn Ala Arg Leu Pro Lys
    690                 695                 700

Asn Phe Lys Thr Phe Asp Tyr Phe Asp Arg Gly Thr Gly Thr Ala Ile
705                 710                 715                 720

Ser Ala Lys Thr Leu Asp Thr Gln Thr Thr Ala Arg Leu Ser Lys Pro
                725                 730                 735

Glu Gln Leu Tyr Ser Thr Met Lys Gly Tyr Ile Asp Lys Thr Ala Asn
            740                 745                 750

Phe Lys Ser Tyr Glu Leu Ser Glu Val Pro Leu Arg Ala Asp Met Ile
        755                 760                 765

Lys Gln Arg Glu Ile His Leu Ala Ile Pro Ala Gln Thr Asn Lys Glu
    770                 775                 780

Gln Arg Leu Gln Leu Gln Arg Val Val Glu Tyr Gly Lys Ser Gln Asn
785                 790                 795                 800

Ile Thr Val Lys Ile Thr Glu Ile Glu
                805
```

<210> SEQ ID NO 75
<211> LENGTH: 2352
<212> TYPE: DNA
<213> ORGANISM: Neisseria meningitidis
<220> FEATURE:
<221> NAME/KEY: misc_feature
<222> LOCATION: 8, 9, 10, 11, 12
<223> OTHER INFORMATION: n = A,T,C or G

<400> SEQUENCE: 75

```
gtgtgtgnnn nngataaacg cagctataaa accggtaagt ggtacaaact aaaacatgtt      60

actgaaatca aagagcataa aaacgccaaa gccgacccgg tgagcctcag tgcgtcacaa     120

ggtattgaaa tcaaatccgg cggcaatatc ggtgcccacg ccaccttgtt tgatgcaccc     180

cgcggctccg ttaaaatcga agccggacgt gggctggttc tctatgccgt ggaagatctc     240

aactacgaca aacttgacac ccgtaccaag cgcaaattta tcggcattac ctacgacaag     300

gtgcacgaca ccaccaccca caccatgaaa accgccctgc cctcaagggt agttgcagaa     360

tcggccaacc tgcaatcagg ctgggacgcc aaactgcaag gcacccagtt tgaaaccacg     420

ctgggcggcg cagccatccg tgcaggtgta ggcgatcagg cacgagcaga tgccaagatt     480

attcttgaag gcatcaaaag tagtgtgcgc actgaaacag taagcagtag caaatctgcc     540

ctctggcaga aacaggccgg acgcggcagc aatatcgaaa ccttgcaact gccaagtttc     600

acaggctccg ttgcgcccgt actctctgcc cccggcggct atatcgttga tattccgaaa     660

ggcaatctga aaaccgaaat cgaaaagctg gccaaacagc ccgaatacgc ctacctgaaa     720
```

```
cagcttcaga cggccaagaa cgtcgattgg aaacaggtgc agcttgtcta cgacaagtgg    780

gactataaag ccgaaggcct gaccggagcc ggagccgcca ttatcgcact ggccgttacc    840

gtggtcacct caggcgcagg aaccggagcc gtattgggat taaacggtgc ggccgccgcc    900

gcaaccgatg cagcattcgc ctctttggcc agccaggctt ccgtatcgtt catcaacaac    960

aaaggcaata tcggtaacac cctgaaagag ctgggcagaa gcagcacggt gaaaaatctg   1020

gtggttgccg ccgctaccgc aggcgtagcc gacaaaatcg gcgcttcggc attgaacaat   1080

gtcagcgata agcagtggat caacaacctg accgtcaacc tggccaatgc gggcagtgcc   1140

gcactgatta ataccgctgt caacggcggc agcctgaaag acaatctgga agcgaatatc   1200

cttgcggctt tggtgaatac tgcgcatgga gaggcagcaa gtaaaatcaa acaattggat   1260

cagcactaca tagtccacaa gattgcccat gccatagcgg gctgtgcggc agcggcggcg   1320

aataagggca agtgtcagga tggcgcgata ggcgctgcag tcggtgagat tgttggtgag   1380

gctttggtta agaatactga tttcagtcgt atgagtgcga ccgaaatcga aaaatctaaa   1440

gcgaagatta ctgcctattc aaaactggtt gccggcactg cgtctgccgt tgtaggcggg   1500

gatgtgaata cagcggcgaa tgcggcacag atagcggtgg agaataatac tttgtatcct   1560

agatgcgttg gtgcaaagtg tgatgaattt caaaaggaac aacaaaaatg gatacgtgaa   1620

aatcctgaag aatatcgaga agttttgctt cttcagacag gatttattcc aattatcggt   1680

gatatacaga gttttgtaca agcacagacc gctgccgatc acctgtttgc tttgctgggt   1740

gtggttccgg gtatcggtga atcgatacag gcctataaag tagcgaaagc ggcaaaaaat   1800

ttacaaggca tgaaaaaagc cttggacaag gcagcaaccg ttgccactgc acagggctat   1860

gtcagtaaaa ccaaaatcaa aatcggtcaa actgaattaa gggttactgc agcaactgac   1920

aaacaattgc tgaaagctat tggcgaagga agggacacga caggtaaaat gaccgagcag   1980

ttatttgact ctttagctaa acaaaatggc ttcagagtgc tttcgggcgg caaatacggc   2040

ggaaataacg gttttgatca tgtatggcag gctgccgatg gtagtgttgt tttgattgta   2100

gaaagtaagc agattaggaa cggtacggta cagctgaatc cgaatggtgc gggtggatat   2160

acgcagatga gtcgtgaatg gattaaacaa gttgtaaaaa gtttacctga tggtagtcct   2220

gctaaggcag ttgtcttaaa agcaaatcag aacggcaaat taaaaacggc aatagcaggc   2280

gttgatcgtc aaacaggtaa ggccgttatt ctttctgtca aagttccttc taaaaccaat   2340

ataaggagat aa                                                       2352
```

<210> SEQ ID NO 76
<211> LENGTH: 783
<212> TYPE: PRT
<213> ORGANISM: Neisseria meningitidis
<220> FEATURE:
<221> NAME/KEY: VARIANT
<222> LOCATION: 3, 4
<223> OTHER INFORMATION: Xaa = Any Amino Acid

<400> SEQUENCE: 76

```
Met Cys Xaa Xaa Asp Lys Arg Ser Tyr Lys Thr Gly Lys Trp Tyr Lys
 1               5                  10                  15

Leu Lys His Val Thr Glu Ile Lys Glu His Lys Asn Ala Lys Ala Asp
            20                  25                  30

Pro Val Ser Leu Ser Ala Ser Gln Gly Ile Glu Ile Lys Ser Gly Gly
        35                  40                  45

Asn Ile Gly Ala His Ala Thr Leu Phe Asp Ala Pro Arg Gly Ser Val
    50                  55                  60
```

```
Lys Ile Glu Ala Gly Arg Gly Leu Val Leu Tyr Ala Val Glu Asp Leu
65                  70                  75                  80

Asn Tyr Asp Lys Leu Asp Thr Arg Thr Lys Arg Lys Phe Ile Gly Ile
                85                  90                  95

Thr Tyr Asp Lys Val His Asp Thr Thr Thr His Thr Met Lys Thr Ala
            100                 105                 110

Leu Pro Ser Arg Val Val Ala Glu Ser Ala Asn Leu Gln Ser Gly Trp
        115                 120                 125

Asp Ala Lys Leu Gln Gly Thr Gln Phe Glu Thr Thr Leu Gly Gly Ala
    130                 135                 140

Ala Ile Arg Ala Gly Val Gly Asp Gln Ala Arg Ala Asp Ala Lys Ile
145                 150                 155                 160

Ile Leu Glu Gly Ile Lys Ser Ser Val Arg Thr Glu Thr Val Ser Ser
                165                 170                 175

Ser Lys Ser Ala Leu Trp Gln Lys Gln Ala Gly Arg Gly Ser Asn Ile
            180                 185                 190

Glu Thr Leu Gln Leu Pro Ser Phe Thr Gly Ser Val Ala Pro Val Leu
        195                 200                 205

Ser Ala Pro Gly Gly Tyr Ile Val Asp Ile Pro Lys Gly Asn Leu Lys
    210                 215                 220

Thr Glu Ile Glu Lys Leu Ala Lys Gln Pro Glu Tyr Ala Tyr Leu Lys
225                 230                 235                 240

Gln Leu Gln Thr Ala Lys Asn Val Asp Trp Lys Gln Val Gln Leu Val
                245                 250                 255

Tyr Asp Lys Trp Asp Tyr Lys Ala Glu Gly Leu Thr Gly Ala Gly Ala
            260                 265                 270

Ala Ile Ile Ala Leu Ala Val Thr Val Val Thr Ser Gly Ala Gly Thr
        275                 280                 285

Gly Ala Val Leu Gly Leu Asn Gly Ala Ala Ala Ala Ala Thr Asp Ala
    290                 295                 300

Ala Phe Ala Ser Leu Ala Ser Gln Ala Ser Val Ser Phe Ile Asn Asn
305                 310                 315                 320

Lys Gly Asn Ile Gly Asn Thr Leu Lys Glu Leu Gly Arg Ser Ser Thr
                325                 330                 335

Val Lys Asn Leu Val Val Ala Ala Ala Thr Ala Gly Val Ala Asp Lys
            340                 345                 350

Ile Gly Ala Ser Ala Leu Asn Asn Val Ser Asp Lys Gln Trp Ile Asn
        355                 360                 365

Asn Leu Thr Val Asn Leu Ala Asn Ala Gly Ser Ala Ala Leu Ile Asn
    370                 375                 380

Thr Ala Val Asn Gly Gly Ser Leu Lys Asp Asn Leu Glu Ala Asn Ile
385                 390                 395                 400

Leu Ala Ala Leu Val Asn Thr Ala His Gly Glu Ala Ala Ser Lys Ile
                405                 410                 415

Lys Gln Leu Asp Gln His Tyr Ile Val His Lys Ile Ala His Ala Ile
            420                 425                 430

Ala Gly Cys Ala Ala Ala Ala Ala Asn Lys Gly Lys Cys Gln Asp Gly
        435                 440                 445

Ala Ile Gly Ala Ala Val Gly Glu Ile Val Gly Glu Ala Leu Val Lys
    450                 455                 460

Asn Thr Asp Phe Ser Arg Met Ser Ala Thr Glu Ile Glu Lys Ser Lys
465                 470                 475                 480

Ala Lys Ile Thr Ala Tyr Ser Lys Leu Val Ala Gly Thr Ala Ser Ala
```

```
                485                 490                 495

Val Val Gly Gly Asp Val Asn Thr Ala Ala Asn Ala Ala Gln Ile Ala
            500                 505                 510

Val Glu Asn Asn Thr Leu Tyr Pro Arg Cys Val Gly Ala Lys Cys Asp
        515                 520                 525

Glu Phe Gln Lys Glu Gln Gln Lys Trp Ile Arg Glu Asn Pro Glu Glu
    530                 535                 540

Tyr Arg Glu Val Leu Leu Leu Gln Thr Gly Phe Ile Pro Ile Ile Gly
545                 550                 555                 560

Asp Ile Gln Ser Phe Val Gln Ala Gln Thr Ala Ala Asp His Leu Phe
                565                 570                 575

Ala Leu Leu Gly Val Val Pro Gly Ile Gly Glu Ser Ile Gln Ala Tyr
            580                 585                 590

Lys Val Ala Lys Ala Ala Lys Asn Leu Gln Gly Met Lys Lys Ala Leu
        595                 600                 605

Asp Lys Ala Ala Thr Val Ala Thr Ala Gln Gly Tyr Val Ser Lys Thr
    610                 615                 620

Lys Ile Lys Ile Gly Gln Thr Glu Leu Arg Val Thr Ala Ala Thr Asp
625                 630                 635                 640

Lys Gln Leu Leu Lys Ala Ile Gly Glu Gly Arg Asp Thr Thr Gly Lys
                645                 650                 655

Met Thr Glu Gln Leu Phe Asp Ser Leu Ala Lys Gln Asn Gly Phe Arg
            660                 665                 670

Val Leu Ser Gly Gly Lys Tyr Gly Gly Asn Asn Gly Phe Asp His Val
        675                 680                 685

Trp Gln Ala Ala Asp Gly Ser Val Val Leu Ile Val Glu Ser Lys Gln
    690                 695                 700

Ile Arg Asn Gly Thr Val Gln Leu Asn Pro Asn Gly Ala Gly Gly Tyr
705                 710                 715                 720

Thr Gln Met Ser Arg Glu Trp Ile Lys Gln Val Val Lys Ser Leu Pro
                725                 730                 735

Asp Gly Ser Pro Ala Lys Ala Val Val Leu Lys Ala Asn Gln Asn Gly
            740                 745                 750

Lys Leu Lys Thr Ala Ile Ala Gly Val Asp Arg Gln Thr Gly Lys Ala
        755                 760                 765

Val Ile Leu Ser Val Lys Val Pro Ser Lys Thr Asn Ile Arg Arg
    770                 775                 780


<210> SEQ ID NO 77
<211> LENGTH: 903
<212> TYPE: DNA
<213> ORGANISM: Neisseria meningitidis
<220> FEATURE:
<221> NAME/KEY: misc_feature
<222> LOCATION: 880, 881, 882, 883, 884
<223> OTHER INFORMATION: n = A,T,C or G

<400> SEQUENCE: 77

gtgagcatta gcgcgccgta tgccaatgaa aacagccgca tcctgctgag caccacggat     60

atcagttcgg aaaacggcaa aatcaaactg caatcctacg gcgaccagtt ctactacgcc    120

ggacagggtg agctctacac cttcgataaa cgcagctata aaaccggtaa gtggtacaaa    180

ctaaaacatg ttactgaaat caaagagcat aaaaacgcca aagccgaccc ggtgagcctc    240

agtgcgtcac aaggtattga aatcaaatcc ggcggcaata tcggtgccca cgccaccttg    300

tttgatgcac cccgcggctc cgttaaaatc gaagccggac gtgggctggt tctctatgcc    360
```

```
gtggaagatc tcaactacga caaacttgac acccgtacca agcgcaaatt tatcggcatt    420

acctacgaca aggtgcacga caccaccacc cacaccatga aaaccgccct gccctcaagg    480

gtagttgcag aatcggccaa cctgcaatca ggctgggacg ccaaactgca aggcacccag    540

tttgaaacca cgctgggcgg cgcagccatc cgtgcaggtg taggcgatca ggcacgagca    600

gatgccaaga ttattcttga aggcatcaaa agtagtgtgc gcactgaaac agtaagcagt    660

agcaaatctg ccctctggca gaaacaggcc ggacgcggca gcaatatcga aaccttgcaa    720

ctgccaagtt tcacaggctc cgttgcgccc gtactctctg cccccggcgg ctatatcgtt    780

gatattccga aaggcaatct gaaaaccgaa atcgaaaagc tggccaaaca gcccgaatac    840

gcctacctga aacagcttca gacggccaag aacgtcgatn nnnncacaca cttaattaat    900

taa                                                                  903


<210> SEQ ID NO 78
<211> LENGTH: 300
<212> TYPE: PRT
<213> ORGANISM: Neisseria meningitidis
<220> FEATURE:
<221> NAME/KEY: VARIANT
<222> LOCATION: 294, 295
<223> OTHER INFORMATION: Xaa = Any Amino Acid

<400> SEQUENCE: 78

Met Ser Ile Ser Ala Pro Tyr Ala Asn Glu Asn Ser Arg Ile Leu Leu
 1               5                  10                  15

Ser Thr Thr Asp Ile Ser Ser Glu Asn Gly Lys Ile Lys Leu Gln Ser
            20                  25                  30

Tyr Gly Asp Gln Phe Tyr Tyr Ala Gly Gln Gly Glu Leu Tyr Thr Phe
        35                  40                  45

Asp Lys Arg Ser Tyr Lys Thr Gly Lys Trp Tyr Lys Leu Lys His Val
    50                  55                  60

Thr Glu Ile Lys Glu His Lys Asn Ala Lys Ala Asp Pro Val Ser Leu
65                  70                  75                  80

Ser Ala Ser Gln Gly Ile Glu Ile Lys Ser Gly Gly Asn Ile Gly Ala
                85                  90                  95

His Ala Thr Leu Phe Asp Ala Pro Arg Gly Ser Val Lys Ile Glu Ala
            100                 105                 110

Gly Arg Gly Leu Val Leu Tyr Ala Val Glu Asp Leu Asn Tyr Asp Lys
        115                 120                 125

Leu Asp Thr Arg Thr Lys Arg Lys Phe Ile Gly Ile Thr Tyr Asp Lys
    130                 135                 140

Val His Asp Thr Thr Thr His Thr Met Lys Thr Ala Leu Pro Ser Arg
145                 150                 155                 160

Val Val Ala Glu Ser Ala Asn Leu Gln Ser Gly Trp Asp Ala Lys Leu
                165                 170                 175

Gln Gly Thr Gln Phe Glu Thr Thr Leu Gly Gly Ala Ala Ile Arg Ala
            180                 185                 190

Gly Val Gly Asp Gln Ala Arg Ala Asp Ala Lys Ile Ile Leu Glu Gly
        195                 200                 205

Ile Lys Ser Ser Val Arg Thr Glu Thr Val Ser Ser Ser Lys Ser Ala
    210                 215                 220

Leu Trp Gln Lys Gln Ala Gly Arg Gly Ser Asn Ile Glu Thr Leu Gln
225                 230                 235                 240

Leu Pro Ser Phe Thr Gly Ser Val Ala Pro Val Leu Ser Ala Pro Gly
                245                 250                 255
```

-continued

| | | | | | | | | | | | | | | | |
|---|---|---|---|---|---|---|---|---|---|---|---|---|---|---|---|
| Gly | Tyr | Ile | Val | Asp | Ile | Pro | Lys | Gly | Asn | Leu | Lys | Thr | Glu | Ile | Glu |
| | | | 260 | | | | | 265 | | | | | 270 | | |
| Lys | Leu | Ala | Lys | Gln | Pro | Glu | Tyr | Ala | Tyr | Leu | Lys | Gln | Leu | Gln | Thr |
| | | 275 | | | | | 280 | | | | | 285 | | | |
| Ala | Lys | Asn | Val | Asp | Xaa | Xaa | Thr | His | Leu | Ile | Asn | | | | |
| | 290 | | | | | 295 | | | | | 300 | | | | |